US012788753B2

(12) United States Patent
Mitra et al.

(10) Patent No.: US 12,788,753 B2
(45) Date of Patent: Nov. 10, 2026

(54) REPOSITIONING THE ANTI-LEPROSY DRUG CLOFAZIMINE AGAINST DRUG-RESISTANT MYELOMA AND PUTATIVE STEM-CELL SUBCLONES

(71) Applicant: Auburn University, Auburn, AL (US)

(72) Inventors: Amit Kumar Mitra, Auburn, AL (US); Harish Kumar, Auburn, AL (US)

(73) Assignee: Auburn University, Auburn, AL (US)

( * ) Notice: Subject to any disclaimer, the term of this patent is extended or adjusted under 35 U.S.C. 154(b) by 590 days.

(21) Appl. No.: 18/320,470

(22) Filed: May 19, 2023

(65) Prior Publication Data

US 2024/0075027 A1 Mar. 7, 2024

Related U.S. Application Data

(60) Provisional application No. 63/343,582, filed on May 19, 2022.

(51) Int. Cl.

| | |
|---|---|
| ***A61K 31/498*** | (2006.01) |
| ***A61K 31/454*** | (2006.01) |
| ***A61K 31/4745*** | (2006.01) |
| ***A61K 31/69*** | (2006.01) |
| ***A61K 38/05*** | (2006.01) |
| ***A61K 38/06*** | (2006.01) |
| ***A61K 38/07*** | (2006.01) |
| ***A61P 35/00*** | (2006.01) |

(52) U.S. Cl.

CPC .......... *A61K 31/498* (2013.01); *A61K 31/454* (2013.01); *A61K 31/69* (2013.01); *A61K 38/05* (2013.01); *A61K 38/06* (2013.01); *A61K 38/07* (2013.01); *A61P 35/00* (2018.01)

(58) Field of Classification Search

CPC .... A61K 31/498; A61K 31/454; A61K 31/69; A61K 38/05; A61K 38/06; A61K 38/07; A61K 31/4745; A61P 35/00

See application file for complete search history.

(56) References Cited

PUBLICATIONS

Cecil Textbook of Medicine, vol. 1, 20 Ed, 1997, pp. 1004-1010 (Year: 1997).*

Wu Q, Qian W, Sun X, Jiang S. Small-molecule inhibitors, immune checkpoint inhibitors, and more: FDA-approved novel therapeutic drugs for solid tumors from 1991 to 2021. J Hematol Oncol. Oct. 8, 2022;15(1):143. doi: 10.1186/s13045-022-01362-9. PMID: 36209184; PMCID: PMC9548212. (Year: 2022).*

Durusu İZ, Hüsnügil HH, Ataş H, Biber A, Gerekçi S, Güleç EA, Özen C. Anti-cancer effect of clofazimine as a single agent and in combination with cisplatin on U266 multiple myeloma cell line. Leuk Res. Apr. 2017;55:33-40. doi: 10.1016/j.leukres.2017.01.019. Epub Jan. 16, 2017. PMID: 28122281. (Year: 2017).*

Bianchi-Smiraglia, Anna, et al. "Inhibition of the aryl hydrocarbon receptor/polyamine biosynthesis axis suppresses multiple myeloma." The Journal of clinical investigation 128.10 (2018): 4682-4696.

Blair, A., D. E. Hogge, and H. J. Sutherland. "Most acute myeloid leukemia progenitor cells with long-term proliferative ability in vitro and in vivo have the phenotype CD34+/CD71-/HLA-DR-. " Blood, The Journal of the American Society of Hematology 92.11 (1998): 4325-4335.

Blommestein, Hedwig M., et al. "Cost-effectiveness of novel treatment sequences for transplant-ineligible patients with multiple myeloma." JAMA network open 4.3 (2021): e213497-e213497.

Bonolo de Campos, Cecilia, et al. ""Direct to Drug" screening as a precision medicine tool in multiple myeloma." Blood cancer journal 10.5 (2020): 54.

Buchsbaum, Samuel, Beatrice Bercovich, and Aaron Ciechanover. "FAT10 is a proteasomal degradation signal that is itself regulated by ubiquitination." Molecular biology of the cell 23.1 (2012): 225-232.

Cholo, Moloko C., et al. "Clofazimine: current status and future prospects." Journal of antimicrobial chemotherapy 67.2 (2012): 290-298.

Chou, Ting-Chao. "Drug combination studies and their synergy quantification using the Chou-Talalay method." Cancer research 70.2 (2010): 440-446.

Chou, Ting-Chao. "Comparison of mass-action law algorithm-based pharmacodynamics with the conventional pharmacokinetic studies." (2013): 665-2.

Deegan, Shane, et al. "Stress-induced self-cannibalism: on the regulation of autophagy by endoplasmic reticulum stress." Cellular and Molecular Life Sciences 70.14 (2013): 2425-2441.

Franqui-Machin, Reinaldo, et al. "Cancer stem cells are the cause of drug resistance in multiple myeloma: fact or fiction?." Oncotarget 6.38 (2015): 40496.

Friedlander, Ruth, et al. "A regulatory link between ER-associated protein degradation and the unfolded-protein response." Nature cell biology 2.7 (2000): 379-384.

Gopal, M., et al. "Systematic review of clofazimine for the treatment of drug-resistant tuberculosis." The International journal of tuberculosis and lung disease 17.8 (2013): 1001-1007.

Guo, Wancheng, et al. "Identification and characterization of multiple myeloma stem cell-like cells." Cancers 13.14 (2021): 3523.

Gupta, Sanjeev, et al. "Mechanisms of ER stress-mediated mitochondrial membrane permeabilization." International journal of cell biology 2010.1 (2010): 170215.

Huff, Carol Ann, and William Matsui. "Multiple myeloma cancer stem cells." Journal of Clinical Oncology 26.17 (2008): 2895-2900.

(Continued)

*Primary Examiner* — Bruck Kifle
*Assistant Examiner* — Kevin S Martin
(74) *Attorney, Agent, or Firm* — Barnes & Thornburg LLP

(57) ABSTRACT

The present invention relates to compositions comprising clofazimine and methods for treating cancer. In various embodiments, the compositions and methods further comprise a proteasome inhibitor and/or immunomodulatory drug. The compositions and methods of the present invention may be used for naïve cancers as well as those that have developed resistance to proteasome inhibitors and/or immunomodulatory drugs.

21 Claims, 31 Drawing Sheets

(56) References Cited

PUBLICATIONS

Jin, Na, et al. "Disulfiram/copper targets stem cell-like ALDH+ population of multiple myeloma by inhibition of ALDH1A1 and Hedgehog pathway." Journal of cellular biochemistry 119.8 (2018): 6882-6893.
Kim, D., et al. "CD19-CD45low/-CD38high/CD138+ plasma cells enrich for human tumorigenic myeloma cells." Leukemia 26.12 (2012): 2530-2537.
Krämer, Andreas, et al. "Causal analysis approaches in ingenuity pathway analysis." Bioinformatics 30.4 (2014): 523-530.
Kuehl, W. Michael, and P. Leif Bergsagel. "Molecular pathogenesis of multiple myeloma and its premalignant precursor." The Journal of clinical investigation 122.10 (2012): 3456-3463.
Kumar, Harish, et al. "Leprosy drug clofazimine activates peroxisome proliferator-activated receptor-γ and synergizes with imatinib to inhibit chronic myeloid leukemia cells." Haematologica 105.4 (2019): 971.
Kumar, Harish, et al. "Single-cell proteomics and tumor RNAseq identify novel pathways associated with clofazimine sensitivity in PI- and IMiD-resistant myeloma, and putative stem-like cells." Frontiers in Oncology 12 (2022): 842200.
Landgren, Ola, and Karim Iskander. "Modern multiple myeloma therapy: deep, sustained treatment response and good clinical outcomes." Journal of internal medicine 281.4 (2017): 365-382.
Landgren, Ola, et al. "Carfilzomib with immunomodulatory drugs for the treatment of newly diagnosed multiple myeloma." Leukemia 33.9 (2019): 2127-2143.
Livak, Kenneth J., and Thomas D. Schmittgen. "Analysis of relative gene expression data using real-time quantitative PCR and the 2-ΔΔCT method." methods 25.4 (2001): 402-408.
Loh, Yen S., et al. "Presence of Hoechst low side populations in multiple myeloma." Leukemia & lymphoma 49.9 (2008): 1813-1816.
Matsui, William, et al. "Characterization of clonogenic multiple myeloma cells." Blood 103.6 (2004): 2332-2336.
Matsui, William, et al. "Clonogenic multiple myeloma progenitors, stem cell properties, and drug resistance." Cancer research 68.1 (2008): 190-197.
Mitra, A. K., et al. "A gene expression signature distinguishes innate response and resistance to proteasome inhibitors in multiple myeloma." Blood cancer journal 7.6 (2017): e581-e581.
Mitra, Amit K., et al. "Single-cell analysis of targeted transcriptome predicts drug sensitivity of single cells within human myeloma tumors." Leukemia 30.5 (2016): 1094-1102.
Mitra, Amit Kumar, et al. "In vitro and ex vivo gene expression profiling reveals differential kinetic response of HSPs and UPR genes is associated with PI resistance in multiple myeloma." Blood cancer journal 10.7 (2020): 78.
Munshi, Nikhil C., and Kenneth C. Anderson. "New strategies in the treatment of multiple myeloma." Clinical cancer research 19.13 (2013): 3337-3344.
Naderi, Ali, et al. "BEX2 is overexpressed in a subset of primary breast cancers and mediates nerve growth factor/ nuclear factor-κB inhibition of apoptosis in breast cancer cell lines." Cancer research 67.14 (2007): 6725-6736.
Naderi, Ali. "Molecular functions of brain expressed X-linked 2 (BEX2) in malignancies." Experimental Cell Research 376.2 (2019): 221-226.
Prince, M. E., et al. "Identification of a subpopulation of cells with cancer stem cell properties in head and neck squamous cell carcinoma." Proceedings of the National Academy of Sciences 104.3 (2007): 973-978.
Rajkumar, S. Vincent, and Shaji Kumar. "Multiple myeloma: diagnosis and treatment." Mayo Clinic Proceedings. vol. 91. No. 1. Elsevier, 2016.
Rajkumar, S. Vincent, et al. "International Myeloma Working Group updated criteria for the diagnosis of multiple myeloma." The lancet oncology 15.12 (2014): e538-e548.
Rajkumar, S. Vincent. "Multiple myeloma: 2013 update on diagnosis, risk-stratification, and management." American journal of hematology 88.3 (2013): 225-235.
Rajkumar, S. Vincent. "Myeloma today: disease definitions and treatment advances." American journal of hematology 91.1 (2016): 90-100.
Reghunathan, Renji, et al. "Clonogenic multiple myeloma cells have shared stemness signature associated with patient survival." Oncotarget 4.8 (2013): 1230.
Ren, Yunzhao R., et al. "Clofazimine inhibits human Kv1. 3 potassium channel by perturbing calcium oscillation in T lymphocytes." PloS one 3.12 (2008): e4009.
Schavgoulidze, A., et al. "Multiple Myeloma: Heterogeneous in Every Way. Cancers 2021, 13, 1285." 2021.
Singh, Sheila K., et al. "Identification of a cancer stem cell in human brain tumors." Cancer research 63.18 (2003): 5821-5828.
Szegezdi, Eva, et al. "Mediators of endoplasmic reticulum stress-induced apoptosis." EMBO reports 7.9 (2006): 880-885.
Van Rensburg, Constance EJ, Gisela Jooné, and Ronald Anderson. "α-Tocopherol antagonizes the multidrug-resistance-reversal activity of cyclosporin A, verapamil, GF120918, clofazimine and B669." Cancer letters 127.1-2 (1998): 107-112.
Vangsted, Annette, Tobias W. Klausen, and Ulla Vogel. "Genetic variations in multiple myeloma II: association with effect of treatment." European journal of haematology 88.2 (2012): 93-117.
Vincenz, Lisa, et al. "Endoplasmic reticulum stress and the unfolded protein response: targeting the Achilles heel of multiple myeloma." Molecular cancer therapeutics 12.6 (2013): 831-843.
Yuan, Shuofeng, et al. "Clofazimine broadly inhibits coronaviruses including SARS-CoV-2." Nature 593.7859 (2021): 418-423.
Zhou, Wen, et al. "ALDH1 activity identifies tumor-initiating cells and links to chromosomal instability signatures in multiple myeloma." Leukemia 28.5 (2014): 1155-1158.

* cited by examiner

FLAM76
LP-1
RPMI8226/P
RPMI8226/VR
U266/P
U266/VR
V
IXA
CLF
IXA + CLF
PI
Annexin-V-FITC Caspase 3/7 activity
120
60
0
FLAM76
LP1
RPMI8226-P
RPMI8226-VR
U266-P
U266-VR
Vehicle
IXA
CLF
IXA+CLF RPMI8226-P
RPMI8226-VR
Cleaved PARP
Cleaved Caspase-3
Cleaved Caspase-9
Cleaved Caspase-8
BCL2
MCL-1
Bax
Beta actin Heatmap: CLF vs Control

Combination (CLF+IXA) vs Control

CLF vs Control

Combination (CLF+IXA) vs Control

Combination (CLF+IXA) vs Control

CLF vs Control

REPOSITIONING THE ANTI-LEPROSY DRUG CLOFAZIMINE AGAINST DRUG-RESISTANT MYELOMA AND PUTATIVE STEM-CELL SUBCLONES

CROSS-REFERENCE TO RELATED APPLICATIONS

This application claims priority under 35 U.S.C. § 119(e) to U.S. Provisional Patent Application No. 63/343,582, filed May 19, 2022, which is herein incorporated by reference in its entirety.

BACKGROUND OF THE INVENTION

Multiple myeloma (MM) is an incurable neoplasm characterized by clonal expansion of malignant antibody-producing post-germinal- center B-cell-derived plasma cells within the bone marrow (Rajkumar et al., 2013, Am J Hematol., 88:226-235). Myeloma is the second-most common hematopoietic malignancy in the United States, with an estimated 34,920 new cases and 12,410 deaths in 2021 (American Cancer Society).

Combination therapy regimens incorporating proteasome inhibitors (PIs) and immunomodulatory drugs (IMiDs; lenalidomide/Revlimid®, pomalidomide) have improved treatment responses, however, despite these improvements, myeloma remains a difficult-to cure disease. This is attributed to dose-limiting toxicities and drug resistance resulting in a median survival rate of only around 7 years (Munshi et al., 2013, Clin Cancer Res., 19:3337-3344) (Rajkumar et al., 2016, AM J Hematol., 91:90-100) (Landgren et al., 2017, J Intern Med., 281:365-382) (Landgren et al., 2019, Leukemia., 33:2127-2143) (Kuehl et al., 2012, J Clin Invest., 122:3456-3463).

Drug resistance is a manifestation of significant complexity and heterogeneity at the molecular level (Rajkumar et al., 2016, AM J Hematol., 91:90-100) (Rajkumar et al., 2016, Mayo Clin Proc., 91:101-119) (Schavgoulidze et al., 2021, Cancers (Basel)., 13(6):1285). In addition, the presence of rare subpopulations of tumor cells with stem cell-like properties like greater clonogenicity, self-renewal, and differentiation capacities, are believed to significantly contribute towards treatment-refractory phenotypes in various cancers, including myeloma (Franqui-Machin et al., 2015, Oncotarget., 6:40496-40506). Moreover, a recent study on the cost-effectiveness of anti-myeloma drugs suggested that although the current therapeutic regimens including monoclonal antibodies and chimeric antigen receptor or CAR-T-cell therapy are promising, the costs outweigh the effectiveness based on willingness-to-pay thresholds (Blommestein et al., 2021, JAMA Netw Open., 4:e213497).

Thus, there is a need in the art for more effective therapeutic strategies for multiple myelomas and targeting PI- and IMiDs-resistant myelomas. This invention satisfies this unmet need.

SUMMARY OF THE INVENTION

In one aspect, the disclosure relates to a cancer therapeutic composition comprising clofazimine or a pharmaceutically acceptable salt or hydrate thereof and one or more selected from the group consisting of: a) one or more proteasome inhibitors; and b) one or more immunomodulatory drugs. In some embodiments, the one or more proteasome inhibitors are one or more selected from the group consisting of bortezomib, carfilzomib, oprozomid, marizomib, delanzomib, and ixazomib. In some embodiments, the one or more immunomodulatory drugs are one or more selected from the group consisting of lenalidomide, pomalidomide, thalidomide, and imiquimod.

In another aspect, the disclosure relates to a method of killing a myeloma cell comprising the step of contacting the cell with an effective amount of a composition comprising clofazimine or a pharmaceutically acceptable salt or hydrate thereof. In some embodiments, the method further comprises contacting the myeloma cell with an effective amount of a composition comprising one or more proteasome inhibitors. In some embodiments, the one or more proteasome inhibitors are one or more selected from the group consisting of bortezomib, carfilzomib, oprozomid, marizomib, delanzomib, and ixazomib.

In some embodiments, the method further comprises contacting the cell with an effective amount of a composition comprising one or more immunomodulatory drugs. In some embodiments, the one or more immunomodulatory drugs are one or more selected from the group consisting of lenalidomide, pomalidomide, thalidomide, and imiquimod. In some embodiments, the myeloma cell is resistant to proteasome inhibitors and/or immunomodulatory drugs.

In another aspect, the disclosure relates to a method of treating cancer in a subject comprising administering to the subject a therapeutically effective amount of a composition comprising clofazimine or a pharmaceutically acceptable salt or hydrate thereof. In some embodiments, the method further comprises administering a therapeutically effective amount of a composition comprising one or more proteasome inhibitors. In some embodiments, the one or more proteasome inhibitors are one or more selected from the group consisting of bortezomib, carfilzomib, oprozomid, marizomib, delanzomib, and ixazomib. In some embodiments, the one or more proteasome inhibitors and clofazimine, or pharmaceutically acceptable salt or hydrate thereof, are administered simultaneously. In some embodiments, the one or more proteasome inhibitors and clofazimine, or pharmaceutically acceptable salt or hydrate thereof, are administered at different times.

In some embodiments, the method further comprises administering a therapeutically effective amount of a composition comprising one or more immunomodulatory drugs. In some embodiments, the one or more immunomodulatory drugs are one or more selected from the group consisting of lenalidomide, pomalidomide, thalidomide, and imiquimod. In some embodiments, the one or more immunomodulatory drugs and clofazimine, or pharmaceutically acceptable salt or hydrate thereof, are administered simultaneously. In some embodiments, the one or more immunomodulatory drugs and clofazimine, or pharmaceutically acceptable salt or hydrate thereof, are administered at different times.

In some embodiments, the method comprises administering a therapeutically effective amount of a composition comprising clofazimine, a therapeutically effective amount of a composition comprising one or more immunomodulatory drugs, and a therapeutically effective amount of a composition comprising one or more proteasome inhibitors.

In some embodiments, the cancer is myeloma, Mantle Cell Lymphoma (MCL), or prostate cancer. In some embodiments, the myeloma is resistant to one or more proteasome inhibitors and/or immunomodulatory drugs.

BRIEF DESCRIPTION OF THE DRAWINGS

The following detailed description of embodiments of the invention will be better understood when read in conjunction with the appended drawings. It should be understood that the invention is not limited to the precise arrangements and instrumentalities of the embodiments shown in the drawings.

FIG. 1A depicts a representative response to single-agent CLF treatment in HMCLs (human myeloma cell lines). FIG. 1B shows a representative ex vivo CLF dose-response plots in patient bone marrow-derived primary myeloma cells.

FIG. 2A depicts representative survival curves of innately sensitive myeloma cells treated with CLF+PI (represented by ixazomib). FIG. 2B depicts representative survival curves of innately resistant myeloma cell lines treated with CLF+PI. FIG. 2C depicts representative survival curves of parental and clonally-derived acquired resistant myeloma cell lines treated with CLF 30 PI. FIG. 2D depicts representative survival curves of parental and clonally-derived acquired PI-resistant myeloma pairs treated with CLF+IMiD (represented by Lenalidomide).

FIG. 3A shows representative elevated cleaved caspase 3 levels induced by CLF. Samples were treated with CLF or DMSO and gated on LIVE cells. Each 'column' represents a cell line pair (except for KP6, which is just the parental). The first three 'rows' are UMAP plots colored by cell line, CLF dose, and cc3 expression. For the final 'row', the FlowSOM meta-cluster results were condensed into cc3 positive and negative cell subsets based on cc3 expression UMAPs and plotted over CLF dose. cc3 is induced in all lines. FIG. 3B demonstrates a representative in downregulation of genes associated with myeloma cell survival with CLF treatment. Representative heatmap for CyTOF analysis is shown for sensitive and PI-resistant, IMiD-resistant, and patient primary cells showing expression of the complete panel. Heatplot was generated in Cytobank displaying the transformed ratio normalized to the first column (DMSO control) of the median of each marker. CyTOF analysis shows shifts in a number of myeloma cell survival markers following clofazimine treatment (10 μM), including IRF4, IKZF1 (Ikaros), IKZF3 (Aiolos), CD229, CD27, pS6, pERK, and IkBa. CLF acts as a PPAR-gamma agonist that synergizes with PIs to enhance the downstream cascade of p65/NFkB/IRF4/Myc downregulation followed by ROS-dependent apoptotic cell death. FIG. 3C depicts representative Western blots showing pre- vs. post-treatment (24 hr) immunoblotting analysis of proteins involved in the p65/NFkB/IRF4/Myc axis and ROS-dependent apoptotic pathways. Beta-actin was used for the normalization of the Western blots. FIG. 3D depicts representative densitometry analysis showing relative band densities between untreated vs. treated cells lines. Band densities were compared to beta-actin.

FIG. 4A depicts representative results of an apoptosis assays performed on Innate and Acquired sensitive-resistant pairs by Annexin V-FITC kit (BD Biosciences) using flow cytometry (BD LSR II). FIG. 4B depicts representative results of Caspase-3/7 activity assays performed using Caspase-Glo 3/7 luminescent assay (Promega Madison, WI) using Synergy 2 Microplate Reader (Biotek). FIG. 4C depicts representative Western blot results demonstrating that CLF treatment results in dysregulation of apoptotic proteins. Larger blots of PARP cleavage and caspase cleavage are provided in FIG. 18. FIG. 4D depicts representative results demonstrating that CLF induces superoxide levels, measured using the fluorescent dye DHE (Sigma), and red fluorescence was detected by flow cytometry. FIG. 4E depicts representative results demonstrating that CLF induces intra-cellular ROS generation. DCFDA (Sigma), which shows fluorescence when oxidized, was used to measure intracellular ROS production by flow cytometry. FIG. 4F depicts representative results demonstrating that CLF increases mitochondrial membrane potential (MMP), assessed using JC-1 (Sigma), a cationic carbocyanine dye that accumulates in mitochondria. Cells were incubated with 5 μM JC-1 dye for 15 min in the dark at 37° C., washed twice in PBS, and then analyzed for red and green fluorescence by flow cytometry. *, $p<0.05$; , $p<0.01$; *, p 21 0.001. FIG. 5, comprising FIG. 5A depicts representative results demonstrating that CLF reduces Aldefluor® (ALDH) activity. Aldehyde dehydrogenase (ALDH) activity was assessed using the Aldefluor™ kit. The brightly fluorescent ALDH+ cells were detected by BD LSR II flowcytometry. i) Innate sensitive and resistant pair; ii) Acquired sensitive and resistant pairs. FIG. 5B depicts representative results demonstrating that CLF erodes quiescent CD138+ (CFSE bright) cells: Untreated and Treated carboxyfluorescein succinimidyl ester (CFSE; Invitrogen)-stained myeloma cells were labeled with CD138−APC and annexin/V-FITC antibodies and then gated using a BD LSR II flow cytometer into non-dividing cells (CD138+CFSE-bright) and dividing cell (CD138+CFSEdim) population based on CFSE fluorescence intensity. Cells cultured in the presence of colchicine (100 ng/ml; Sigma) were used to assess the range of CFSE fluorescence exhibited by cells that were undivided at the end of the culture time. FIG. 5C depicts representative results demonstrating that CLF erodes Side Population (SP) cells in myeloma: Side population cells in PI-resistant cell lines were investigated using cell-permeable DNA binding Vybrant DyeCycle Violet (DCV; Thermofisher) flow cytometry assays. Positive control sample was incubated with 100 μM verapamil (Sigma-Aldrich) for 30 min. FIG. 5D depicts quantification of Side population results from FIG. 5C.

FIG. 6A depicts a representative heatmap comparing CLF single-agent treatment vs. control (untreated). FIG. 6B depicts a Venn Diagram showing 46 significant ($p<0.05$) genes that were common between all the CLF vs. CON signatures in FIG. 6A. FIG. 6C shows the top canonical pathways predicted by IPA analysis based on the 46-gene shared signature in FIG. 6A and FIG. 6B (CLF vs. CON $p<0.05$). FIG. 6D depicts a representative heatmap comparing CLF+Ixazomib combination treatment vs. control (untreated). FIG. 6E depicts a Venn diagram representing common and unique genes between the treatments from FIG. 6D.

FIG. 7A depicts representative IPA results of CLF single-agent treatment.

FIG. 7B depicts representative IPA results of CLF+PI combination treatment. FIG. 7C depicts representative Western blot analysis pre vs. post-treatment (24 hr), demonstrating that CLF induces ER stress and autophagy to kill the myeloma cells.

FIG. 9A depicts representative synergistic effects of clofazimine and proteasome inhibitors (ixazomib). FIG. 9B depicts representative synergistic effects of clofazimine and lenalidomide. Cells were treated as combination and CI values were calculated for each fraction affected (FA; fraction of cells affected/killed) using Calcusyn Software that applies a method proposed by Chou and Talalay's. CI value of less than 0.9 indicates synergism.

FIG. 10A depicts a representative increase in Caspase 3/7 activity by a Caspase-Glo 3/7 luminescent assay (Promega Madison, WI) using Synergy 2 Microplate Reader (Biotek). FIG. 10B depicts representative Western blotting images and densitometry plots showing downregulation of caspase-3 and caspase-9 following CLF treatment in PI-sensitive (FLAM76) and PI-resistant (LP1) myeloma cell lines. FIG. 10C depicts a representatives effect of CLF-treatment on cell cycle progression in myeloma. Cell cycle analysis was performed using propidium iodide (PI) staining followed by flow cytometry analysis. When gated for live cells, the percentage of cells in G0/G1, S, G2/M, and sub G0/G1 phases in pre- vs. post-CLF treatment HMCLs are shown.

FIG. 11A depicts representative cellular superoxide anions measured by using the fluorescent dye DHE (Sigma) and red fluorescence was detected by flow cytometry. FIG. 11B depicts representative mitochondrial membrane potential assessed using JC-1 (Sigma), a cationic carbocyanine dye that accumulates in mitochondria. Cells were incubated with 5 μM JC-1 dye for 15 min in the dark at 37° C., washed twice in PBS and then analyzed for red and green fluorescence by flow cytometry.

FIG. 13A depicts representative results demonstrating that CLF reduces Aldefluor® (ALDH) activity in i) Innate sensitive (FLAM76) and resistant (LP-1) pair; and ii) Acquired sensitive (U266P) and resistant (U266 VR) pair. FIG. 13B depicts representative results demonstrating that CLF erodes quiescent CD138+ (CFSE bright) cells. FIG. 13C depicts representative results demonstrating that CLF erodes Side Population (SP) cells in myeloma.

FIG. 17A depicts a representative scatter plot depicting a bivariate relationship between relative AHR mRNA expression vs CLF IC50 in a panel of myeloma cell lines. CLF treatment response was not significantly correlated with AHR expression. FIG. 17B depicts a representative bar-plot demonstrating cytotoxicity data (IC50) of the AHR antagonist StemRegenin 1 (SR1). FIG. 17C depicts a representative scatter plot showing the SR1 response was correlated with baseline AHR expression.

FIG. 18A depicts an enlarged image of a Western blot for PARP cleavage from FIG. 4C. FIG. 18B depicts an enlarged image of a Western blot for Caspase-3 cleavage from FIG. 4C.

DETAILED DESCRIPTION

Figure 1A:
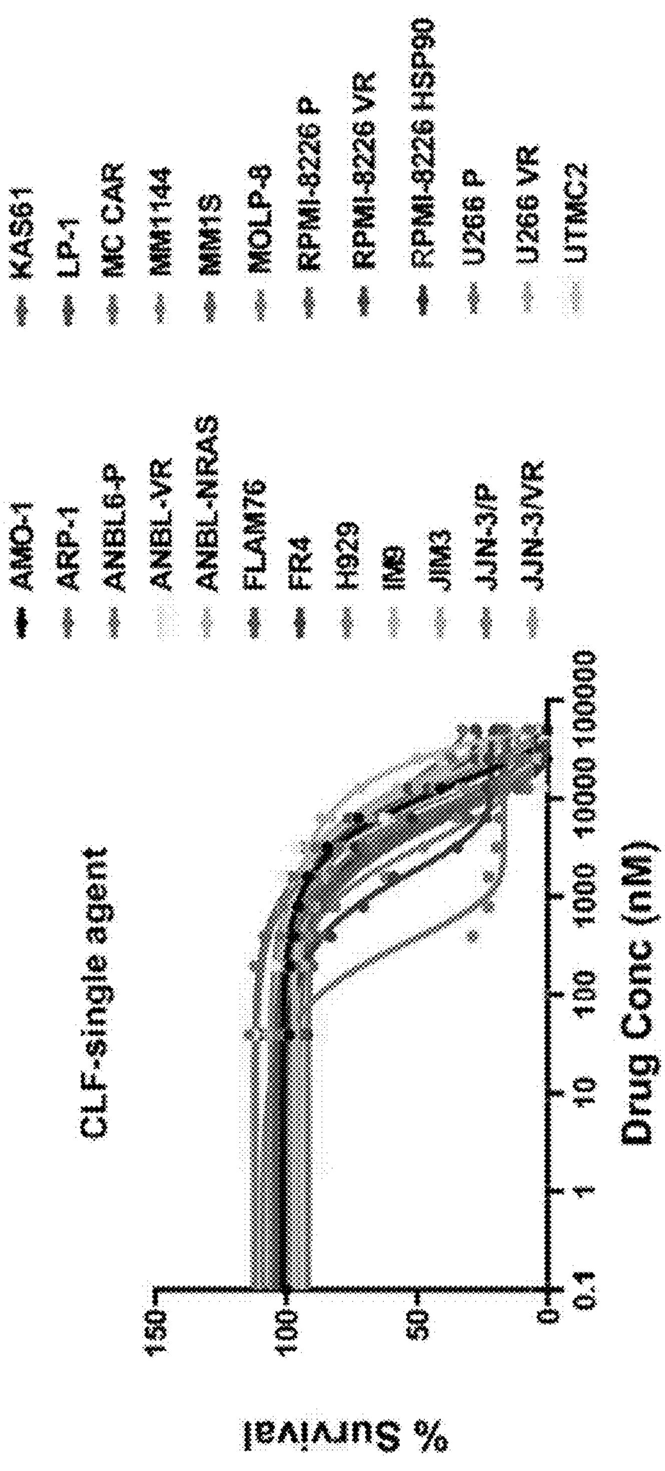
FIG. 1A and FIG. 1B depict representative results of experiments demonstrating that CLF decreases the in vitro and ex vivo cell viability in multiple myeloma.

The present invention relates to compositions and methods for treating cancer. The present invention is based, in part, on the unexpected discovery that clofazimine is a potent anti-cancer compound and yields synergistic activity with other anti-cancer compounds. The present invention is also based on the discovery that clofazimine treatment makes cancer cells that are resistant to certain anti-cancer compounds susceptible to the compounds. Accordingly, in some embodiments, the present disclosure provides compositions comprising clofazimine in combination with additional anti-cancer compounds and methods of treating cancer using clofazimine with and without additional anti-cancer compounds.

Definitions

Unless defined otherwise, all technical and scientific terms used herein have the same meaning as commonly understood by one of ordinary skill in the art to which this invention belongs.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

As used herein, an "immunoassay" refers to any binding assay that uses an antibody capable of binding specifically to a target molecule to detect and quantify the target molecule.

"Cancer," as used herein, refers to the abnormal growth or division of cells. Generally, the growth and/or life span of a cancer cell exceeds, and is not coordinated with, that of the normal cells and tissues around it. Cancers may be benign, pre-malignant or malignant. Cancer occurs in a variety of cells and tissues, including the oral cavity (e.g., mouth, tongue, pharynx, etc.), digestive system (e.g., esophagus, stomach, small intestine, colon, rectum, liver, bile duct, gall bladder, pancreas, etc.), respiratory system (e.g., larynx, lung, bronchus, etc.), bones, joints, skin (e.g., basal cell, squamous cell, meningioma, etc.), breast, genital system, (e.g., uterus, ovary, prostate, testis, etc.), urinary system (e.g., bladder, kidney, ureter, etc.), eye, nervous system (e.g., brain, etc.), endocrine system (e.g., thyroid, etc.), and hematopoietic system (e.g., lymphoma, myeloma, leukemia, acute lymphocytic leukemia, chronic lymphocytic leukemia, acute myeloid leukemia, chronic myeloid leukemia, etc.).

The term "compound," as used herein, unless otherwise indicated, refers to any specific chemical compound disclosed herein. In one embodiment, the term also refers to stereoisomers and/or optical isomers (including racemic mixtures) or enantiomerically enriched mixtures of disclosed compounds.

The term "tautomers" are constitutional isomers of organic compounds that readily interconvert by a chemical process (tautomerization).

The term "isomers" or "stereoisomers" refer to compounds, which have identical chemical constitution, but differ with regard to the arrangement of the atoms or groups in space.

An "effective amount" as used herein, means an amount which provides a therapeutic, prophylactic, or other desired benefit.

As used herein, the terms "therapy" or "therapeutic regimen" refer to those activities taken to prevent, treat or alter a disease or disorder, e.g., a course of treatment intended to reduce or eliminate at least one sign or symptom of a disease or disorder using pharmacological, surgical, dietary and/or other techniques. A therapeutic regimen may include a prescribed dosage of one or more compounds or surgery. Therapies will most often be beneficial and reduce or eliminate at least one sign or symptom of the disorder or disease state, but in some instances the effect of a therapy will have non-desirable or side-effects. The effect of therapy will also be impacted by the physiological state of the subject, e.g., age, gender, genetics, weight, other disease conditions, etc.

As used herein, the term "pharmaceutically acceptable" refers to a material, such as a carrier or diluent, which does not abrogate the biological activity or properties of the compound, and is relatively non-toxic, i.e., the material may be administered to an individual without causing an undesirable biological effect or interacting in a deleterious manner with any of the components of the composition in which it is contained.

As used herein, the term "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary, and topical administration.

As used herein, the term "pharmaceutically acceptable carrier" means a pharmaceutically acceptable material, composition, or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, PA), which is incorporated herein by reference.

The term "therapeutically effective amount" refers to the amount of the subject compound or composition that will elicit the biological, physiologic, clinical or medical response of a cell, tissue, organ, system, or subject that is being sought by the researcher, veterinarian, medical doctor or other clinician. The term "therapeutically effective amount" includes that amount of a compound or composition that, when administered, is sufficient to prevent development of, or treat to some extent, one or more of the signs or symptoms of the disorder or disease being treated. The therapeutically effective amount will vary depending on the compound or composition, the disease and its severity and the age, weight, etc., of the subject to be treated.

To "treat" a disease or disorder as the term is used herein, means to reduce the frequency or severity of at least one sign or symptom of a disease or disorder experienced by a subject. The terms "treatment", "treating", "treat" and the like are used herein to generally refer to obtaining a desired pharmacologic and/or physiologic effect. The effect can be prophylactic in terms of completely or partially preventing a disease or symptom(s) thereof and/or may be therapeutic in terms of a partial or complete stabilization or cure for a disease and/or adverse effect attributable to the disease. The term "treatment" encompasses any treatment of a disease in a mammal, particularly a human, and includes: (a) preventing the disease and/or symptom(s) from occurring in a subject who may be predisposed to the disease or symptom but has not yet been diagnosed as having it; (b) inhibiting the disease and/or symptom(s), e.g., slowing or arresting their development (e.g., halting the growth of tumors, slowing the rate of tumor growth, halting the rate of cancer cell proliferation, and the like); or (c) relieving the disease symptom(s), i.e., causing regression of the disease and/or symptom(s) (e.g., causing decrease in tumor size, reducing the number of cancer cells present, and the like). Those in need of treatment include those already inflicted (e.g., those with cancer, those with an infection, those with a metabolic disorder, those with macular degeneration, etc.) as well as those in which prevention is desired (e.g., those with increased susceptibility to cancer, those with an increased likelihood of infection, those suspected of having cancer, those suspected of harboring an infection, those with increased susceptibility for metabolic disease, those with increased susceptibility for macular degeneration, etc.).

"Sample" or "biological sample" as used herein means a biological material isolated from a subject. The biological sample may contain any biological material suitable for detecting a mRNA, polypeptide or other marker of a physiologic or pathologic process in a subject, and may comprise fluidRanges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention is based, in part, on the unexpected discovery of the anti-cancer activity of clofazimine alone, or in combination with additional anti-cancer compounds. Additionally, the invention is based on the unexpected discovery that clofazimine yields synergistic anti-cancer activity when combined with one or more anti-cancer compounds. The invention is further based on the unexpected discovery that clofazimine is capable of re-sensitizing cancer cells that have developed resistance to one or more anti-cancer compounds. Thus, in one aspect, the present disclosure provides anti-cancer compositions comprising clofazimine and one or more additional anti-cancer compounds which exhibit increased anti-cancer activity.

In another aspect, the disclosure provides methods of treating cancer in a subject. In some embodiments, the cancer is myeloma. In some embodiments, the myeloma is resistant to one or more anti-cancer compounds.

In some embodiments, the method comprises administering clofazimine to the subject. In other embodiments, the method additionally comprises administering to the subject one or more additional anti-cancer compounds. In some embodiments, the method comprises administering an anti-cancer composition of the present invention.

Compositions

In various embodiments, the present disclosure provides compositions comprising clofazimine. In various embodiments, the composition further comprises one or more additional anti-cancer compounds. In some embodiments, the one or more additional anti-cancer compounds are one or more selected form the group consisting of: proteasome inhibitors, immunomodulatory drugs, and Bruton Tyrosine Kinase (BTK) inhibitors.

The compounds of the invention may possess one or more stereocenters, and each stereocenter may exist independently in either the R or S configuration. In one embodiment, compounds described herein are present in optically active or racemic forms. It is to be understood that the compounds described herein encompass racemic, optically active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically active starting materials, chiral synthesis, or chromatographic separation using a chiral stationary phase. In one embodiment, a mixture of one or more isomer is utilized as the therapeutic compound described herein. In another embodiment, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

In one embodiment, compounds described herein are prepared as prodrugs. A "prodrug" refers to an agent that is converted into the parent drug in vivo. In one embodiment, upon in vivo administration, a prodrug is chemically converted to the biologically, pharmaceutically, or therapeutically active form of the compound. In another embodiment, a prodrug is enzymatically metabolized by one or more steps or processes to the biologically, pharmaceutically, or therapeutically active form of the compound.

In some embodiments, the one or more additional anti-cancer compounds are one or more proteasome inhibitors. In some embodiments, the proteasome inhibitors are one or more selected from the group consisting of bortezomib, carfilzomib, oprozomid, marizomib, delanzomib, and ixazomib. In some embodiments, the proteasome inhibitor is ixazomib.

In some embodiments, the one or more additional anti-cancer compounds are one or more immunomodulatory drugs. In some embodiments, the one or more immunomodulatory drugs are one or more selected from the group consisting of lenalidomide, pomalidomide, thalidomide, and imiquimod. In some embodiments, the immunomodulatory drug is lenalidomide.

In some embodiments, the one or more additional anti-cancer compounds are one or more proteasome inhibitors and one or more immunomodulatory drugs. In some embodiments, the proteasome inhibitors are one or more selected from the group consisting of bortezomib, carfilzomib, oprozomid, marizomib, delanzomib, and ixazomib. In some embodiments, the proteasome inhibitor is ixazomib. In some embodiments, the one or more immunomodulatory drugs are one or more selected from the group consisting of lenalidomide, pomalidomide, thalidomide, and imiquimod. In some embodiments, the immunomodulatory drug is lenalidomide. In some embodiments, the proteasome inhibitor is ixazomib and the immunomodulatory drug is lenalidomide.

In some embodiments, the composition comprises clofazimine and a proteasome inhibitor. In some embodiments, the composition comprises clofazimine and a proteasome inhibitor in a weight ratio between about 100,000:1 and about 1:10. In some embodiments, the composition comprises clofazimine and a proteasome inhibitor in a weight ratio between about 80,000:1 and about 1:1. In some embodiments, the composition comprises clofazimine and a proteasome inhibitor in a weight ratio between about 66,000:1 and about 400:1. In some embodiments, the composition comprises clofazimine and a proteasome inhibitor in a weight ratio of about 100,000:1, about 95,000:1, about 90,000:1, about 85,000:1, about 80,000:1, about 75,000:1, about 70,000:1, about 65,000:1, about 60,000:1, about 55,000:1, about 50,000:1, about 45,000:1, about 40,000:1, about 35,000:1, about 30,000:1, about 25,000:1, about 20,000:1, about 15,000:1, about 10,000:1, about 9,000:1, about 8,000:1, about 7,000:1, about 6,000:1, about 5,000:1, about 4,000:1, about 3,000:1, about 2,000:1, about 1,500:1, about 1,400:1, about 1,300:1, about 1,200:1, about 1,100:1, about 1,000:1, about 950:1, about 900:1, about 850:1, about 800:1, about 750:1, about 700:1, about 650:1, about 600:1, about 550:1, about 525:1, about 500:1, about 475:1, about 450:1, about 440:1, about 430:1, about 420:1, about 410:1, about 400:1, about 375:1, about 350:1, about 325:1, about 300:1, about 250:1, about 200:1, about 150:1, about 100:1, about 90:1, about 80:1, about 70:1, about 60:1, about 50:1, about 40:1, about 30:1, about 20:1, about 10:1, about 5:1, about 2:1, about 1:1, about 1:2, about 1:2, about 1:5, or about 1:10.

In some embodiments, the composition comprises clofazimine and an immunomodulatory drug. In some embodiments, the composition comprises clofazimine and an immunomodulatory drug in a weight ratio between about 1,000:1 and about 1:100. In some embodiments, the composition comprises clofazimine and an immunomodulatory drug in a weight ratio between about 500:1 and about 1:10. In some embodiments, the composition comprises clofazimine and an immunomodulatory drug in a weight ratio between about 100:1 and about 10:1. In some embodiments, the composition comprises clofazimine and an immunomodulatory drug in a weight ratio between about 100:1 and about 30:1. In some embodiments, the composition comprises clofazimine and a proteasome inhibitor in a weight ratio of about 1,000:1, about 950:1, about 900:1, about 850:1, about 800:1, about 750:1, about 700:1, about 650:1, about 600:1, about 550:1, about 500:1, about 450:1, about 400:1, about 350:1, about 300:1, about 250:1, about 200:1, about 175:1, about 150:1, about 140:1, about 130:1, about 120:1, about 110:1, about 100:1, about 95:1, about 90:1, about 85:1, about 80:1, about 75:1, about 70:1, about 65:1, about 60:1, about 55:1, about 50:1, about 45:1, about 40:1, about 35:1, about 30:1, about 20:1, about 10:1, about 5:1, about 2:1, about 1:1, about 1:2, about 1:2, about 1:5, about 1:10, or about 1:100.

In some embodiments, the composition comprises a proteasome inhibitor, clofazimine, and an immunomodulatory drug. In some embodiments, the composition comprises a proteasome inhibitor, clofazimine, and an immunomodulatory drug in a weight ratio between about 1 to about 250:about 100,000 to about 500:about 1,000 to about 1. In some embodiments, the composition comprises a proteasome inhibitor, clofazimine, and an immunomodulatory drug in a weight ratio between about 1 to about 175:about 70,000 about 500:about 700 to about 350. In some embodiments, the composition comprises a proteasome inhibitor, clofazimine, and an immunomodulatory drug in a weight ratio of about 1:about 100,000:about 40, about 1:about 100,000:about 30; about 1:about 100,000:about 30, about 1:about 100,000:about 20, about 1:about 100,000:about 10; about 1:about 100,000:about 6, about 1:about 100,000:about 5, about 1:about 70,000:about 40, about 1:about 70,000: about 30, about 1:about 70,000:about 20, about 1:about 70,000:about 10, about 1:about 70,000:about 6, about 1: about 70,000:about 5, 1:about 50:about 40, about 1:about 50,000:about 30; about 1:about 50,000:about 30, about 1:about 50,000:about 20, about 1:about 50,000:about 10; about 1:about 50,000:about 6, about 1:about 50,000:about 5, about 1:about 20,000:about 40, about 1:about 20,000:about 30, about 1:about 20,000:about 20, about 1:about 20,000: about 10, about 1:about 20,000:about 6, about 1:about 20,000:about 5, 1:about 1,000:about 40, about 1:about 1,000:about 30; about 1:about 1,000:about 30, about 1:about 1,000:about 20, about 1:about 1,000:about 10; about 1:about 1,000:about 6, about 1:about 1,000:about 5, about 1:about 500:about 40, about 1:about 500:about 30, about 1:about 500:about 20, about 1:about 500:about 10, about 1:about 500:about 6, about 1:about 500:about 5, 1:about 450:about 40, about 1:about 450:about 30; about 1:about 450:about 30, about 1:about 450:about 20, about 1:about 450:about 10; about 1:about 450:about 6, about 1:about 450:about 5, about 1:about 400:about 40, about 1:about 400:about 30, about 1:about 400:about 20, about 1:about 400:about 10, about 1:about 400:about 6, or about 1:about 400:about 5.

Methods

In various embodiments, the disclosure provides methods of killing cancer cells. In some embodiments, the cancer cells are myeloma cells. In some embodiments, the method comprises contacting the cells with a composition of the present invention. In some embodiments, the method comprises contacting the cells with a composition comprising clofazimine.

In some embodiments, the method further comprises contacting the cells, separately, simultaneously, or sequentially, with a composition comprising clofazimine and a composition comprising one or more proteasome inhibitors. In some embodiments, the one or more proteasome inhibitors are one or more selected from the group consisting of bortezomib, carfilzomib, oprozomid, marizomib, delanzomib, and ixazomib. In some embodiments, the proteasome inhibitor is ixazomib.

In some embodiments, the method comprises contacting the cells with a composition comprising clofazimine before contacting the cells with a composition comprising a proteasome inhibitor. Examples of contacting the cells with a composition comprising clofazimine before contacting the cells with a composition comprising a proteasome inhibitor include, but are not limited to, contacting the cells with a composition comprising clofazimine 4 weeks, 3 weeks, 2 weeks, 7 days, 6 days, 5 days, 4 days, 3 days, 2 days, 36 hours, 24 hours, 22 hours, 20 hours, 18 hours, 16 hours, 14 hours, 12 hours, 10 hours, 9 hours, 8 hours, 7 hours, 6 hours, 5 hours, 4 hours, 3 hours, 2.5 hours, 2 hours, 1.5 hours, 1 hour, 50 minutes, 45 minutes, 40 minutes, 35 minutes, 30 minutes, 25 minutes, 20 minutes, 15 minutes, 10 minutes, 5 minutes, 4 minutes, 3 minutes, 2 minutes, 1 minute, and 30 seconds before contacting the cells with a composition comprising a proteasome inhibitor. In some embodiments, the cells are contacted with a composition comprising clofazimine multiple times before the cells are contacted with a composition comprising a proteasome inhibitor.

In some embodiments, the method comprises contacting the cells simultaneously with clofazimine and a composition comprising a proteasome inhibitor.

In some embodiments, the method comprises contacting the cells with a composition comprising clofazimine after contacting the cells with a composition comprising a proteasome inhibitor. Examples of contacting the cells with a composition comprising clofazimine after contacting the cells with a composition comprising a proteasome inhibitor include, but are not limited to, contacting the cells with a composition comprising clofazimine 4 weeks, 3 weeks, 2 weeks, 7 days, 6 days, 5 days, 4 days, 3 days, 2 days, 36 hours, 24 hours, 22 hours, 20 hours, 18 hours, 16 hours, 14 hours, 12 hours, 10 hours, 9 hours, 8 hours, 7 hours, 6 hours, 5 hours, 4 hours, 3 hours, 2.5 hours, 2 hours, 1.5 hours, 1 hour, 50 minutes, 45 minutes, 40 minutes, 35 minutes, 30 minutes, 25 minutes, 20 minutes, 15 minutes, 10 minutes, 5 minutes, 4 minutes, 3 minutes, 2 minutes, 1 minute, and 30 seconds after contacting the cells with a composition comprising a proteasome inhibitor. In some embodiments, the cells are contacted with a composition comprising a proteasome inhibitor multiple times before the cells are contacted with a composition comprising clofazimine.

In some embodiments, the method comprises contacting the cells, separately, simultaneously, or sequentially, with a composition comprising clofazimine and a composition comprising one or more immunomodulatory drugs. In some embodiments, the one more immunomodulatory drugs are one or more selected from the group consisting of lenalidomide, pomalidomide, thalidomide, and imiquimod. In some embodiments, the immunomodulatory drug is lenalidomide. In some embodiments, the proteasome inhibitor is ixazomib and the immunomodulatory drug is lenalidomide.

In some embodiments, the method comprises contacting the cells with a composition comprising clofazimine before contacting the cells with a composition comprising an immunomodulatory drug. Examples of contacting the cells with a composition comprising clofazimine before contacting the cells with a composition comprising an immunomodulatory drug include, but are not limited to, contacting the cells with a composition comprising clofazimine 4 weeks, 3 weeks, 2 weeks, 7 days, 6 days, 5 days, 4 days, 3 days, 2 days, 36 hours, 24 hours, 22 hours, 20 hours, 18 hours, 16 hours, 14 hours, 12 hours, 10 hours, 9 hours, 8 hours, 7 hours, 6 hours, 5 hours, 4 hours, 3 hours, 2.5 hours, 2 hours, 1.5 hours, 1 hour, 50 minutes, 45 minutes, 40 minutes, 35 minutes, 30 minutes, 25 minutes, 20 minutes, 15 minutes, 10 minutes, 5 minutes, 4 minutes, 3 minutes, 2 minutes, 1 minute, and 30 seconds before contacting the cells with a composition comprising an immunomodulatory drug. In some embodiments, the cells are contacted with a composition comprising clofazimine multiple times before the cells are contacted with a composition comprising an immunomodulatory drug.

In some embodiments, the method comprises contacting the cells simultaneously with clofazimine and a composition comprising an immunomodulatory drug.

In some embodiments, the method comprises contacting the cells with a composition comprising clofazimine after contacting the cells with a composition comprising an immunomodulatory drug. Examples of contacting the cells with a composition comprising clofazimine after contacting the cells with a composition comprising an immunomodulatory drug include, but are not limited to, contacting the cells with a composition comprising clofazimine 4 weeks, 3 weeks, 2 weeks, 7 days, 6 days, 5 days, 4 days, 3 days, 2 days, 36 hours, 24 hours, 22 hours, 20 hours, 18 hours, 16 hours, 14 hours, 12 hours, 10 hours, 9 hours, 8 hours, 7 hours, 6 hours, 5 hours, 4 hours, 3 hours, 2.5 hours, 2 hours, 1.5 hours, 1 hour, 50 minutes, 45 minutes, 40 minutes, 35 minutes, 30 minutes, 25 minutes, 20 minutes, 15 minutes, 10 minutes, 5 minutes, 4 minutes, 3 minutes, 2 minutes, 1 minute, and 30 seconds after contacting the cells with a composition comprising an immunomodulatory drug. In some embodiments, the cells are contacted with a composition comprising an immunomodulatory drug multiple times before the cells are contacted with a composition comprising clofazimine.

In some embodiments, the method comprises separately, simultaneously, or sequentially contacting the cells with a composition comprising clofazimine, a composition comprising one or more proteasome inhibitors, and a composition comprising one or more immunomodulatory drugs. In some embodiments, the one or more proteasome inhibitors are one or more selected from the group consisting of bortezomib, carfilzomib, oprozomid, marizomib, delanzomib, and ixazomib. In some embodiments, the proteasome inhibitor is ixazomib. In some embodiments, the one more immunomodulatory drugs are one or more selected from the group consisting of lenalidomide, pomalidomide, thalidomide, and imiquimod. In some embodiments, the immunomodulatory drug is lenalidomide. In some embodiments, the proteasome inhibitor is ixazomib and the immunomodulatory drug is lenalidomide.

In some embodiments, the method comprises contacting the cells with a composition comprising clofazimine before contacting the cells with a composition comprising a proteasome inhibitor, and then contacting the cells with a composition comprising an immunomodulatory drug. Examples of contacting the cells with a composition comprising clofazimine before contacting the cells with a composition comprising a proteasome inhibitor, and then contacting the cells with a composition comprising an immunomodulatory drug include, but are not limited to, contacting the cells with a composition comprising clofazimine 4 weeks, 3 weeks, 2 weeks, 7 days, 6 days, 5 days, 4 days, 3 days, 2 days, 36 hours, 24 hours, 22 hours, 20 hours, 18 hours, 16 hours, 14 hours, 12 hours, 10 hours, 9 hours, 8 hours, 7 hours, 6 hours, 5 hours, 4 hours, 3 hours, 2.5 hours, 2 hours, 1.5 hours, 1 hour, 50 minutes, 45 minutes, 40 minutes, 35 minutes, 30 minutes, 25 minutes, 20 minutes, 15 minutes, 10 minutes, 5 minutes, 4 minutes, 3 minutes, 2 minutes, 1 minute, and 30 seconds before contacting the cells with a composition comprising a proteasome inhibitor and contacting the cells with a composition comprising an immunomodulatory drug 4 weeks, 3 weeks, 2 weeks, 7 days, 6 days, 5 days, 4 days, 3 days, 2 days, 36 hours, 24 hours, 22 hours, 20 hours, 18 hours, 16 hours, 14 hours, 12 hours, 10 hours, 9 hours, 8 hours, 7 hours, 6 hours, 5 hours, 4 hours, 3 hours, 2.5 hours, 2 hours, 1.5 hours, 1 hour, 50 minutes, 45 minutes, 40 minutes, 35 minutes, 30 minutes, 25 minutes, 20 minutes, 15 minutes, 10 minutes, 5 minutes, 4 minutes, 3 minutes, 2 minutes, 1 minute, and 30 seconds after contacting the cells with the composition comprising the proteasome inhibitor. In some embodiments, the cells are contacted with a composition comprising clofazimine multiple times before the cells are contacted with a composition comprising a proteasome inhibitor. In some embodiments, the cells are contacted with a composition comprising a proteasome inhibitor multiple times before the cells are contacted with a composition comprising an immunomodulatory drug.

In some embodiments, the method comprises contacting the cells with a composition comprising clofazimine before contacting the cells with a composition comprising an immunomodulatory drug, and then contacting the cells with a composition comprising a proteasome inhibitor. Examples of contacting the cells with a composition comprising clofazimine before contacting the cells with a composition comprising an immunomodulatory drug, and then contacting the cells with a composition comprising a proteasome inhibitor include, but are not limited to, contacting the cells with a composition comprising clofazimine 4 weeks, 3 weeks, 2 weeks, 7 days, 6 days, 5 days, 4 days, 3 days, 2 days, 36 hours, 24 hours, 22 hours, 20 hours, 18 hours, 16 hours, 14 hours, 12 hours, 10 hours, 9 hours, 8 hours, 7 hours, 6 hours, 5 hours, 4 hours, 3 hours, 2.5 hours, 2 hours, 1.5 hours, 1 hour, 50 minutes, 45 minutes, 40 minutes, 35 minutes, 30 minutes, 25 minutes, 20 minutes, 15 minutes, 10 minutes, 5 minutes, 4 minutes, 3 minutes, 2 minutes, 1 minute, and 30 seconds before contacting the cells with a composition comprising an immunomodulatory drug and contacting the cells with a composition comprising a proteasome inhibitor 4 weeks, 3 weeks, 2 weeks, 7 days, 6 days, 5 days, 4 days, 3 days, 2 days, 36 hours, 24 hours, 22 hours, 20 hours, 18 hours, 16 hours, 14 hours, 12 hours, 10 hours, 9 hours, 8 hours, 7 hours, 6 hours, 5 hours, 4 hours, 3 hours, 2.5 hours, 2 hours, 1.5 hours, 1 hour, 50 minutes, 45 minutes, 40 minutes, 35 minutes, 30 minutes, 25 minutes, 20 minutes, 15 minutes, 10 minutes, 5 minutes, 4 minutes, 3 minutes, 2 minutes, 1 minute, and 30 seconds after contacting the cells with the composition comprising the immunomodulatory drug. In some embodiments, the cells are contacted with a composition comprising clofazimine multiple times before the cells are contacted with a composition comprising an immunomodulatory drug. In some embodiments, the cells are contacted with a composition comprising an immunomodulatory drug multiple times before the cells are contacted with a composition comprising a proteasome inhibitor.

In some embodiments, the method comprises contacting the cells with a composition comprising a proteasome inhibitor before contacting the cells with a composition comprising clofazimine, and then contacting the cells with a composition comprising an immunomodulatory drug. Examples of contacting the cells with a composition comprising a proteasome inhibitor before contacting the cells with a composition comprising clofazimine, and then contacting the cells with a composition comprising an immunomodulatory drug include, but are not limited to, contacting the cells with a composition comprising a proteasome inhibitor 4 weeks, 3 weeks, 2 weeks, 7 days, 6 days, 5 days, 4 days, 3 days, 2 days, 36 hours, 24 hours, 22 hours, 20 hours, 18 hours, 16 hours, 14 hours, 12 hours, 10 hours, 9 hours, 8 hours, 7 hours, 6 hours, 5 hours, 4 hours, 3 hours, 2.5 hours, 2 hours, 1.5 hours, 1 hour, 50 minutes, 45 minutes, 40 minutes, 35 minutes, 30 minutes, 25 minutes, 20 minutes, 15 minutes, 10 minutes, 5 minutes, 4 minutes, 3 minutes, 2 minutes, 1 minute, and 30 seconds before contacting the cells with a composition comprising clofazimine and contacting the cells with a composition comprising an immunomodulatory drug 4 weeks, 3 weeks, 2 weeks, 7 days, 6 days, 5 days, 4 days, 3 days, 2 days, 36 hours, 24 hours, 22 hours, 20 hours, 18 hours, 16 hours, 14 hours, 12 hours, 10 hours, 9 hours, 8 hours, 7 hours, 6 hours, 5 hours, 4 hours, 3 hours, 2.5 hours, 2 hours, 1.5 hours, 1 hour, 50 minutes, 45 minutes, 40 minutes, 35 minutes, 30 minutes, 25 minutes, 20 minutes, 15 minutes, 10 minutes, 5 minutes, 4 minutes, 3 minutes, 2 minutes, 1 minute, and 30 seconds after contacting the cells with the composition comprising clofazimine. In some embodiments, the cells are contacted with a composition comprising a proteasome inhibitor multiple times before the cells are contacted with a composition comprising clofazimine. In some embodiments, the cells are contacted with a composition comprising clofazimine multiple times before the cells are contacted with a composition comprising an immunomodulatory drug.

In some embodiments, the method comprises contacting the cells with a composition comprising a proteasome inhibitor before contacting the cells with a composition comprising an immunomodulatory drug, and then contacting the cells with a composition comprising clofazimine. Examples of contacting the cells with a composition comprising a proteasome inhibitor before contacting the cells with a composition comprising an immunomodulatory drug, and then contacting the cells with a composition comprising clofazimine include, but are not limited to, contacting the cells with a composition comprising a proteasome inhibitor 4 weeks, 3 weeks, 2 weeks, 7 days, 6 days, 5 days, 4 days, 3 days, 2 days, 36 hours, 24 hours, 22 hours, 20 hours, 18 hours, 16 hours, 14 hours, 12 hours, 10 hours, 9 hours, 8 hours, 7 hours, 6 hours, 5 hours, 4 hours, 3 hours, 2.5 hours, 2 hours, 1.5 hours, 1 hour, 50 minutes, 45 minutes, 40 minutes, 35 minutes, 30 minutes, 25 minutes, 20 minutes, 15 minutes, 10 minutes, 5 minutes, 4 minutes, 3 minutes, 2 minutes, 1 minute, and 30 seconds before contacting the cells with a composition comprising an immunomodulatory drug and contacting the cells with a composition comprising clofazimine 4 weeks, 3 weeks, 2 weeks, 7 days, 6 days, 5 days, 4 days, 3 days, 2 days, 36 hours, 24 hours, 22 hours, 20 hours, 18 hours, 16 hours, 14 hours, 12 hours, 10 hours, 9 hours, 8 hours, 7 hours, 6 hours, 5 hours, 4 hours, 3 hours, 2.5 hours, 2 hours, 1.5 hours, 1 hour, 50 minutes, 45 minutes, 40 minutes, 35 minutes, 30 minutes, 25 minutes, 20 minutes, 15 minutes, 10 minutes, 5 minutes, 4 minutes, 3 minutes, 2 minutes, 1 minute, and 30 seconds after contacting the cells with the composition comprising the immunomodulatory drug. In some embodiments, the cells are contacted with a composition comprising a proteasome inhibitor multiple times before the cells are contacted with a composition comprising an immunomodulatory drug. In some embodiments, the cells are contacted with a composition comprising an immunomodulatory drug multiple times before the cells are contacted with a composition comprising clofazimine.

In some embodiments, the method comprises contacting the cells with a composition comprising an immunomodulatory drug before contacting the cells with a composition comprising a proteasome inhibitor, and then contacting the cells with a composition comprising clofazimine. Examples of contacting the cells with a composition comprising an immunomodulatory drug before contacting the cells with a composition comprising a proteasome inhibitor, and then contacting the cells with a composition comprising clofazimine include, but are not limited to, contacting the cells with a composition comprising an immunomodulatory drug 4 weeks, 3 weeks, 2 weeks, 7 days, 6 days, 5 days, 4 days, 3 days, 2 days, 36 hours, 24 hours, 22 hours, 20 hours, 18 hours, 16 hours, 14 hours, 12 hours, 10 hours, 9 hours, 8 hours, 7 hours, 6 hours, 5 hours, 4 hours, 3 hours, 2.5 hours, 2 hours, 1.5 hours, 1 hour, 50 minutes, 45 minutes, 40 minutes, 35 minutes, 30 minutes, 25 minutes, 20 minutes, 15 minutes, 10 minutes, 5 minutes, 4 minutes, 3 minutes, 2 minutes, 1 minute, and 30 seconds before contacting the cells with a composition comprising a proteasome inhibitor and contacting the cells with a composition comprising clofazimine 4 weeks, 3 weeks, 2 weeks, 7 days, 6 days, 5 days, 4 days, 3 days, 2 days, 36 hours, 24 hours, 22 hours, 20 hours, 18 hours, 16 hours, 14 hours, 12 hours, 10 hours, 9 hours, 8 hours, 7 hours, 6 hours, 5 hours, 4 hours, 3 hours, 2.5 hours, 2 hours, 1.5 hours, 1 hour, 50 minutes, 45 minutes, 40 minutes, 35 minutes, 30 minutes, 25 minutes, 20 minutes, 15 minutes, 10 minutes, 5 minutes, 4 minutes, 3 minutes, 2 minutes, 1 minute, and 30 seconds after contacting the cells with the composition comprising the proteasome inhibitor. In some embodiments, the cells are contacted with a composition comprising an immunomodulatory drug multiple times before the cells are contacted with a composition comprising a proteasome inhibitor. In some embodiments, the cells are contacted with a composition comprising a proteasome inhibitor multiple times before the cells are contacted with a composition comprising clofazimine.

In some embodiments, the method comprises contacting the cells with a composition comprising an immunomodulatory drug before contacting the cells with a composition comprising clofazimine, and then contacting the cells with a composition comprising a proteasome inhibitor. Examples of contacting the cells with a composition comprising an immunomodulatory drug before contacting the cells with a composition comprising clofazimine, and then contacting the cells with a composition comprising a proteasome inhibitor include, but are not limited to, contacting the cells with a composition comprising an immunomodulatory drug 4 weeks, 3 weeks, 2 weeks, 7 days, 6 days, 5 days, 4 days, 3 days, 2 days, 36 hours, 24 hours, 22 hours, 20 hours, 18 hours, 16 hours, 14 hours, 12 hours, 10 hours, 9 hours, 8 hours, 7 hours, 6 hours, 5 hours, 4 hours, 3 hours, 2.5 hours, 2 hours, 1.5 hours, 1 hour, 50 minutes, 45 minutes, 40 minutes, 35 minutes, 30 minutes, 25 minutes, 20 minutes, 15 minutes, 10 minutes, 5 minutes, 4 minutes, 3 minutes, 2 minutes, 1 minute, and 30 seconds before contacting the cells with a composition comprising clofazimine and contacting the cells with a composition comprising a proteasome inhibitor 4 weeks, 3 weeks, 2 weeks, 7 days, 6 days, 5 days, 4 days, 3 days, 2 days, 36 hours, 24 hours, 22 hours, 20 hours, 18 hours, 16 hours, 14 hours, 12 hours, 10 hours, 9 hours, 8 hours, 7 hours, 6 hours, 5 hours, 4 hours, 3 hours, 2.5 hours, 2 hours, 1.5 hours, 1 hour, 50 minutes, 45 minutes, 40 minutes, 35 minutes, 30 minutes, 25 minutes, 20 minutes, 15 minutes, 10 minutes, 5 minutes, 4 minutes, 3 minutes, 2 minutes, 1 minute, and 30 seconds after contacting the cells with the composition comprising clofazimine. In some embodiments, the cells are contacted with a composition comprising an immunomodulatory drug multiple times before the cells are contacted with a composition comprising clofazimine. In some embodiments, the cells are contacted with a composition comprising clofazimine multiple times before the cells are contacted with a composition comprising a proteasome inhibitor.

Methods of Treatment

In various embodiments, the disclosure provides methods of treating cancer in a subject. In some embodiments, the cancer is myeloma, Mantle Cell Lymphoma (MCL), or prostate cancer. In some embodiments, the cancer is myeloma.

In some embodiments, the method comprises administering to the subject a composition of the present invention. In some embodiments, the method comprises administering to the subject a composition comprising clofazimine. In one embodiment, the subject has cancer. In one embodiment, the subject has myeloma.

In certain embodiments, the method comprises administering to the subject, a composition comprising clofazimine in combination with a proteasome inhibitor, and/or an immunomodulatory drug. In certain embodiments, the method comprises administering to the subject, a first composition comprising clofazimine and a second composition comprising a proteasome inhibitor and/or an immunomodulatory drug. The first and second compositions may be administered separately, simultaneously, or sequentially. In certain embodiments, the method comprises administering to the subject, a first composition comprising clofazimine, a second composition comprising a proteasome inhibitor, and a third composition comprising an immunomodulatory drug. The first, second, and third compositions may be administered separately, simultaneously, or sequentially.

In some embodiments, the method further comprises administering to the subject, separately, simultaneously, or sequentially, a composition comprising clofazimine and a composition comprising one or more proteasome inhibitors. In some embodiments, the one or more proteasome inhibitors are one or more selected from the group consisting of bortezomib, carfilzomib, oprozomid, marizomib, delanzomib, and ixazomib. In some embodiments, the proteasome inhibitor is ixazomib.

In some embodiments, the method comprises administering to the subject a composition comprising clofazimine before administering a composition comprising a proteasome inhibitor. Examples of administering a composition comprising clofazimine before administering a composition comprising a proteasome inhibitor include, but are not limited to, administering a composition comprising clofazimine 4 weeks, 3 weeks, 2 weeks, 7 days, 6 days, 5 days, 4 days, 3 days, 2 days, 36 hours, 24 hours, 22 hours, 20 hours, 18 hours, 16 hours, 14 hours, 12 hours, 10 hours, 9 hours, 8 hours, 7 hours, 6 hours, 5 hours, 4 hours, 3 hours, 2.5 hours, 2 hours, 1.5 hours, 1 hour, 50 minutes, 45 minutes, 40 minutes, 35 minutes, 30 minutes, 25 minutes, 20 minutes, 15 minutes, 10 minutes, 5 minutes, 4 minutes, 3 minutes, 2 minutes, 1 minute, and 30 seconds before administering a composition comprising a proteasome inhibitor. In some embodiments, a composition comprising clofazimine is administered to the subject multiple times before a composition comprising a proteasome inhibitor is administered.

In some embodiments, the method comprises administering to the subject a composition comprising clofazimine and a composition comprising a proteasome inhibitor simultaneously.

In some embodiments, the method comprises administering to the subject a composition comprising clofazimine after administering a composition comprising a proteasome inhibitor. Examples of administering a composition comprising clofazimine after administering a composition comprising a proteasome inhibitor include, but are not limited to, administering a composition comprising clofazimine 4 weeks, 3 weeks, 2 weeks, 7 days, 6 days, 5 days, 4 days, 3 days, 2 days, 36 hours, 24 hours, 22 hours, 20 hours, 18 hours, 16 hours, 14 hours, 12 hours, 10 hours, 9 hours, 8 hours, 7 hours, 6 hours, 5 hours, 4 hours, 3 hours, 2.5 hours, 2 hours, 1.5 hours, 1 hour, 50 minutes, 45 minutes, 40 minutes, 35 minutes, 30 minutes, 25 minutes, 20 minutes, 15 minutes, 10 minutes, 5 minutes, 4 minutes, 3 minutes, 2 minutes, 1 minute, and 30 seconds after administering a composition comprising a proteasome inhibitor. In some embodiments, a composition comprising a proteasome inhibitor is administered multiple times before a composition comprising clofazimine is administered.

In some embodiments, the method comprises administering to the subject, separately, simultaneously, or sequentially, a composition comprising clofazimine and a composition comprising one or more immunomodulatory drugs. In some embodiments, the one more immunomodulatory drugs are one or more selected from the group consisting of lenalidomide, pomalidomide, thalidomide, and imiquimod. In some embodiments, the immunomodulatory drug is lenalidomide.

In some embodiments, the method comprises administering to the subject a composition comprising clofazimine before administering a composition comprising an immunomodulatory drug. Examples of administering a composition comprising clofazimine before administering a composition comprising an immunomodulatory drug include, but are not limited to, administering a composition comprising clofazimine 4 weeks, 3 weeks, 2 weeks, 7 days, 6 days, 5 days, 4 days, 3 days, 2 days, 36 hours, 24 hours, 22 hours, 20 hours, 18 hours, 16 hours, 14 hours, 12 hours, 10 hours, 9 hours, 8 hours, 7 hours, 6 hours, 5 hours, 4 hours, 3 hours, 2.5 hours, 2 hours, 1.5 hours, 1 hour, 50 minutes, 45 minutes, 40 minutes, 35 minutes, 30 minutes, 25 minutes, 20 minutes, 15 minutes, 10 minutes, 5 minutes, 4 minutes, 3 minutes, 2 minutes, 1 minute, and 30 seconds before administering a composition comprising an immunomodulatory drug. In some embodiments, a composition comprising clofazimine is administered multiple times before a composition comprising an immunomodulatory drug is administered.

In some embodiments, the method comprises simultaneously administering a composition comprising clofazimine and a composition comprising an immunomodulatory drug.

In some embodiments, the method comprises administering to the subject a composition comprising clofazimine after administering a composition comprising an immunomodulatory drug. Examples of administering a composition comprising clofazimine after administering a composition comprising an immunomodulatory drug include, but are not limited to, administering a composition comprising clofazimine 4 weeks, 3 weeks, 2 weeks, 7 days, 6 days, 5 days, 4 days, 3 days, 2 days, 36 hours, 24 hours, 22 hours, 20 hours, 18 hours, 16 hours, 14 hours, 12 hours, 10 hours, 9 hours, 8 hours, 7 hours, 6 hours, 5 hours, 4 hours, 3 hours, 2.5 hours, 2 hours, 1.5 hours, 1 hour, 50 minutes, 45 minutes, 40 minutes, 35 minutes, 30 minutes, 25 minutes, 20 minutes, 15 minutes, 10 minutes, 5 minutes, 4 minutes, 3 minutes, 2 minutes, 1 minute, and 30 seconds after administering a composition comprising an immunomodulatory drug. In some embodiments, a composition comprising an immunomodulatory drug is administered multiple times before a composition comprising clofazimine is administered.

In some embodiments, the method comprises separately, simultaneously, or sequentially administering to the subject a composition comprising clofazimine, a composition comprising one or more proteasome inhibitors, and a composition comprising one or more immunomodulatory drugs. In some embodiments, the one or more proteasome inhibitors are one or more selected from the group consisting of bortezomib, carfilzomib, oprozomid, marizomib, delanzomib, and ixazomib. In some embodiments, the proteasome inhibitor is ixazomib. In some embodiments, the one more immunomodulatory drugs are one or more selected from the group consisting of lenalidomide, pomalidomide, thalidomide, and imiquimod. In some embodiments, the immunomodulatory drug is lenalidomide. In some embodiments, the proteasome inhibitor is ixazomib and the immunomodulatory drug is lenalidomide.

In some embodiments, the method comprises administering to the subject a composition comprising clofazimine before administering a composition comprising a proteasome inhibitor, and then administering a composition comprising an immunomodulatory drug. Examples of administering a composition comprising clofazimine before administering a composition comprising a proteasome inhibitor, and then administering a composition comprising an immunomodulatory drug include, but are not limited to, administering a composition comprising clofazimine 4 weeks, 3 weeks, 2 weeks, 7 days, 6 days, 5 days, 4 days, 3 days, 2 days, 36 hours, 24 hours, 22 hours, 20 hours, 18 hours, 16 hours, 14 hours, 12 hours, 10 hours, 9 hours, 8 hours, 7 hours, 6 hours, 5 hours, 4 hours, 3 hours, 2.5 hours, 2 hours, 1.5 hours, 1 hour, 50 minutes, 45 minutes, 40 minutes, 35 minutes, 30 minutes, 25 minutes, 20 minutes, 15 minutes, 10 minutes, 5 minutes, 4 minutes, 3 minutes, 2 minutes, 1 minute, and 30 seconds before administering a composition comprising a proteasome inhibitor and administering a composition comprising an immunomodulatory drug 4 weeks, 3 weeks, 2 weeks, 7 days, 6 days, 5 days, 4 days, 3 days, 2 days, 36 hours, 24 hours, 22 hours, 20 hours, 18 hours, 16 hours, 14 hours, 12 hours, 10 hours, 9 hours, 8 hours, 7 hours, 6 hours, 5 hours, 4 hours, 3 hours, 2.5 hours, 2 hours, 1.5 hours, 1 hour, 50 minutes, 45 minutes, 40 minutes, 35 minutes, 30 minutes, 25 minutes, 20 minutes, 15 minutes, 10 minutes, 5 minutes, 4 minutes, 3 minutes, 2 minutes, 1 minute, and 30 seconds after administering the composition comprising the proteasome inhibitor. In some embodiments, a composition comprising clofazimine is administered multiple times before a composition comprising a proteasome inhibitor is administered. In some embodiments, a composition comprising a proteasome inhibitor is administered multiple times before a composition comprising an immunomodulatory drug is administered.

In some embodiments, the method comprises administering to the subject a composition comprising clofazimine before administering a composition comprising an immunomodulatory drug, and then administering a composition comprising a proteasome inhibitor. Examples of administering a composition comprising clofazimine before administering a composition comprising an immunomodulatory drug, and then administering a composition comprising a proteasome inhibitor include, but are not limited to, administering a composition comprising clofazimine 4 weeks, 3 weeks, 2 weeks, 7 days, 6 days, 5 days, 4 days, 3 days, 2 days, 36 hours, 24 hours, 22 hours, 20 hours, 18 hours, 16 hours, 14 hours, 12 hours, 10 hours, 9 hours, 8 hours, 7 hours, 6 hours, 5 hours, 4 hours, 3 hours, 2.5 hours, 2 hours, 1.5 hours, 1 hour, 50 minutes, 45 minutes, 40 minutes, 35 minutes, 30 minutes, 25 minutes, 20 minutes, 15 minutes, 10 minutes, 5 minutes, 4 minutes, 3 minutes, 2 minutes, 1 minute, and 30 seconds before administering a composition comprising an immunomodulatory drug and administering a composition comprising a proteasome inhibitor 4 weeks, 3 weeks, 2 weeks, 7 days, 6 days, 5 days, 4 days, 3 days, 2 days, 36 hours, 24 hours, 22 hours, 20 hours, 18 hours, 16 hours, 14 hours, 12 hours, 10 hours, 9 hours, 8 hours, 7 hours, 6 hours, 5 hours, 4 hours, 3 hours, 2.5 hours, 2 hours, 1.5 hours, 1 hour, 50 minutes, 45 minutes, 40 minutes, 35 minutes, 30 minutes, 25 minutes, 20 minutes, 15 minutes, 10 minutes, 5 minutes, 4 minutes, 3 minutes, 2 minutes, 1 minute, and 30 seconds after administering the composition comprising the immunomodulatory drug. In some embodiments, a composition comprising clofazimine is administered multiple times before a composition comprising an immunomodulatory drug is administered. In some embodiments, a composition comprising an immunomodulatory drug is administered multiple times before a composition comprising a proteasome inhibitor is administered.

In some embodiments, the method comprises administering to the subject a composition comprising a proteasome inhibitor before administering a composition comprising clofazimine, and then administering a composition comprising an immunomodulatory drug. Examples of administering a composition comprising a proteasome inhibitor before administering a composition comprising clofazimine, and then administering a composition comprising an immunomodulatory drug include, but are not limited to, administering a composition comprising a proteasome inhibitor 4 weeks, 3 weeks, 2 weeks, 7 days, 6 days, 5 days, 4 days, 3 days, 2 days, 36 hours, 24 hours, 22 hours, 20 hours, 18 hours, 16 hours, 14 hours, 12 hours, 10 hours, 9 hours, 8 hours, 7 hours, 6 hours, 5 hours, 4 hours, 3 hours, 2.5 hours, 2 hours, 1.5 hours, 1 hour, 50 minutes, 45 minutes, 40 minutes, 35 minutes, 30 minutes, 25 minutes, 20 minutes, 15 minutes, 10 minutes, 5 minutes, 4 minutes, 3 minutes, 2 minutes, 1 minute, and 30 seconds before administering a composition comprising clofazimine and administering a composition comprising an immunomodulatory drug 4 weeks, 3 weeks, 2 weeks, 7 days, 6 days, 5 days, 4 days, 3 days, 2 days, 36 hours, 24 hours, 22 hours, 20 hours, 18 hours, 16 hours, 14 hours, 12 hours, 10 hours, 9 hours, 8 hours, 7 hours, 6 hours, 5 hours, 4 hours, 3 hours, 2.5 hours, 2 hours, 1.5 hours, 1 hour, 50 minutes, 45 minutes, 40 minutes, 35 minutes, 30 minutes, 25 minutes, 20 minutes, 15 minutes, 10 minutes, 5 minutes, 4 minutes, 3 minutes, 2 minutes, 1 minute, and 30 seconds after administering the composition comprising clofazimine. In some embodiments, a composition comprising a proteasome inhibitor is administered multiple times before a composition comprising clofazimine is administered. In some embodiments, a composition comprising clofazimine is administered multiple times before a composition comprising an immunomodulatory drug is administered.

In some embodiments, the method comprises administering to the subject a composition comprising a proteasome inhibitor before administering a composition comprising an immunomodulatory drug, and then administering a composition comprising clofazimine. Examples of administering a composition comprising a proteasome inhibitor before administering a composition comprising an immunomodulatory drug, and then administering a composition comprising clofazimine include, but are not limited to, administering a composition comprising a proteasome inhibitor 4 weeks, 3 weeks, 2 weeks, 7 days, 6 days, 5 days, 4 days, 3 days, 2 days, 36 hours, 24 hours, 22 hours, 20 hours, 18 hours, 16 hours, 14 hours, 12 hours, 10 hours, 9 hours, 8 hours, 7 hours, 6 hours, 5 hours, 4 hours, 3 hours, 2.5 hours, 2 hours, 1.5 hours, 1 hour, 50 minutes, 45 minutes, 40 minutes, 35 minutes, 30 minutes, 25 minutes, 20 minutes, 15 minutes, 10 minutes, 5 minutes, 4 minutes, 3 minutes, 2 minutes, 1 minute, and 30 seconds before administering a composition comprising an immunomodulatory drug and administering a composition comprising clofazimine 4 weeks, 3 weeks, 2 weeks, 7 days, 6 days, 5 days, 4 days, 3 days, 2 days, 36 hours, 24 hours, 22 hours, 20 hours, 18 hours, 16 hours, 14 hours, 12 hours, 10 hours, 9 hours, 8 hours, 7 hours, 6 hours, 5 hours, 4 hours, 3 hours, 2.5 hours, 2 hours, 1.5 hours, 1 hour, 50 minutes, 45 minutes, 40 minutes, 35 minutes, 30 minutes, 25 minutes, 20 minutes, 15 minutes, 10 minutes, 5 minutes, 4 minutes, 3 minutes, 2 minutes, 1 minute, and 30 seconds after administering the composition comprising the immunomodulatory drug. In some embodiments a composition comprising a proteasome inhibitor is administered multiple times before a composition comprising an immunomodulatory drug is administered. In some embodiments, a composition comprising an immunomodulatory drug is administered multiple times before a composition comprising clofazimine is administered.

In some embodiments, the method comprises administering to the subject a composition comprising an immunomodulatory drug before administering a composition comprising a proteasome inhibitor, and then administering a composition comprising clofazimine. Examples of administering a composition comprising an immunomodulatory drug before administering a composition comprising a proteasome inhibitor, and then administering a composition comprising clofazimine include, but are not limited to, administering a composition comprising an immunomodulatory drug 4 weeks, 3 weeks, 2 weeks, 7 days, 6 days, 5 days, 4 days, 3 days, 2 days, 36 hours, 24 hours, 22 hours, 20 hours, 18 hours, 16 hours, 14 hours, 12 hours, 10 hours, 9 hours, 8 hours, 7 hours, 6 hours, 5 hours, 4 hours, 3 hours, 2.5 hours, 2 hours, 1.5 hours, 1 hour, 50 minutes, 45 minutes, 40 minutes, 35 minutes, 30 minutes, 25 minutes, 20 minutes, 15 minutes, 10 minutes, 5 minutes, 4 minutes, 3 minutes, 2 minutes, 1 minute, and 30 seconds before contacting the cells with a composition comprising a proteasome inhibitor and contacting the cells with a composition comprising clofazimine 4 weeks, 3 weeks, 2 weeks, 7 days, 6 days, 5 days, 4 days, 3 days, 2 days, 36 hours, 24 hours, 22 hours, 20 hours, 18 hours, 16 hours, 14 hours, 12 hours, 10 hours, 9 hours, 8 hours, 7 hours, 6 hours, 5 hours, 4 hours, 3 hours, 2.5 hours, 2 hours, 1.5 hours, 1 hour, 50 minutes, 45 minutes, 40 minutes, 35 minutes, 30 minutes, 25 minutes, 20 minutes, 15 minutes, 10 minutes, 5 minutes, 4 minutes, 3 minutes, 2 minutes, 1 minute, and 30 seconds after administering the composition comprising the proteasome inhibitor. In some embodiments, an immunomodulatory drug is administered multiple times before a composition comprising a proteasome inhibitor is administered. In some embodiments, a composition comprising a proteasome inhibitor is administered multiple times before a composition comprising clofazimine is administered.

In some embodiments, the method comprises administering to the subject a composition comprising an immunomodulatory drug before administering a composition comprising clofazimine, and then administering a composition comprising a proteasome inhibitor. Examples of administering a composition comprising an immunomodulatory drug before administering a composition comprising clofazimine, and then administering a composition comprising a proteasome inhibitor include, but are not limited to, administering a composition comprising an immunomodulatory drug 4 weeks, 3 weeks, 2 weeks, 7 days, 6 days, 5 days, 4 days, 3 days, 2 days, 36 hours, 24 hours, 22 hours, 20 hours, 18 hours, 16 hours, 14 hours, 12 hours, 10 hours, 9 hours, 8 hours, 7 hours, 6 hours, 5 hours, 4 hours, 3 hours, 2.5 hours, 2 hours, 1.5 hours, 1 hour, 50 minutes, 45 minutes, 40 minutes, 35 minutes, 30 minutes, 25 minutes, 20 minutes, 15 minutes, 10 minutes, 5 minutes, 4 minutes, 3 minutes, 2 minutes, 1 minute, and 30 seconds before administering a composition comprising clofazimine and administering a composition comprising a proteasome inhibitor 4 weeks, 3 weeks, 2 weeks, 7 days, 6 days, 5 days, 4 days, 3 days, 2 days, 36 hours, 24 hours, 22 hours, 20 hours, 18 hours, 16 hours, 14 hours, 12 hours, 10 hours, 9 hours, 8 hours, 7 hours, 6 hours, 5 hours, 4 hours, 3 hours, 2.5 hours, 2 hours, 1.5 hours, 1 hour, 50 minutes, 45 minutes, 40 minutes, 35 minutes, 30 minutes, 25 minutes, 20 minutes, 15 minutes, 10 minutes, 5 minutes, 4 minutes, 3 minutes, 2 minutes, 1 minute, and 30 seconds after administering the composition comprising clofazimine. In some embodiments, an immunomodulatory drug is administered multiple times before a composition comprising clofazimine is administered. In some embodiments, a composition comprising clofazimine is administered multiple times before a composition comprising a proteasome inhibitor is administered.

In some embodiments, the method is effective for treating cancer that is or has become resistant to one or more proteasome inhibitors and/or one or more immunomodulatory drugs. In some embodiments, administration of a composition comprising clofazimine re-sensitizes a cancer to one or more proteasome inhibitors and/or one or more immunomodulatory drugs.

In one embodiment, the method comprises administering to the subject a composition comprising clofazimine, wherein the subject has previously been treated with a proteasome inhibitor and/or an immunomodulatory drug. In certain embodiments, the cancer of the subject is refractory to treatment with a proteasome inhibitor and/or immunomodulatory drug. In certain embodiments, the method comprises administering to the subject having a cancer that is refractory to treatment with a proteasome inhibitor and/or immunomodulatory drug, a composition comprising clofazimine in combination with a proteasome inhibitor, and/or an immunomodulatory drug. In certain embodiments, the method comprises administering to the subject having a cancer that is refractory to treatment with a proteasome inhibitor and/or immunomodulatory drug, a first composition comprising clofazimine and a second composition comprising a proteasome inhibitor and/or an immunomodulatory drug. The first and second compositions may be administered separately, simultaneously, or sequentially. In certain embodiments, the method comprises administering to the subject having a cancer that is refractory to treatment with a proteasome inhibitor and/or immunomodulatory drug, a first composition comprising clofazimine, a second composition comprising a proteasome inhibitor, and a third composition comprising an immunomodulatory drug. The first, second, and third compositions may be administered separately, simultaneously, or sequentially.

Pharmaceutical Compositions and Formulations

The invention also encompasses the use of pharmaceutical compositions to practice the methods of the invention. Such a pharmaceutical composition may consist of at least one composition of the invention or a salt thereof in a form suitable for administration to a subject, or the pharmaceutical composition may comprise at least one composition of the invention or a salt thereof, and one or more pharmaceutically acceptable carriers, one or more additional ingredients, or some combination of these. The compound or conjugate may be present in the pharmaceutical composition in the form of a physiologically acceptable salt, such as in combination with a physiologically acceptable cation or anion, as is well known in the art.

Pharmaceutical compositions that are useful in the methods of the invention may be suitably developed for oral, rectal, vaginal, parenteral, topical, pulmonary, intranasal, buccal, ophthalmic, or another route of administration. A composition useful within the methods of the invention may be directly administered to the skin, vagina, or any other tissue of a mammal. Other contemplated formulations include liposomal preparations, resealed erythrocytes containing the active ingredient, and immunologically based formulations. The route(s) of administration will be readily apparent to the skilled artisan and will depend upon any number of factors including the type and severity of the disease being treated, the type and age of the veterinary or human subject being treated, and the like.

Although the invention herein is principally directed to the ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist may design and perform such modification with merely ordinary, if any, experimentation. Subjects to which administration of the pharmaceutical compositions is contemplated include, but are not limited to, humans and other primates, mammals including commercially relevant mammals such as cattle, pigs, horses, sheep, cats, and dogs.

In one embodiment, the compositions utilized in the invention are formulated using one or more pharmaceutically acceptable excipients or carriers. In one embodiment, the pharmaceutical compositions comprise a therapeutically effective amount of a compound or conjugate of the invention and a pharmaceutically acceptable carrier. Pharmaceutically acceptable carriers that are useful, include, but are not limited to, glycerol, water, saline, ethanol, and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In one embodiment isotonic agents, for example, sugars, sodium chloride, or polyalcohols such as mannitol and sorbitol, are included in the composition. Prolonged absorption of the injectable compositions may be brought about by including in the composition an agent that delays absorption, for example, aluminum monostearate or gelatin. In one embodiment, the pharmaceutically acceptable carrier is not DMSO alone.

Formulations may be employed in admixtures with conventional excipients, i.e., pharmaceutically acceptable organic or inorganic carrier substances suitable for oral, vaginal, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

As used herein, "additional ingredients" include, but are not limited to, one or more of the following: excipients; surface active agents; dispersing agents; inert diluents;

granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" that may be included in the pharmaceutical compositions of the invention are known in the art and described, for example in Genaro, ed. (1985, Remington's Pharmaceutical Sciences, Mack Publishing Co., Easton, PA), which is incorporated herein by reference.

The composition utilized in the invention may comprise a preservative from about 0.005% to 2.0% by total weight of the composition. The preservative is used to prevent spoilage in the case of exposure to contaminants in the environment. Examples of preservatives useful in accordance with the invention included but are not limited to those selected from the group consisting of benzyl alcohol, sorbic acid, parabens, imidurea and combinations thereof. An exemplary preservative is a combination of about 0.5% to 2.0% benzyl alcohol and 0.05% to 0.5% sorbic acid.

In one embodiment, the composition includes an antioxidant and a chelating agent that inhibits the degradation of the compound. Exemplary antioxidants for some compounds are BHT, BHA, alpha-tocopherol, and ascorbic acid in the range of about 0.01% to 0.3%. In one embodiment, the BHT is in the range of 0.03% to 0.1% by weight by total weight of the composition. In one embodiment, the chelating agent is present in an amount of from 0.01% to 0.5% by weight by total weight of the composition. Exemplary chelating agents include edetate salts (e.g., disodium edetate) and citric acid in the weight range of about 0.01% to 0.20%. In one embodiment, chelating agents may be in the range of 0.02% to 0.10% by weight by total weight of the composition. The chelating agent is useful for chelating metal ions in the composition that may be detrimental to the shelf life of the formulation. While BHT and disodium edetate are the exemplary antioxidant and chelating agent respectively for some compounds, other suitable and equivalent antioxidants and chelating agents may be substituted therefore as would be known to those skilled in the art.

Liquid suspensions may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. As used herein, an "oily" liquid is one which comprises a carbon-containing liquid molecule and which exhibits a less polar character than water. Liquid solutions of the pharmaceutical composition for use in the invention may comprise each of the components described regarding liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the composition utilized in the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition for use in the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

The regimen of administration may affect what constitutes an effective amount. The therapeutic formulations may be administered to the subject either prior to or after a diagnosis of disease. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a subject, such a mammal, including a human, may be carried out using known procedures, at dosages and for periods of time effective to prevent or treat disease. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the subject being treated, and like factors well-known in the medical arts. Dosage regimens may be adjusted to provide the optimum therapeutic response. For example, several divided doses may be administered daily, or the dose may be proportionally reduced as indicated by the exigencies of the therapeutic situation. A non-limiting example of an effective dose range for a therapeutic compound for use in the invention is from about 1 and 5,000 mg/kg of body weight/per day. One of ordinary skill in the art would be able to study the relevant factors and make the determination regarding the effective amount of the therapeutic compound without undue experimentation.

The invention may be practiced as frequently as several times daily, or it may be practiced less frequently, such as once a day, once a week, once every two weeks, once a month, or even less frequently, such as once every several months or even once a year or less. It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on. The frequency of the dose will be readily apparent to the skilled artisan and will depend upon any number of factors, such as, but not limited to, the type and severity of the disease being treated, the type and age of the animal, etc.

Actual dosage levels of the active ingredients in the pharmaceutical compositions of this invention may be varied so as to obtain an amount of the active ingredient that is effective to achieve the desired therapeutic response for a particular subject, composition, and mode of administration, without being toxic to the subject.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a disease in a subject.

In certain embodiments, the composition of the present invention provides for a controlled release of a therapeutic agent. In certain instances, controlled- or sustained-release formulations of a pharmaceutical composition of the invention may be made using conventional technology, using for example proteins equipped with pH sensitive domains or protease-cleavable fragments. In some cases, the dosage forms to be used can be provided as slow or controlled release of one or more active ingredients therein using, for example, hydropropylmethyl cellulose, other polymer matrices, gels, permeable membranes, osmotic systems, multilayer coatings, micro-particles, liposomes, or microspheres or a combination thereof to provide the desired release profile in varying proportions. Suitable controlled-release formulations known to those of ordinary skill in the art, including those described herein, can be readily selected for use with the pharmaceutical compositions of the invention. Thus, single unit dosage forms suitable for oral administration, such as tablets, capsules, gel-caps, lozenges, and caplets, which are adapted for controlled-release are encompassed by the present invention.

Most controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased subject compliance. In addition, controlled-release formulations can be used to affect the time of onset of action or other characteristics, such as blood level of the drug, and thus can affect the occurrence of side effects.

Most controlled-release formulations are designed to initially release an amount of drug that promptly produces the desired therapeutic effect, and gradually and continually release of other amounts of drug to maintain this level of therapeutic effect over an extended period of time. In certain embodiments, the controlled-release formulation of the composition described herein allows for release of a therapeutic agent precisely when the agent is most needed. In another embodiment, the controlled-release formulation of the composition described herein allows for release of a therapeutic agent precisely in conditions in which the therapeutic agent is most active. In order to maintain this constant level of drug in the body, the drug must be released from the dosage form at a rate that will replace the amount of drug being metabolized and excreted from the body.

In certain embodiments, the composition provides for an environment-dependent release, when and where the therapeutic agent is triggered for release. For example, in certain embodiments the composition invention releases at least one therapeutic agent when and where the at least one therapeutic agent is needed. The triggering of release may be accomplished by a variety of factors within the microenvironment of the treatment or prevention site, including, but not limited to, temperature, pH, the presence or activity of a specific molecule or biomolecule, and the like.

Controlled release of an active ingredient can be stimulated by various inducers, for example pH, temperature, enzymes, water or other physiological conditions or compounds. The term "controlled-release component" in the context of the present invention is defined herein as a compound or compounds, including, but not limited to, polymers, polymer matrices, gels, permeable membranes, liposomes, or microspheres or a combination thereof that facilitates the controlled-release of the active ingredient.

In certain embodiments, the formulations of the present invention may be, but are not limited to, short-term, rapid offset, as well as controlled, for example, sustained release, delayed release, and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release that is longer that the same amount of agent administered in bolus form.

For sustained release, the compounds may be formulated with a suitable polymer or hydrophobic material that provides sustained release properties to the compounds. As such, the compounds for use the method of the invention may be administered in the form of microparticles, for example, by injection or in the form of wafers or discs by implantation.

In one embodiment of the invention, the compositions are administered to a subject, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

In one embodiment, the invention is practiced in dosages that range from one to five times per day or more. In another embodiment, the invention is practiced in range of dosages that include, but are not limited to, once every day, every two, days, every three days to once a week, and once every two weeks. It will be readily apparent to one skilled in the art that the frequency of administration of the various combination compositions of the invention will vary from subject to subject depending on many factors including, but not limited to, age, disease or disorder to be treated, gender, overall health, and other factors. Thus, the invention should not be construed to be limited to any particular dosage regime and the precise dosage and composition to be administered to any subject will be determined by the attending physical taking all other factors about the subject into account.

Routes of administration of include oral, nasal, rectal, parenteral, sublingual, transdermal, transmucosal (e.g., sublingual, lingual, (trans)buccal, (trans)urethral, vaginal (e.g., trans- and perivaginally), (intra)nasal, and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions, and formulations for intravesical administration and the like. It should be understood that the formulations and compositions that would be useful in the present invention are not limited to the particular formulations and compositions that are described herein.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore are not to be construed as limiting in any way the remainder of the disclosure.

Example 1

Novel Pathways Associated with Clofazimine Sensitivity in PI- and IMiD-Resistant Myeloma Multiple myeloma (MM) is an incurable plasma cell malignancy with dose-limiting toxicities and inter-individual variation in response/resistance to the standard-of-care/primary drugs, proteasome inhibitors (PIs), and immunomodulatory derivatives (IMiDs). Although newer therapeutic options are potentially highly efficacious, their costs outweigh the effectiveness. Previously, it has been established that clofazimine (CLF), which activates peroxisome proliferator-activated receptor-γ, synergizes with primary therapies, and targets cancer stem-like cells (CSCs) in drug-resistant chronic myeloid leukemia (C ML) patients.

Experiments were done using a panel of human myeloma cell lines as in vitro model systems representing drug-sensitive, innate/refractory, and clonally-derived acquired/relapsed PI- and cereblon (CRBN)-negative IMiD-resistant myeloma and bone marrow-derived CD138+ primary myeloma cells obtained from patients as ex vivo models to demonstrate that CLF shows significant cytotoxicity against drug-resistant myeloma as single-agent and in combination with PIs and IMiDs. Next, using genome-wide transcriptome analysis (RNA-sequencing), single-cell proteomics (CyTOF; Cytometry by time-of-flight), and Ingenuity Pathway Analysis (IPA), novel pathways associated with CLF efficacy were identified, including induction of ER stress, autophagy, mitochondrial dysfunction, oxidative phosphorylation, enhancement of downstream cascade of p65-NFkB-IRF4-Myc downregulation, and ROS-dependent apoptotic cell death in myeloma.

Further, experiments also showed that CLF erodes quiescent stem-cell populations (CD34+CD38−, CFSE-bright) in drug-resistant C ML patients (Kumar et al., 2019, Haematologica., 105:971-86), as well as quiescent/dormant cells, ALDH+ cells, and Side Populations (SPs), collectively referred to as putative stem-like cells in myeloma, with treatment-refractory phenotypes (Matsui et al., 2004, Blood., 103:2332-2336) (Matsui et al., 2008, Cancer Res., 68:190-197) (Huff et al., 2008, J Clin Oncol., 26:2895-2900) (Guo et al., 2021, Cancers (Basel)., 13:3523).

The materials and methods used in these experiments are now described.

Human Myeloma Cell Lines (HMCLs)

A large panel of HMCLs representing innate sensitivity and resistance to PIs and IMiDs (similar to refractory disease) have been compiled, as well as >10 pairs of parental and clonally-derived PI/IMiD-resistant HMCLs (P vs R pairs; generated using dose escalation over a period of time) representing acquired or emerging drug resistance, and encompassing the broad spectrum of biological and genetic heterogeneity of myeloma (Mitra et al., 2017, Blood Cancer J., 7:e581). The human myeloma cell lines (HMCLs) were obtained as previously described (Mitra et al., 2017, Blood Cancer J., 7:e581). The clonally related acquired PI-resistant HMCLs were generated from parental cell lines by dose escalation of bortezomib using pulses of once-weekly bortezomib treatment as described previously (Mitra et al., 2016, Leukemia., 30:1094-1102). These HMCLs were used as in vitro model systems to screen and re-purpose drugs for the management of PI-resistant myeloma.

It was also found that in vitro drug responses of the four PIs (Bz, Cz, Opz, and Ix) were highly correlated in HMCLs (Mitra et al., 2017, Blood Cancer J., 7:e581). Therefore, ixazomib, a second-generation PI, was used as a representative PI for further studies.

The lenalidomide (IMiD)-resistant cell line, MM1SLenR, was obtained. The cell lines were authenticated at source and tested randomly at regular intervals for mycoplasma negativity. HMCLs were maintained in HMCL media supplemented with IL-6 (Mitra et al., 2020, Blood Cancer J., 10:78).

Patient Primary Myeloma Cells (PMCs)

Bone marrow-derived CD138+ primary myeloma cells were obtained from patients (n=16) and used as ex vivo model systems. Written informed consent was received from participants prior to inclusion in the study. Participants have been identified by number, not by name. The primary samples were cultured as total bone marrow and put in culture to retain the patients' natural BM microenvironment. Cells of interest were CD138+-gated during analysis.

Drugs and Reagents

Drugs, reagents, antibodies, and kits are listed in the table below. All the drugs were dissolved in dimethyl sulfoxide (DMSO) and stored at −20° C.

TABLE 1

| | Antibody/Kits | Manufacturer |
|---|---|---|
| Drugs | Clofazimine (CLF) | Sigma-Aldrich (St Louis, MO) |
| | (±)-Verapamil hydrochloride | Sigma-Aldrich (St Louis, MO) |
| | Ixazomib (Ixa) | Takeda Pharmaceuticals Inc., Deerfield, IL, USA |
| | Bortezomib (Btz) | Takeda Pharmaceuticals Inc., Deerfield, IL, USA |
| | Carfilzomib (Cfz) | Amgen |
| | Oprozomib (Opz) | Amgen |
| | Lenalidomide | Selleck Chemicals |
| Reagents/Kits | MethoCult ™ H4434 Classic/ Methylcellulose-based medium with recombinant cytokines | Stem cell Technologies |
| | FITC Annexin V Apoptosis Detection Kit | BD bioscience |
| | Vybrant ™ DyeCycle ™ Violet Stain | Thermo Fisher Scientific |
| | CellTrace ™ CFSE Cell Proliferation Kit | Thermo Fisher Scientific |
| | Aldefluor ™ Kit | Stem cell Technologies |
| | Caspase-Glo ® 3/7 Assay System | Promega |
| | CellTiter-Glo 2.0 | Promega |
| | Assay ',7'-Dichlorofluorescein diacetate | Sigma-Aldrich (St Louis, MO) |
| Antibodies | GRP-78 | Cell signaling Technology (CST) |
| | phospho-PERK (Thr980) (16F8) | Cell signaling Technology (CST) |
| | Total-PERK | Cell signaling Technology (CST) |
| | Phospho-eIF2α (Ser51) | Cell signaling Technology (CST) |
| | Total-eif2α | Cell signaling Technology (CST) |
| | CHOP | Cell signaling Technology (CST) |
| | IRE-1 | Cell signaling Technology (CST) |
| | ATF-4 | Cell signaling Technology (CST) |

TABLE 1-continued

| | Antibody/Kits | Manufacturer |
|---|---|---|
| | ATF-6 | Cell signaling Technology (CST) |
| | NRF2 (DIZ9C) XP(R) | Cell signaling Technology (CST) |
| | Cleaved caspase-3 | Cell signaling Technology (CST) |
| | Cleaved caspase-8 | Cell signaling Technology (CST) |
| | Cleaved caspase-9 | Cell signaling Technology (CST) |
| | Cleaved PARP | Cell signaling Technology (CST) |
| | Bax | Cell signaling Technology (CST) |
| | BCL2 | Cell signaling Technology (CST) |
| | Survivin | Cell signaling Technology (CST) |
| | MCL-1 | Cell signaling Technology (CST) |
| | LCIIA/B | Cell signaling Technology (CST) |
| | Beclin-1 | Cell signaling Technology (CST) |
| | Atg12 | Cell signaling Technology (CST) |
| | HSP70 | Cell signaling Technology (CST) |
| | HSP90 | Cell signaling Technology (CST) |
| | β-catenin | Cell signaling Technology (CST) |
| | c-Myc | Cell signaling Technology (CST) |
| | p65 | Cell signaling Technology (CST) |
| | IRF4 | Cell signaling Technology (CST) |
| | PRDX1 | Cell signaling Technology (CST) |
| | CyclinD1 | Cell signaling Technology (CST) |
| | Monoclonal Anti-β-Actin-Peroxidase (Mouse) | Sigma-Aldrich (St Louis, MO) |
| | Goat anti-Mouse/Rabbit IgG (H + L) Secondary antibody (HRP conjugated) | Thermo Fisher Scientific |
| | APC anti-mouse CD138 (Syndecan-1) | Bio-legend |
| | APC Rat IgG2a, κ Isotype Ctrl ab | Bio-legend |
| CyTOF reagents | Benzonase | Millipore Sigma |
| | Cell-ID Cisplatin | Fluidigm |
| | Maxpar Fix I Buffer | Fluidigm |
| | Veri-Cells ™ PBMC | BioLegend |
| | Maxpar Cell Staining Buffer | Fluidigm |
| | Formaldehyde solution | Thermo Scientific |
| | Cell-ID ™ Intercalator-Ir | Fluidigm |
| | Maxpar Fix and Perm Buffer | Fluidigm |
| | Maxpar Cell Acquisition Solution | Fluidigm |
| | Cell-ID 20-Plex Pd Barcoding Kit | Fluidigm |

In Vitro Chemosensitivity Assays and Drug Synergy Analysis

HMCLs were treated with increasing concentrations of CLF, PIs (represented by Ix), and IMiDs (represented by Len) as single agents or in combination for 48 h, and cytotoxicity assays were performed using CellTiter-Glo® Luminescent cell viability assay (Promega Madison, WI). Luminescence was recorded in a Neo2 Microplate Reader (Biotek), and half-maximal inhibitory concentration (IC50) values were determined by calculating the nonlinear regression using the sigmoidal dose-response equation (variable slope). The drug cytotoxicity data and IC50 values were used to compare response and to determine synergy by Calcusyn software (Biosoft; Chou-Talalay's CI theorem) (Chou, 2011, Am J Cancer Res, 1: 925-54). CI value <0.9 denotes synergism.

Apoptosis Assays

Cells were cultured for 48 h in the presence of indicated concentrations of compounds, harvested and washed, and incubated with Annexin V-FITC (BD Biosciences) and Propidium Iodide for 15 min at room temperature in the dark. Apoptosis was measured by BD LSR II flow cytometry (BD Biosciences).

Caspase-3/7 activity assays were performed on the HMCLs using Caspase-Glo 3/7 luminescent assay kit according to manufacturer's instructions (Promega Madison, WI). Briefly, $1\times10^6$ cells/ml were cultured in 6-well plates and treated with either CLF alone and/or combination for indicated times. After harvesting, cells were washed twice with cold PBS and resuspended with Caspase-Glo 3/7 reagents. Reactions were incubated for 1 h at 37° C., and luminescence was determined using Synergy 2 Microplate Reader (Biotek). Cell death by apoptosis was also measured by immunoblotting analysis.

Cell Cycle Analysis

HMCLs were seeded in 6-well plates and incubated for 48 h following treatment with 10 μM CLF. Cells were then harvested, washed, and incubated with Propidium Iodide for 30 min at room temperature. Cell cycle progression was measured using a BD LSR II flow cytometer (BD Biosciences). Flow cytometry data analysis was performed using FlowJo software (BD Biosciences).

Colony-Forming Cells (CFCs) Assay

Colony formation potential of untreated and drug-treated HMCLs was accessed using Methylcellulose-based assay according to manufacturer's instructions (Methocult, Stem Cell Technologies). Briefly, myeloma cells were treated with either CLF alone or in combination with PI for the indicated time period. Following incubation, cells were harvested, washed with PBS, and methylcellulose-based media (Methocult) was added to cells pellets, and colonies were allowed to grow for 4 weeks in 6-well plates. Images were captured after 4 weeks with an inverted microscope (Olympus, 4×/20× lens with color camera), and cell colony numbers were counted by Image J software (NIH).

Aldefluor™ Activity Assay

Aldehyde dehydrogenase (ALDH) activity was assessed using the Aldefluor™ assay kit according to the manufacturer's instructions (Stem Cell Technologies). Briefly, $1\times10^6$ myeloma cells were treated with CLF-based regimens for 24 h, harvested, and resuspended in 1 ml Aldefluor™ assay buffer containing the ALDH substrate BODIPY-aminoacetaldehyde (BAAA). Negative control samples were treated with 5 µl of diethylaminobenzaldehyde (DEAB) as an inhibitor of ALDH1 enzymatic activity. Cells were incubated for 30-45 min at 37° C., then washed twice, and suspended in Aldefluor™ assay buffer. The brightly fluorescent ALDH+ cells were detected by BD LSR II flowcytometry.

Carboxyfluorescein Succinimidyl Ester (CFSE) Assay

For assessing apoptosis in quiescent CD138+ cells, myeloma cells were first stained with carboxyfluorescein succinimidyl ester (CFSE; Invitrogen) for 30 min, then washed and resuspended in RPMI1640 medium and were incubated at 37° C. overnight. The next day, cells were treated and maintained further for 4 days with supplementation of the drugs every 48 h. Cells were then harvested, washed, and were labeled with CD138-APC and Annexin/V-FITC antibodies and then gated into non-dividing (CD138+CFSEbright) and dividing (CD138+CFSEdim) cell populations based on CFSE fluorescence intensity using a flow cytometer. Cells cultured in the presence of colchicine (100 ng/ml; Sigma) were used to assess the range of CFSE fluorescence exhibited by cells that were undivided at the end of the culture time.

Side Population Analysis

Side population cells were investigated using DyeCycle™ Violet (cell-permeable DNA binding) assays according to manufacturer's instructions (Thermofisher). Briefly, $1\times10^6$ cells/ml were cultured in 6-well plates and treated with either CLF alone and/or combination for indicated times. After 96 h, cells were stained with 10 µM Vybrant™ DyeCycle™ Violet (DCV; Molecular Probes, Eugene, OR) for 90 min at 37° C. Samples incubated with 100 µM verapamil (Sigma-Aldrich) for 30 min were used as positive control. Following dye incubation, cells were washed twice with ice-cold PBS, chilled on ice, and immediately analyzed by flow cytometry.

Determination of Total Cellular Reactive Oxygen Species (ROS)

Cells were treated with CLF-based regiments for 24 hr. After 24 h, cells were incubated with 10 µM DCFDA in RPMI (Phenol red-free) medium at 37° C. for 30 min, washed twice with phosphate buffer saline (PBS), and ROS production was measured using Synergy 2 Microplate Reader (Biotek).

Measurement of Superoxide Levels

Myeloma cells treated with CLF-based regimens for 24 h were incubated with 2.5 µM DHE (in RPMI) for 15 min in the dark at 37° C. Cells were then washed once with PBS, and red fluorescence was detected by flow cytometry.

Mitochondrial Membrane Potential (MMP) Measurement

CLF-treated (24 h) cells were incubated with 5 µM JC-1 dye for 15 min in the dark at 37° C. and washed twice in PBS, and then analyzed for red and green fluorescence by flow cytometry.

Gene Expression Profiling (GEP) Analysis

Cells were plated at a density of $4\times10^5$ cell/ml and were treated with either CLF alone, Ixa alone, or combination. Twenty-four hours after incubation, high-quality RNA was isolated using QIAshredder and RNeasy® mini kit (Qiagen). RNA concentration and integrity were determined using the Nanodrop-8000 and Agilent 2100 Bioanalyzer and stored at −80° C. RNA integrity number (RIN) threshold of 8 was used for RNA-seq analysis. RNA-seq libraries were constructed using Illumina TruSeq® RNA sample preparation kit v2. Libraries were then size-selected to generate inserts of ~200 bp. Next-generation RNA sequencing was performed on Illumina's NovaSeq platform using 150 bp paired-end protocol with a depth of >20 million reads-per-sample.

RNAseq Data Analysis

Gene expression data was pre-processed, filtered (genes with mean counts <10 were removed), and GEP (CPM—counts per million) data was analyzed further using Partek Flow package to perform differential expression testing to identify GEP signatures. LS (least squares) mean values were calculated for each group as the linear combination or sum of the estimated means from the linear model. LS mean is model-dependent and produces more accurate, unbiased estimate of the group means even in unbalanced data. An LS Mean threshold of ≥1 for downstream analysis was used. Gene Specific Analysis (GSA) was used to perform differential gene expression analysis between groups that applies limma, an empirical Bayesian method, to detect the differentially expressed (DE) genes. The advantage of limma compared to traditional t-test is that limma provides a moderated t-test statistic by shrinking the variance statistics, therefore, improving the statistical power. Mean fold-change>|1| and $p<0.05$ was considered as threshold for reporting significant differential gene expression. Heatmaps were generated using unsupervised hierarchical clustering (HC) analysis based on the top DE genes (DEGs).

Ingenuity PathwayAanalysis (IPA) software was used to identify, i) the most significantly affected molecular pathways, ii) upstream regulator molecules like microRNA and transcription factors, iii) downstream effects and biological processes, and iv) causal networks predicted to be activated or inhibited in response to treatment based on the most significant DE genes (Krämer et al., 2014, Bioinformatics., 30:523-30).

Single-Cell Proteomics

Mass cytometry (CyTOF) analysis is a single-cell proteomics methodology that combines flow cytometry and elemental mass spectrometry. Thirty-seven antibody targets directed against cell surface (neoplastic myeloma) and intracellular markers (immune tumor microenvironment) were utilized for immunophenotyping panels. The antibody markers and respective metal conjugates are described in Table 2. One to three million untreated or treated (for 24 h) HMCLs or primary human myeloma cells were used for CyTOF staining. Cells were stained with cisplatin (1:10,000 dilutions in RPMI1640 media without FBS) at 37° C. for 5 minutes, washed with media with 10% FBS, spun at 300×g, and incubated with media with 10% FBS for 15 min. This was followed by another wash, spin, and the pellet was resuspended in 1× Fix buffer for 10 minutes at room temperature. HMCL samples, along with lyophilized healthy human PBMC (Veri-Cells PBMC: control cells; BioLegend), were washed using Maxpar cell staining buffer (MCSB) (Fluidigm). A total of 16 µL of the surface antibody cocktail was added to each tube containing each cell suspension in 100 µL of MCSB and incubated for 30 minutes at room temperature. Cells were washed with MCSB to remove excess antibodies and stored overnight at −80° C. after methanol fixation. Cells were washed with MCSB and incubated with 20 μL of intracellular antibody cocktail for 30 minutes at room temperature, followed by wash and fixation with fresh 1.6% formaldehyde solution for 10 minutes at room temperature. Cells were washed with MCSB and resuspended in 1 ml of Cell-ID™ Intercalator solution (1:4000 dilution in permeabilization buffer, Maxper Fix, and Perm Buffer). All samples were barcoded using cell-ID™ 20-Plex Barcoding Kit (Fluidigm), which were then stained, washed with MSCB, and acquired as a single multiplexed sample using Maxpar Cell Acquisition solution contained calibration beads.

Samples were loaded onto a Helios CyTOF system (Fluidigm) using an attached autosampler and were acquired at a rate of 200-400 events per second. Data were collected as .FCS files using the CyTOF Software (Version 6.7.1014, Fluidigm). After acquisition, intrafile signal drift was normalized to the acquired calibration bead signal using the CyTOF Software.

TABLE 2

Cell surface and intracellular targets for CyTOF analysis

| SN. | A. Cell surface targets | Metal Tag | Source/ Manufacturer | Catalog No. |
|---|---|---|---|---|
| 1. | CD45 | 89Y | Fluidigm | 3089003B |
| 2. | CD38 | 114Nd | Fluidigm | 3144014B |
| 3. | CD138 | 168Er | Fluidigm | 3168009B |
| 4. | CD3 | 141Pr | Fluidigm | 3141019B |
| 5. | CD56 | 149Sm | Fluidigm | 3149021B |
| 6. | CD19 | 169Tm | Fluidigm | 3169011B |
| 7. | CD81 | 145Nd | Fluidigm | 3145007B |
| 8. | CD20 | 147Sm | Fluidigm | 3147001B |
| 9. | CD34 | 148Nd | Fluidigm | 3148001B |
| 10. | CD274 | 159Tb | Fluidigm | 3159029B |
| 11. | CD27 | 167Er | Fluidigm | 3167006B |
| 12. | CD229 | 174Yb | Fluidigm | 3174017B |
| 13. | CD16 | 209Bi | Fluidigm | 3209002B |
| 14. | CD86 | 150Nd | Fluidigm | 3150020B |
| 15. | CD117* | 173Yb | BioLegend | 313223 |
| 16. | CD28* | 154Sm | BioLegend | 302937 |
| 17. | CD147* | 161Dy | BioLegend | 306206 |
| 18. | CD71* | 170Er | BioLegend | 334102 |
| **SN.** | **B. Intracellular targets** | **Metal Tag** | **Source/ Manufacturer** | **Catalog No.** |
| 1. | 1kBα | 164Dy | Fluidigm | 3164004A |
| 2. | pERK 1/2 [T202/Y204] | 171Yb | Fluidigm | 3171010A |
| 3. | pStat3 [Y705] | 158Gd | Fluidigm | 3158005A |
| 4. | IRF4 | 155Gd | Fluidigm | 3155014B |
| 5. | IKZF1 | 143Nd | Fluidigm | 3143024B |
| 6. | Ki-67 | 172Yb | Fluidigm | 3172024B |
| 7. | pS6 [S235/S236] | 175Lu | Fluidigm | 3175009A |
| 8. | MCL 1 | 163Dy | Fluidigm | 3163006A |
| 9. | Caspase 3/Cleaved | 142Nd | Fluidigm | 3142004A |
| 10. | pAkt [S473] | 152Sm | Fluidigm | 3152005A |
| 11. | p38 [T180/Y182] | 156Gd | Fluidigm | 3156002A |
| 12. | pRb [S807/811] | 166Er | Fluidigm | 3166011A |
| 13. | pCREB [S133] | 165Ho | Fluidigm | 3165009A |
| 14. | IKZF3 | 162Dy | Fluidigm | 3162032B |
| 15. | c-Myc | 176Yb | Fluidigm | 3176012B |
| 16. | Ig kappa/light chain | 160Gd | Fluidigm | 3160005B |
| 17. | Ig lambda/light chain | 151Eu | Fluidigm | 3151004B |
| 18. | BCL-2* | 153Eu | BioLegend | 658702 |
| 19. | Cyclin D1* | 146Nd | Santa Cruz Biotechnology | SC-8396 |

*In-house conjugated antibodies using the X8 polymer MaxPAR antibody conjugation kit (Fluidigm) as per manufacturer's instructions.

CyTOF Data Analysis

For CyTOF data analysis, Cytobank software version 7.3.0 (Santa Clara, CA) was used for cleanup of cell debris, removal of doublets and dead cells, and analysis of cleaned fcs files. Clustering, dimensionality reduction (to 10,000 events per file), and the visualization of cell population cluster map were performed by t-SNE. Relative marker intensities and cluster abundances per sample were visualized by a heatmap.

Western Blotting

Cells treated with CLF, PI, or IMiD as single-agent or as a combination for 24 h were harvested, washed, and lysed using radioimmunoprecipitation assay (RIPA) lysis buffer containing 50 mM Tris-HCl, pH 7.5, 150 mM NaCl, 1% NP40, 5 mM EDTA, 1 mM DTT, phosphatase and proteasome inhibitors cocktail (Sigma), and incubated on ice for 15 min. Samples were then centrifuged at 14,000 rpm at 4° C. for 30 mins. The supernatant was then aspirated, total protein was isolated and quantified using Pierce BCA Protein Assay Kit (Thermo Scientific). Samples were solubilized in SDS-PAGE sample buffer, and equal amounts of protein were loaded per lane of 10% SDS polyacrylamide gels and transferred onto PVDF membranes (Millipore; Billerica, MA). Membranes were blocked in TBS with SuperBlock® blocking buffer (Thermo Fisher). Membranes were then incubated with primary antibodies and secondary antibodies in TBS with 0.2% Tween® 20 and 2.5% BSA. Immunoreactivity was detected by Chemiluminescent HRP Substrate (Bio-Rad), and the exposed image was captured using a ChemiDoc MP Imaging System (Bio-Rad). Densitometry analysis was performed (in triplicates) using Image J software.

Quantitative Reverse Transcriptase Polymerase Chain Reaction (qRT-PCR)

Total RNA isolation from untreated HMCLs and quantification were performed using QIAshredder and RNeasy® mini kit (Qiagen). RNA concentration was determined using the Nanodrop-8000 spectrophotometer, and cDNA was prepared using QuantiTect® Reverse Transcription kit (Qiagen). Following reverse transcription, TaqMan® gene expression assay was performed using AHR mRNA specific TaqMan® primers (TaqMan® Real-Time PCR Assays) and TaqMan® Fast Advanced Master Mix in CFX96 Touch Real-Time PCR Detection System (Bio-Rad, Hercules, CA). Relative AHR expression in the myeloma lines was calculated using the ΔCt method following normalization with Beta-Actin expression (housekeeping gene).

Ex Vivo Direct-to-Drug Screening Assay

The drugs were screened in a 7-point, 10-fold dilution, with the highest concentration at 10 μM, and incubated for 24 h. Anti-MM activity was assessed through cellular viability, evaluated with CellTiter-Glo®. The mid-point EC50, percentage of maximum inhibition was calculated using the TIBCO Spotfire® v.7.0.0 software, and the area under the curve (AUC) was calculated with the GraphPad Prism v.8 software (Bonolo de Campos et al., 2020, Blood Cancer J., 10:54). This data was compared to in vitro response profiles and linked through integrated analyses to CyTOF profiles and multi-omics outcomes.

Statistical Analysis

All statistical analyses were performed using R and GraphPad Prism. All tests were two-sided, and $p<0.05$ was considered statistically significant.

The results of the experiments are now described.

CLF Induces Loss of Viability in HMCLs and PMCs

First, the single-agent in vitro cytotoxicity of CLF for anti-myeloma activity in the HMCL panel were evaluated, representing wide variation in PI and IMiD responses (IC50) (FIG. 1A). It was found that CLF alone showed very potent inhibition of cell viability in HMCLs representing sensitive as well as innate and clonally-derived resistant HMCLs. The single-agent IC50 (48 h) values of CLF were between 0.2-20.5 μM. Next, the link between CLF IC50 of the myeloma cell lines and MM molecular/cytogenetic abnormalities were compared (Mitra A K et al., 2020, Blood Cancer J., 10:78.). These results showed no significant association of CLF response with cytogenetic abnormalities (data not shown).

Figure 1B:
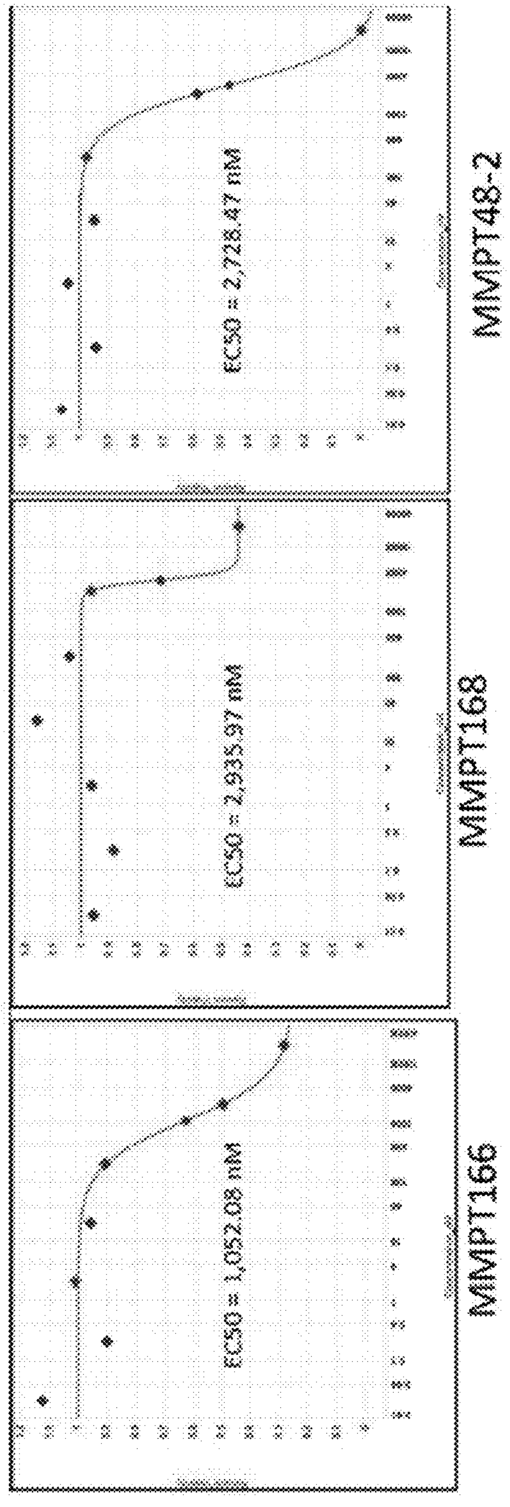

Further, bone marrow-derived CD138-positive PMCs were obtained from patients (n=12) and were used as ex vivo model systems. Using an established direct-to-drug screening assay, each patient's tumor was screened in a Phase 0 assay for drug sensitivity to single-agent CLF (Bonolo et al., 2020, Blood Cancer J., 10:54). The ex vivo CLF EC50 values (1-15 μM; minimum EC50 1052.1 nM, maximum EC50 15210 nM, median EC50 2408.7 nM) were within the in vitro IC50 range. FIG. 1B shows representative CLF single-agent ex vivo cytotoxicity plots in myeloma patients.

CLF Shows Synergy With Proteasome Inhibitors and IMiDs

Figure 2A:
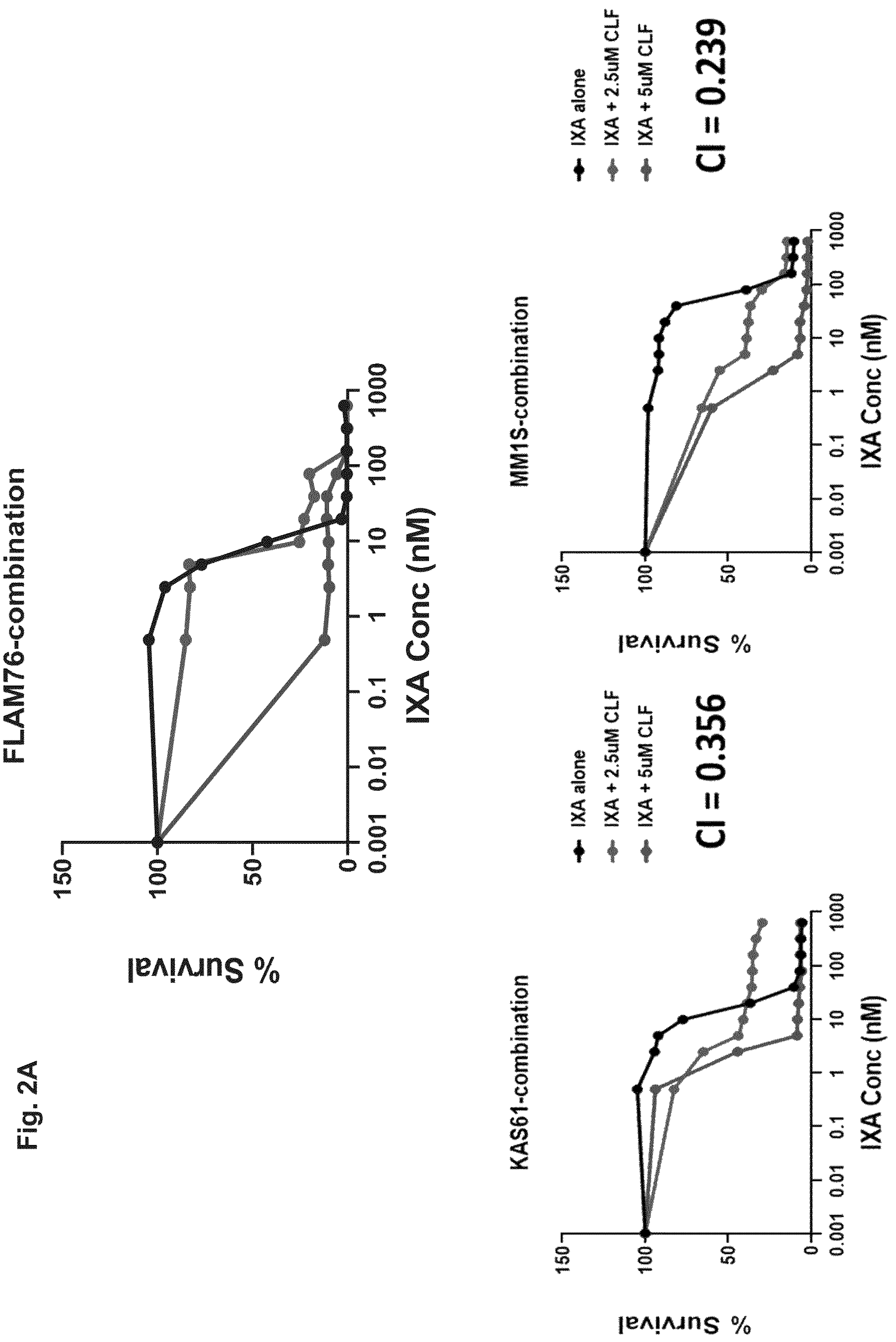
FIG. 2A through FIG. 2D depict representative results from experiments demonstrating clofazimine synergy with proteasome inhibitors (PI) and immunomodulatory drugs (IMiDs) in multiple myeloma.
Figure 2B:
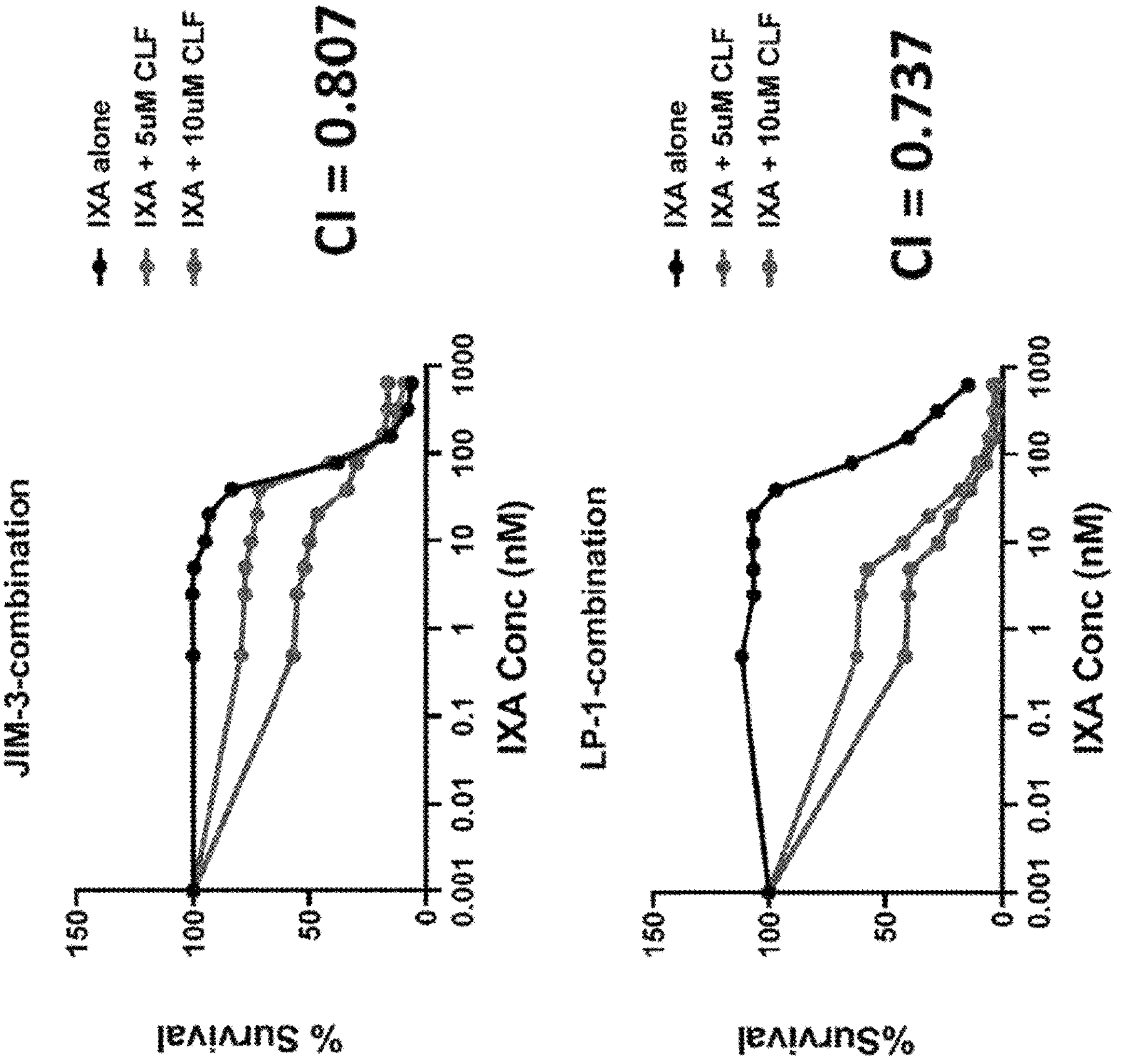
Figure 2C:
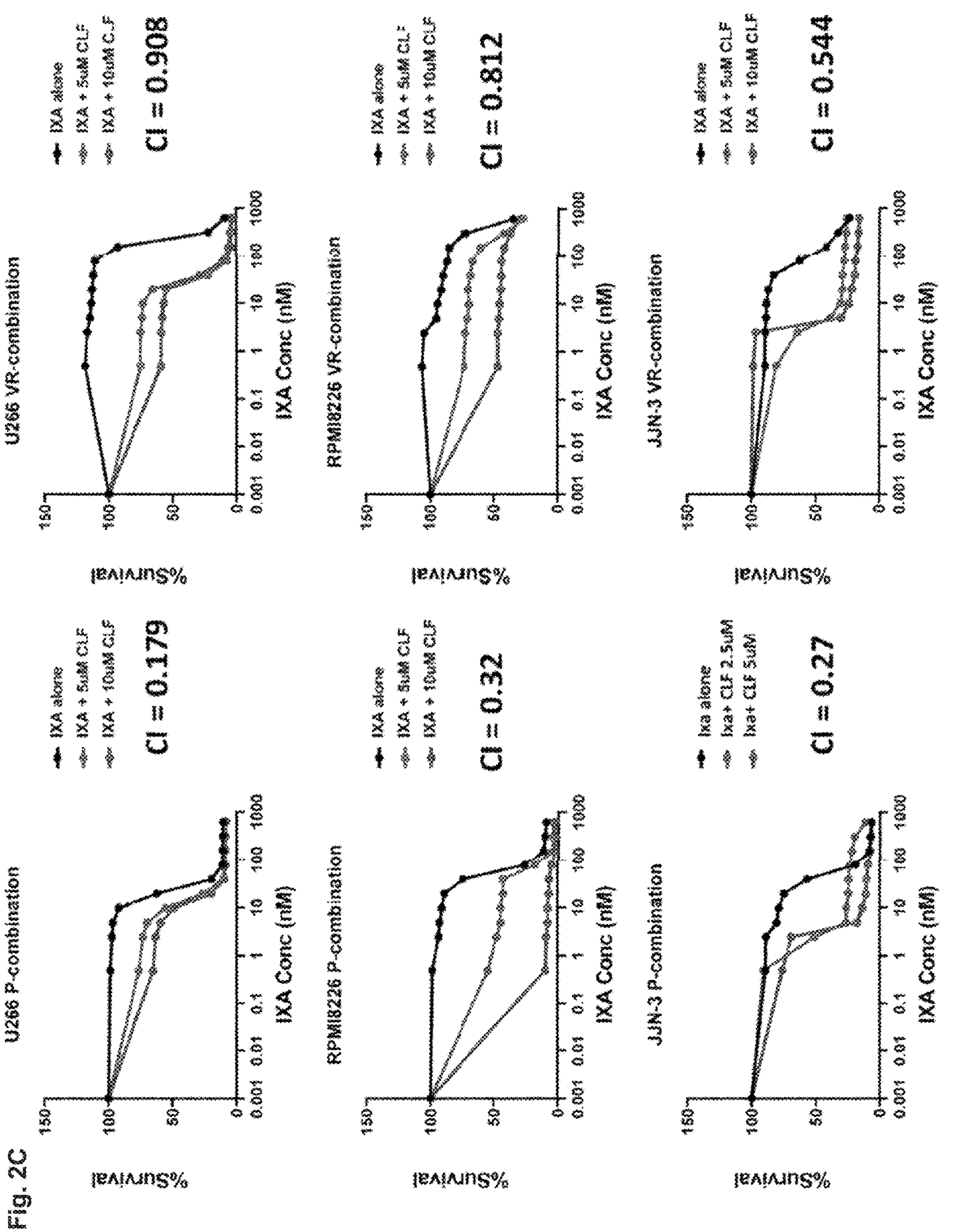
Figure 2D:
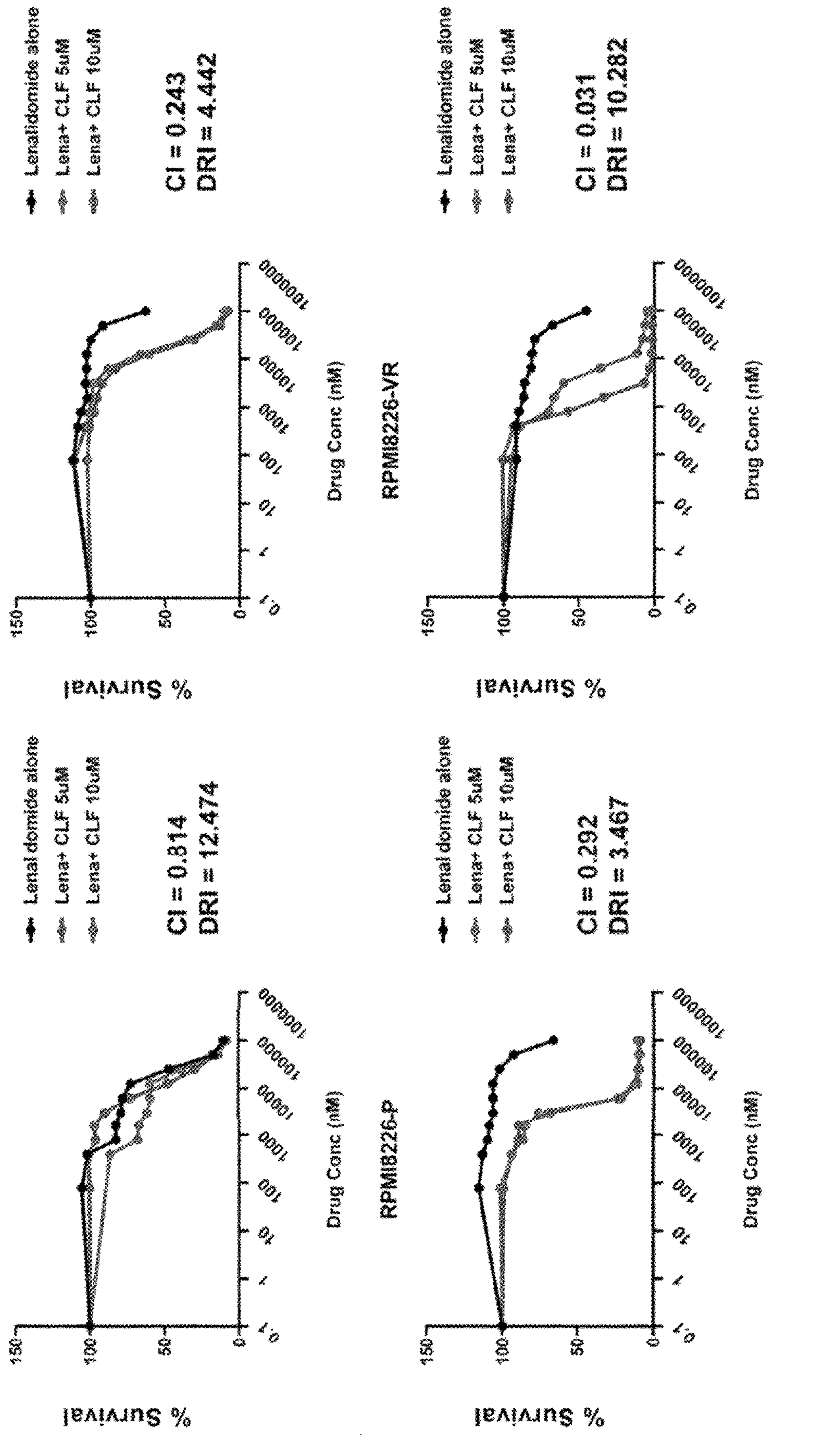
Figure 9B:
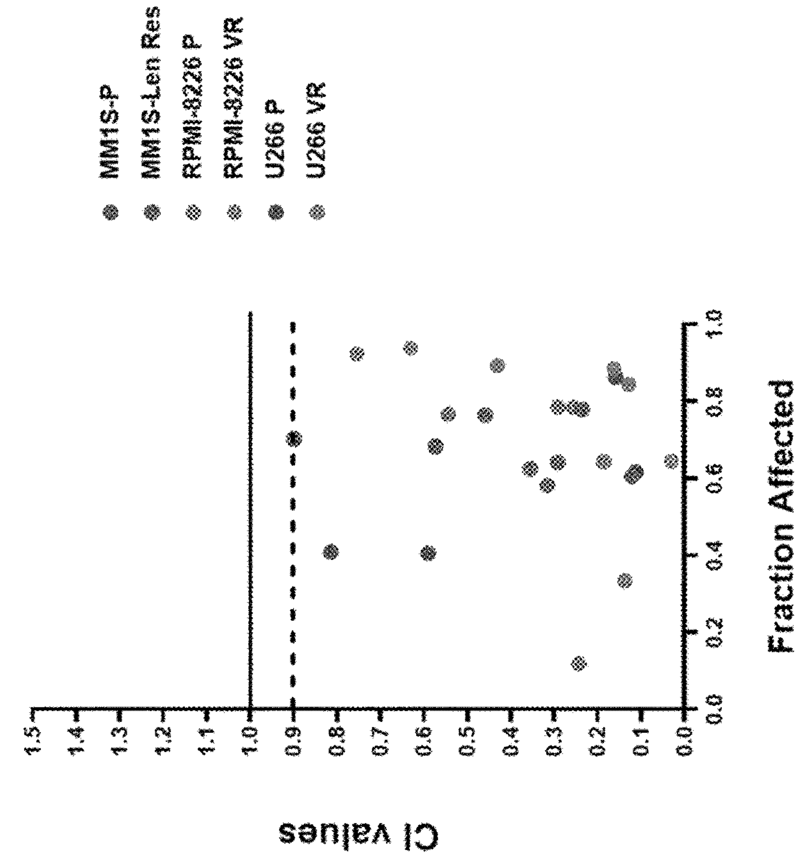
FIG. 9A and FIG. 9B depict representative results from experiments demonstrating drug synergy using combination index (CI) values.
Figure 9A:
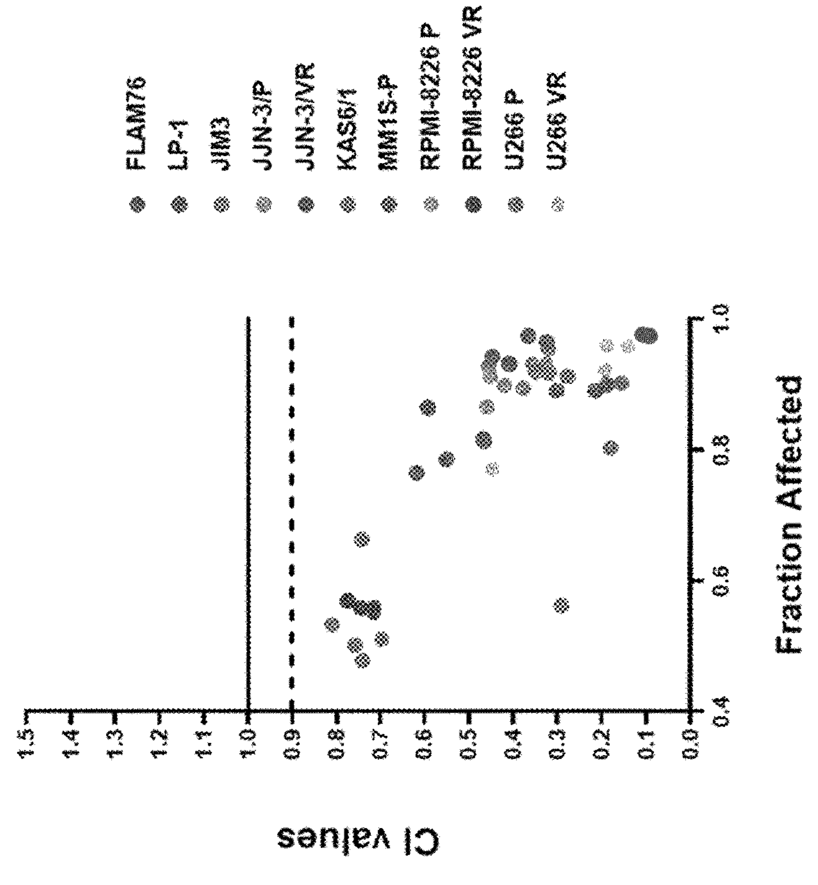

Next, experiments were done to test the cytotoxicity of CLF in combination with PIs (represented by Ixazomib; FIG. 2A through FIG. 2C) or IMiDs (represented by Lenalidomide; FIG. 2D) in HMCLs representing innate-sensitive (FLAM76, KAS6/1, MM1S), innate-resistance (JIM-3, LP-1), and acquired-PI or IMiD resistance (U266 P/VR, RPMI8226 P/VR, JJN-3 P/VR, and MM1S P/LenR). The CLF+PI and CLF+Len combination index (CI) values calculated using the Calcusyn program were consistently less than 0.9 (FIG. 9), indicating synergy (Chou et al., 2010, Cancer Res., 70:440-6). Further, CLF improved the therapeutic index of PI and IMiD administration to the cells and decreased the amount of PI/IMiD required to achieve effective responses, as indicated by dose reduction index (DRI) values and predicted decrease in IC50 (nM concentration).

Although the CLF doses used in combination treatments were in the micromolar concentration range, this is within the safe dose range of 0.84-8.4 μM, which corresponds to human plasma Cmax of 0.4-4 mg/L (Kumar et al., 2019, Haematologica., 105:971-86).

Figure 3A:
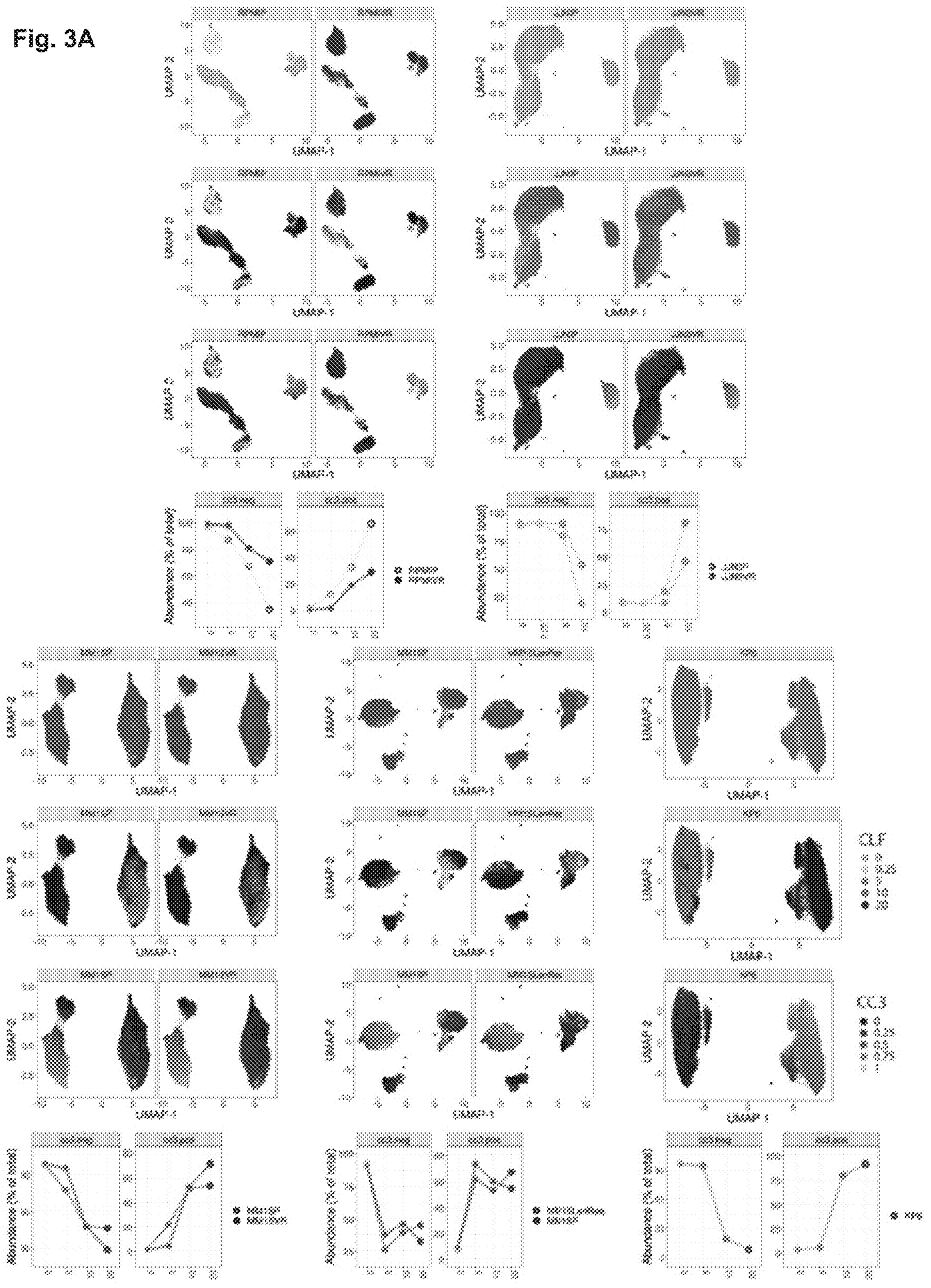
FIG. 3A through FIG. 3D depict representative results from experiments showing CyTOF analysis in multiple myeloma cell lines (representing sensitive, PI-resistance and IMiD-resistance) and patient primary cells.

CyTOF Analysis Reveals CLF-Induced Key Proteomic Changes at Bulk and Subclonal Levels Mass Cytometry (CyTOF) analysis was performed to assess CLF-induced changes in phenotypic and functional markers in myeloma cells on a single-cell level and identify unique subgroups that change in relation to disease progression. CyTOF analysis was performed on 77 total samples across 7 Experiments/Batches. This included 4 isogenic sensitive/acquired PI and IMiD resistant pairs (U266, MM1S, RPMI8226, JJN3), 8 innate-sensitive cell lines, and 7 innate-resistant HMCLs. Batch correction was performed for combining samples. Similar clusters across all samples were grouped to compare sub-populations and to calculate the proportion of cells with increases or decreases in markers for each sample. CyTOF analysis revealed distinct cluster of cells defined by elevated cleaved caspase levels in all cell lines and primary samples, which was enriched for cells exposed to high dose CLF (FIG. 3A).

Figure 3B:
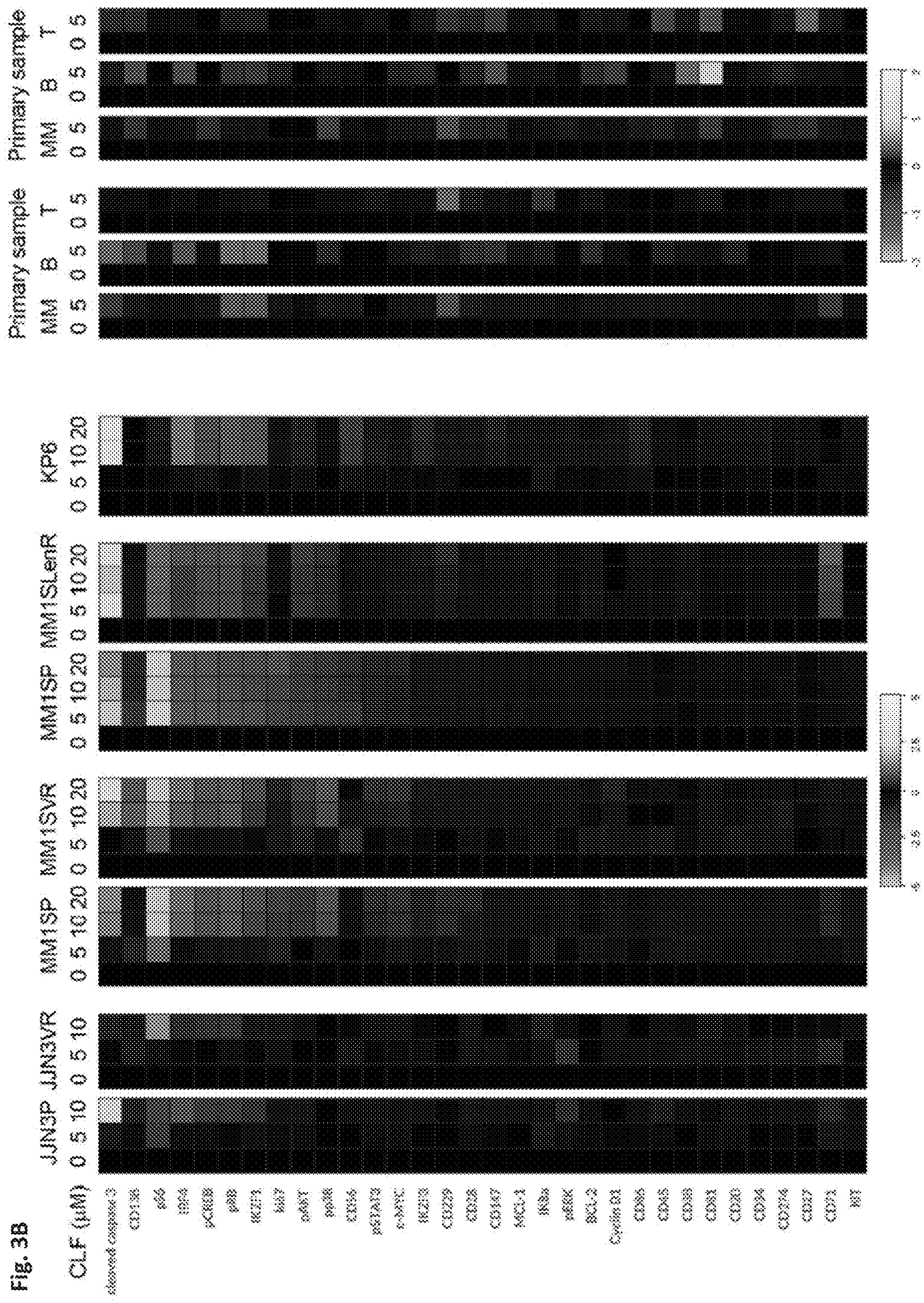
Figure 3C:
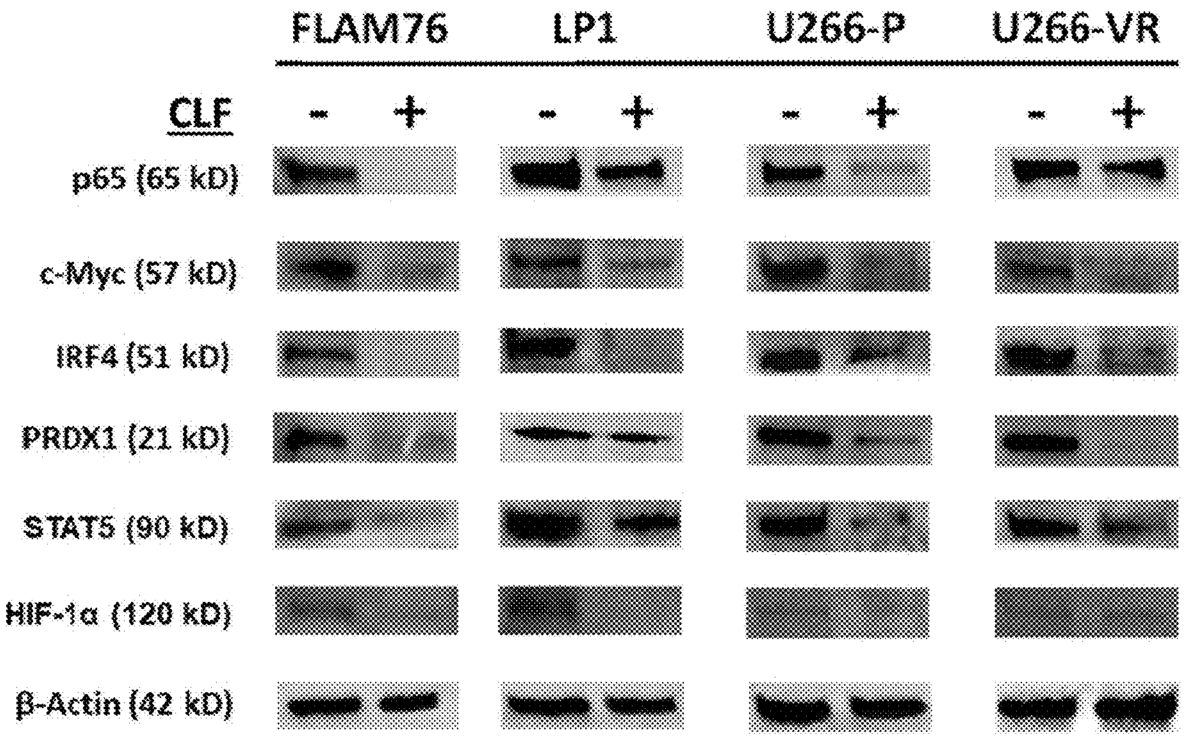

Myeloma cells are addicted to several proteins like c-Myc, IRF4, and IKZF 1. Pre- vs. post-treatment differential expression analysis using CyTOF (FIG. 3B) and immunoblotting (FIG. 3C) revealed shifts in a majority of these markers following clofazimine treatment, including IRF4, IKZF1, IKZF3, CD229, CD27, pS6, pERK, and IkBa.

Figure 3D:
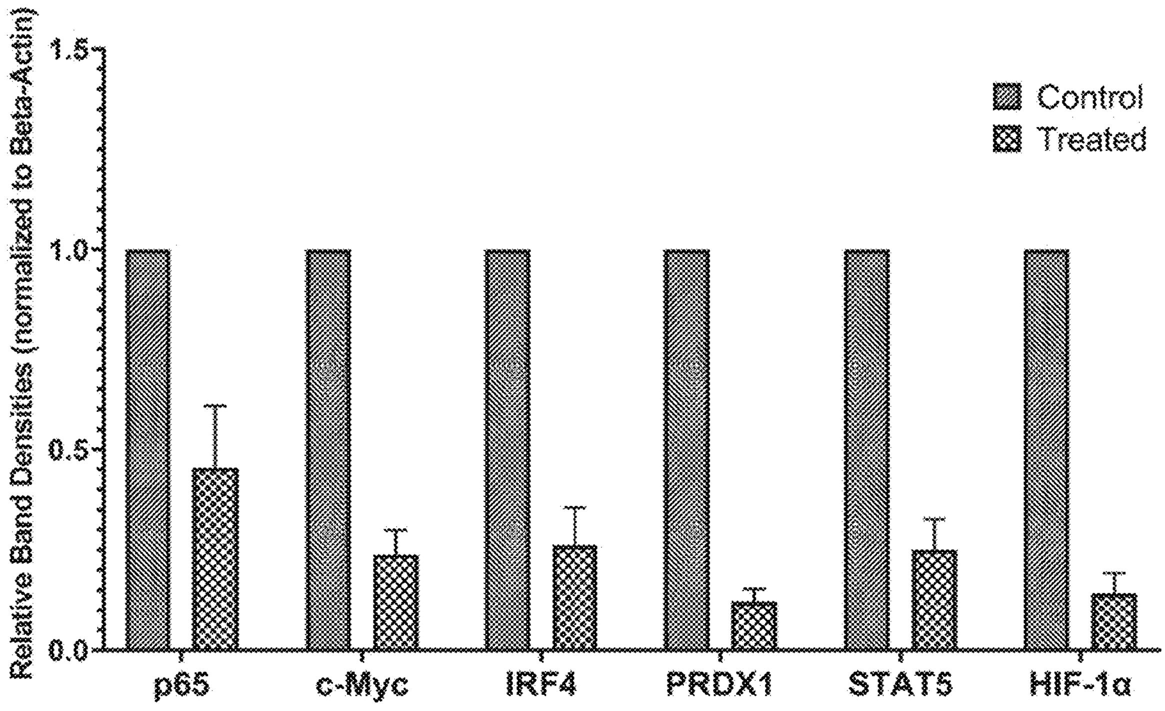

Furthermore, previously it was found that CLF also suppresses STAT expression in C ML and consequently downregulated stem cell maintenance factors like hypoxia-inducible factor-1α and -2α and Cbp/P300 interacting transactivator with Glu/Asp-rich carboxy-terminal domain 2 (CITED2) (Kumar et al., 2019, Haematologica., 105:971-86). Concurrently, data has also shown downregulation of STATS and HIF-1α in myeloma following CLF treatment (FIG. 3D).

CLF Induces Apoptosis via Mitochondrial-Mediated Pathway in Myeloma

Figures 4A, 4B, 4C:
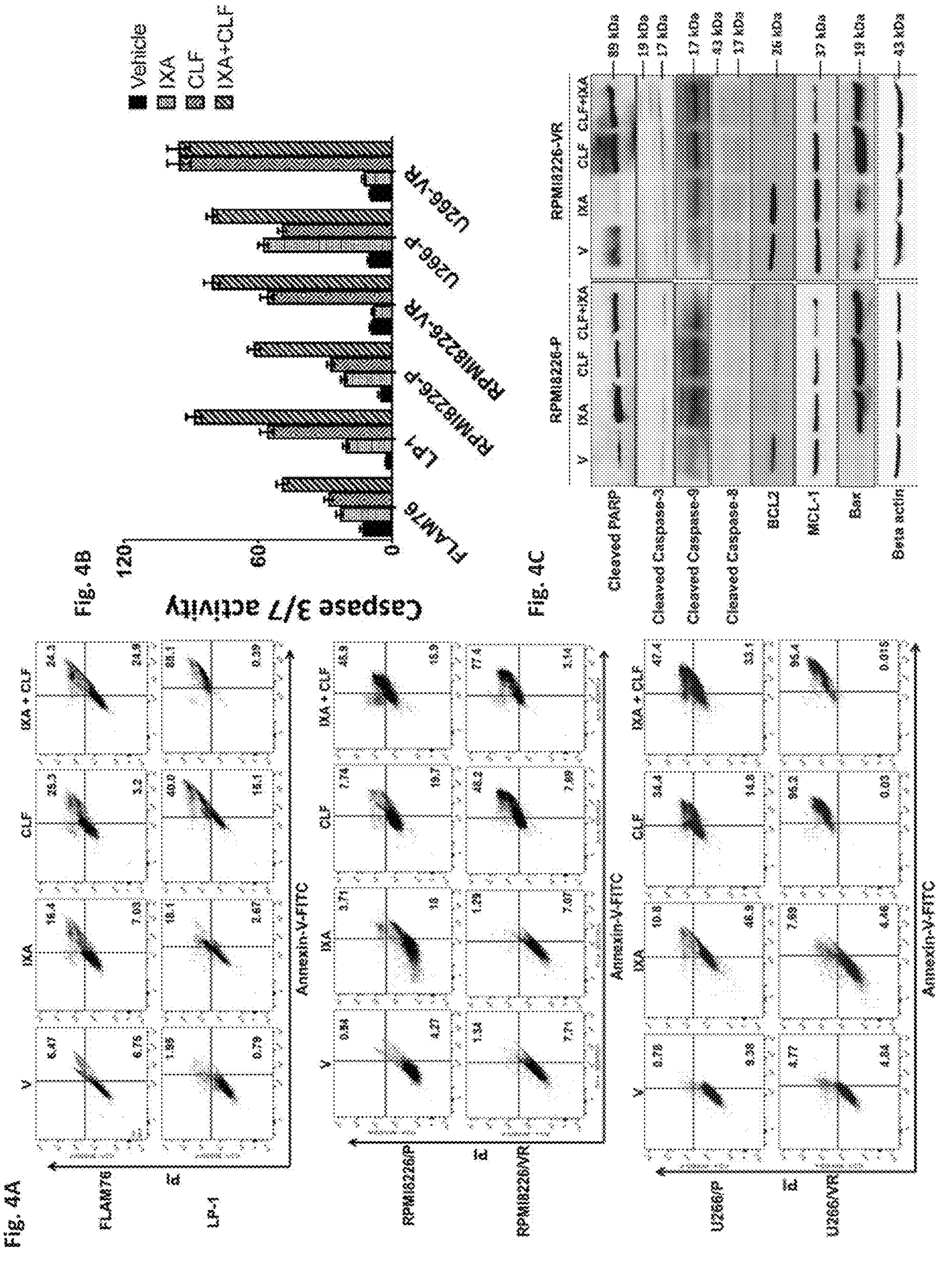
FIG. 4A through FIG. 4F representative results from experiments showing that CLF induces apoptosis in sensitive and innate resistant MM cell lines.
Figure 10B:
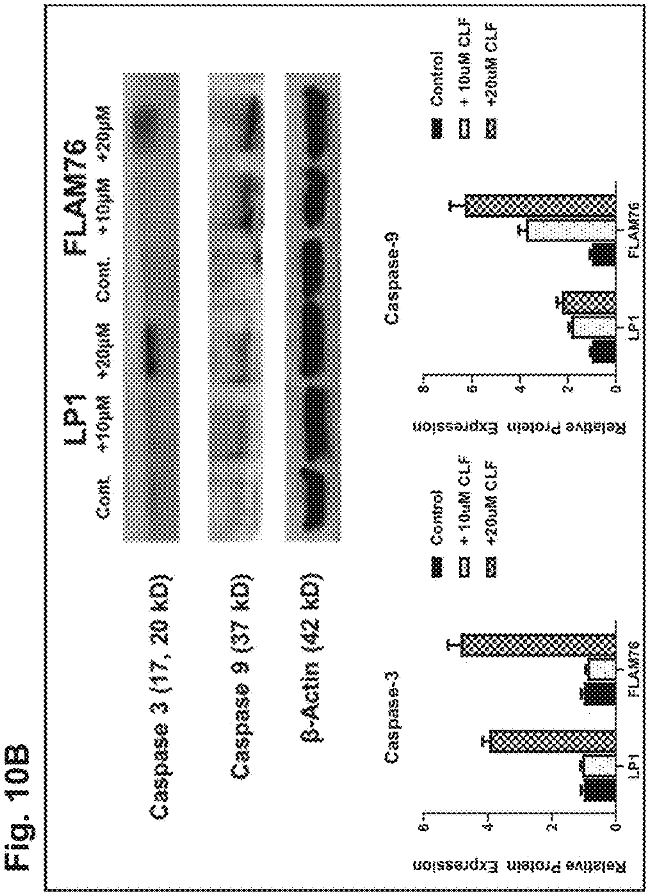
FIG. 10A through FIG. 10C depict representative results from experiments demonstrating the effect of CLF-treatment on the induction of apoptosis in myeloma.
Figure 10A:
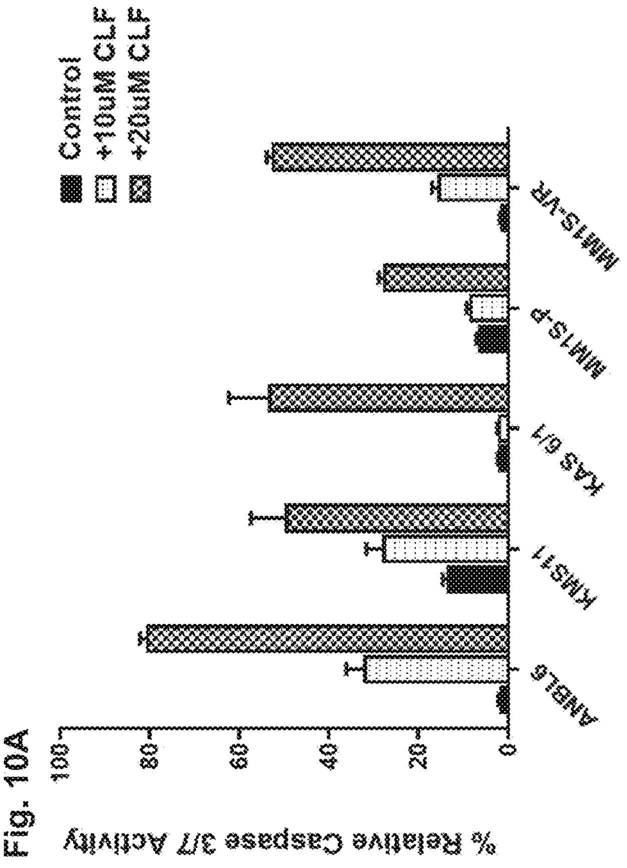
Figure 10C:
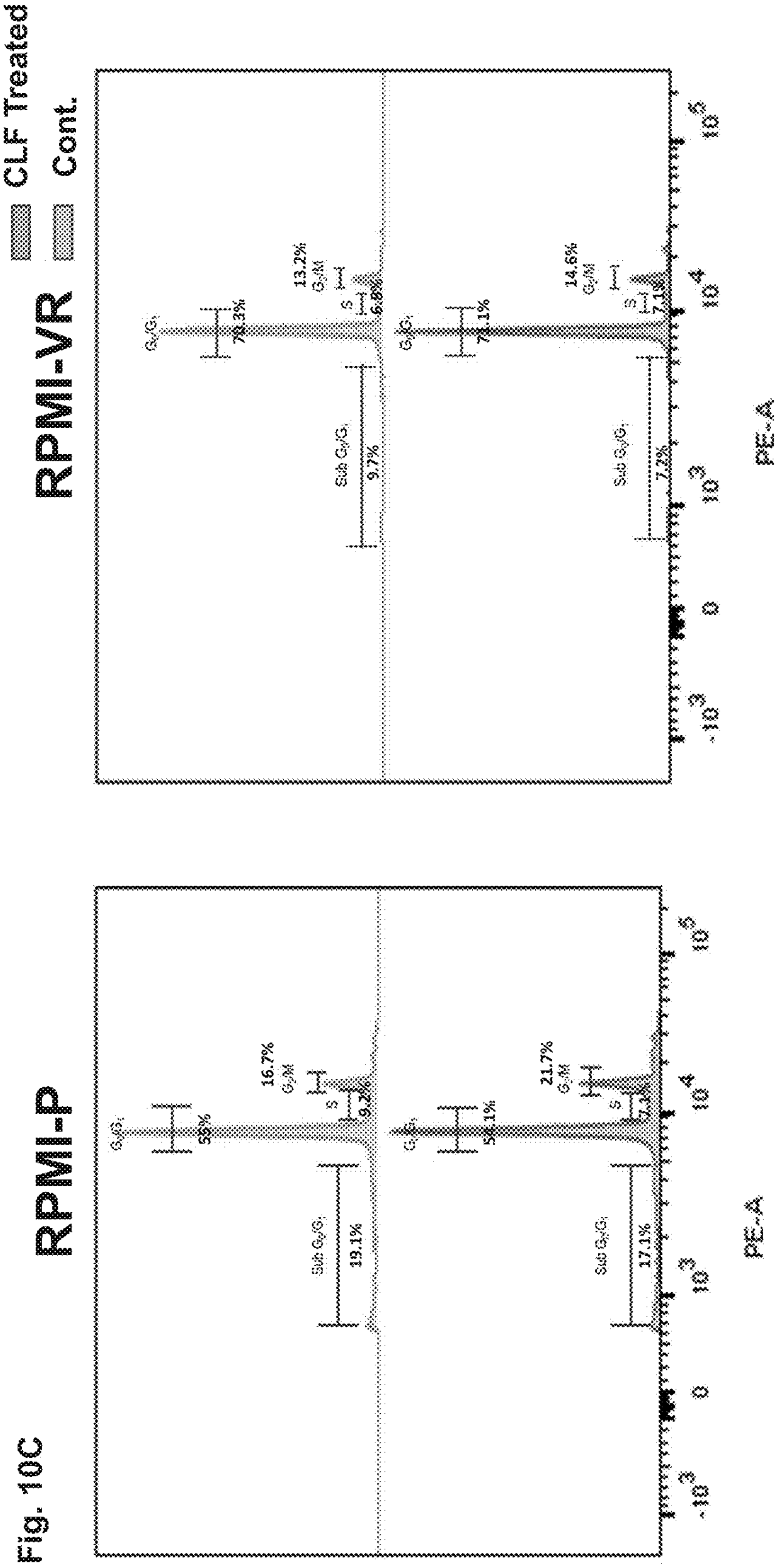

Next, to confirm whether the loss of cell viability was indeed due to apoptosis (as indicated by CyTOF analysis results; FIG. 2A through FIG. 2D), annexin V staining using flow-cytometry was performed. CLF induced significant apoptosis either alone or in combination with 15 nm ixazomib in HMCLs (FIG. 4A). CLF-induced caspase-3 activity was also confirmed by luminescent-based Caspase 3/7 assay (Promega) (FIG. 4B). Experiments showed that CLF activated caspase-3 and 9 but not 8, indicating that CLF-induced apoptosis was dependent on mitochondria-mediated pathway (Western blotting; FIG. 4C). This is consistent with decrease in the anti-apoptotic/survival markers Bcl2, Mcl-1 and increase in Bax expression (FIG. 4C). Furthermore, using Caspase 3/7 assay (FIG. 10A) and Western blotting (FIG. 10B) it was demonstrated that CLF treatment results in induction of apoptosis in myeloma lines. When gated for live cells, the percentage of cells in G0/G1, S, G2/M, and sub G0/G1 phases in pre- vs. post-CLF treatment HMCLs are shown in FIG. 10C.

Figure 4D:
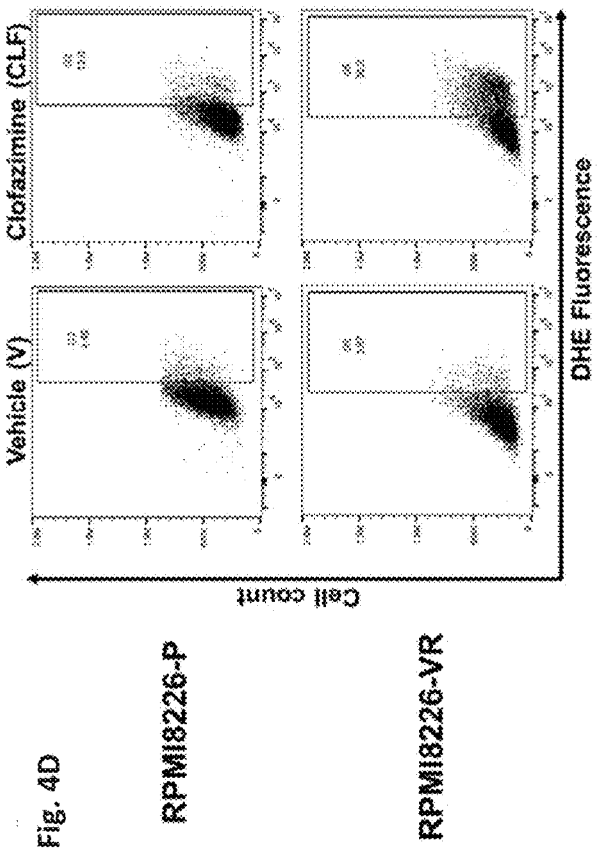
Figure 4E:
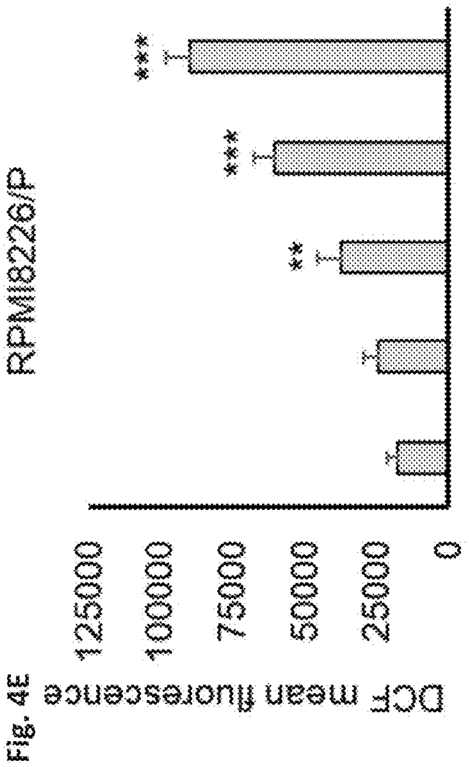
Figure 4E:
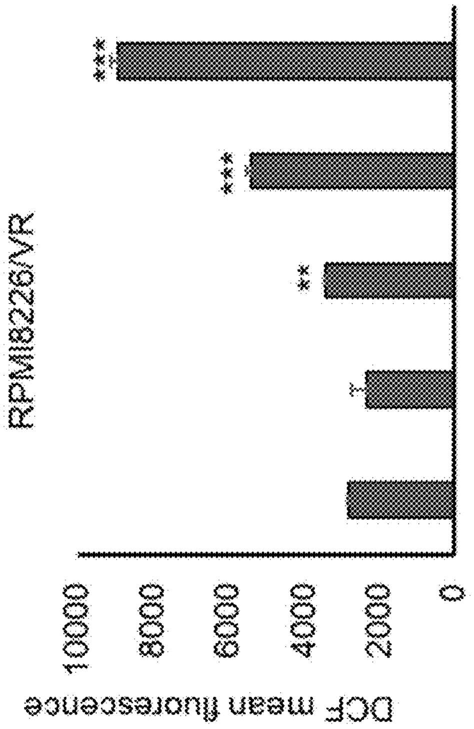
Figure 4F:
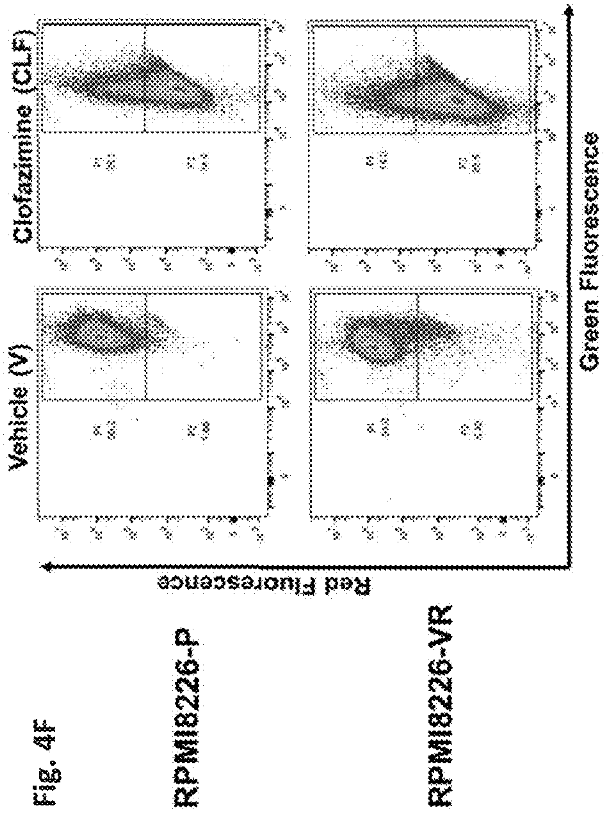
Figure 11B:
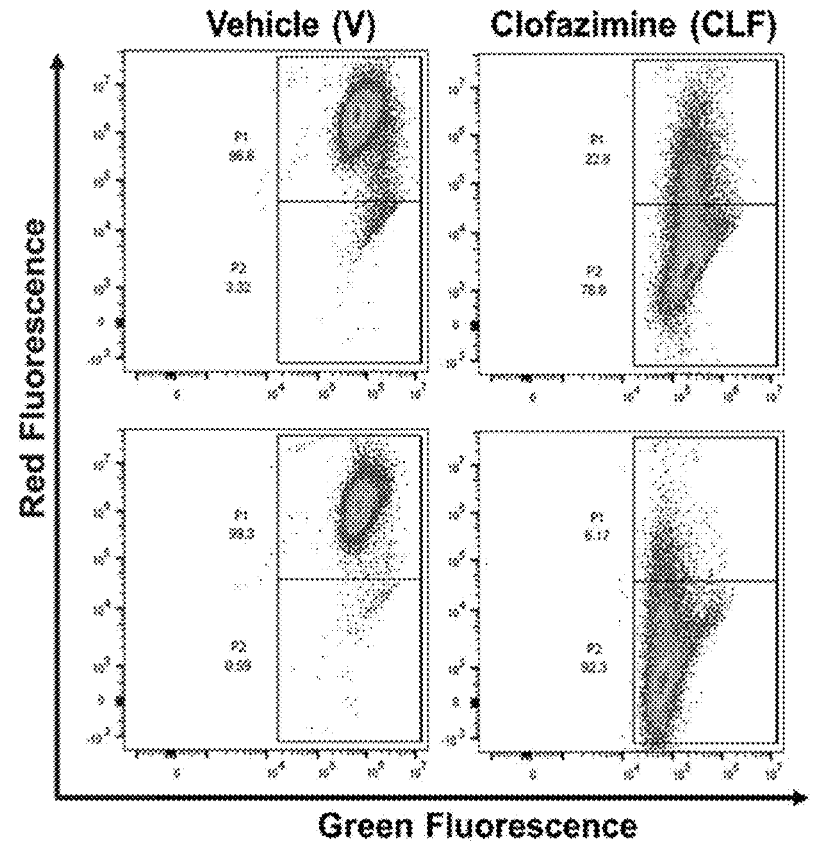
FIG. 11A and FIG. 11B depict representative results from experiments demonstrating that CLF induces superoxide levels, and mitochondrial membrane potential (MMP) in the myeloma cell line pair U226 P/VR cell line pair.
Figure 11A:
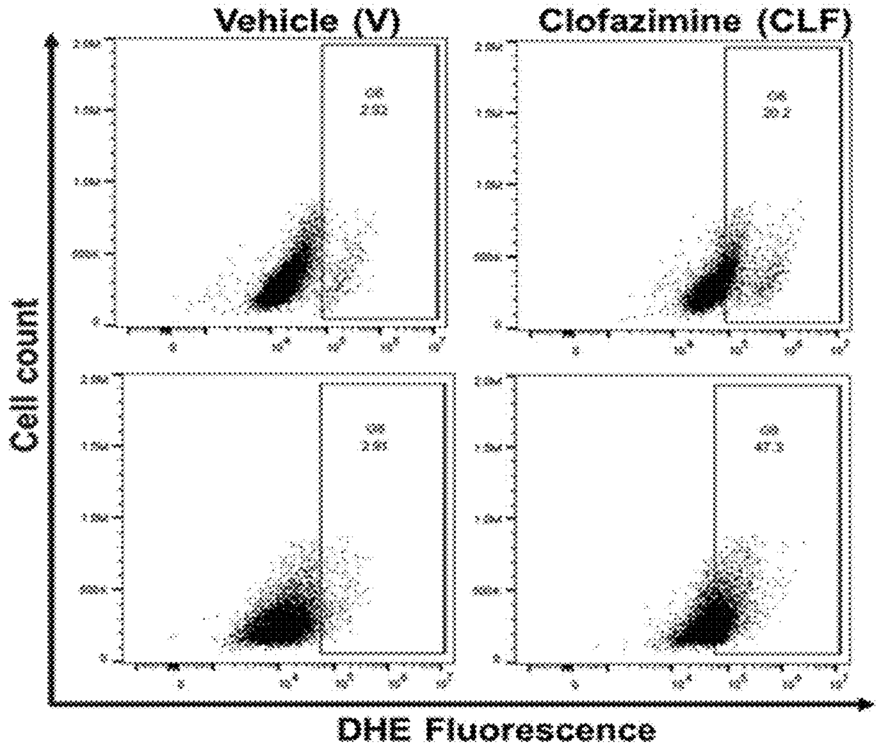

Previously, it has been reported that CLF imparts its anti-bacterial actions by generating reactive oxygen species (ROS), particularly superoxides and hydrogen peroxide ($H_2O_2$). DCFDA (Sigma), which shows fluorescence when it is oxidized, was used to measure intracellular ROS. Cellular superoxide anions were measured by using the fluorescent dye DHE (Sigma). Mitochondrial membrane potential was assessed using JC-1 (Sigma). JC-1 is a cationic carbocyanine dye that accumulates in mitochondria. Representative plots demonstrate that induction of cellular superoxide anions was observed (FIG. 4D) and intracellular ROS production (FIG. 4E) that causes mitochondrial membrane depolarization following CLF treatment in the cell pair RPMI8226P/VR (FIG. 4F). Similar results were also obtained for the U266P/VR cell line pair (FIG. 11A and FIG. 11B).

Figure 12:
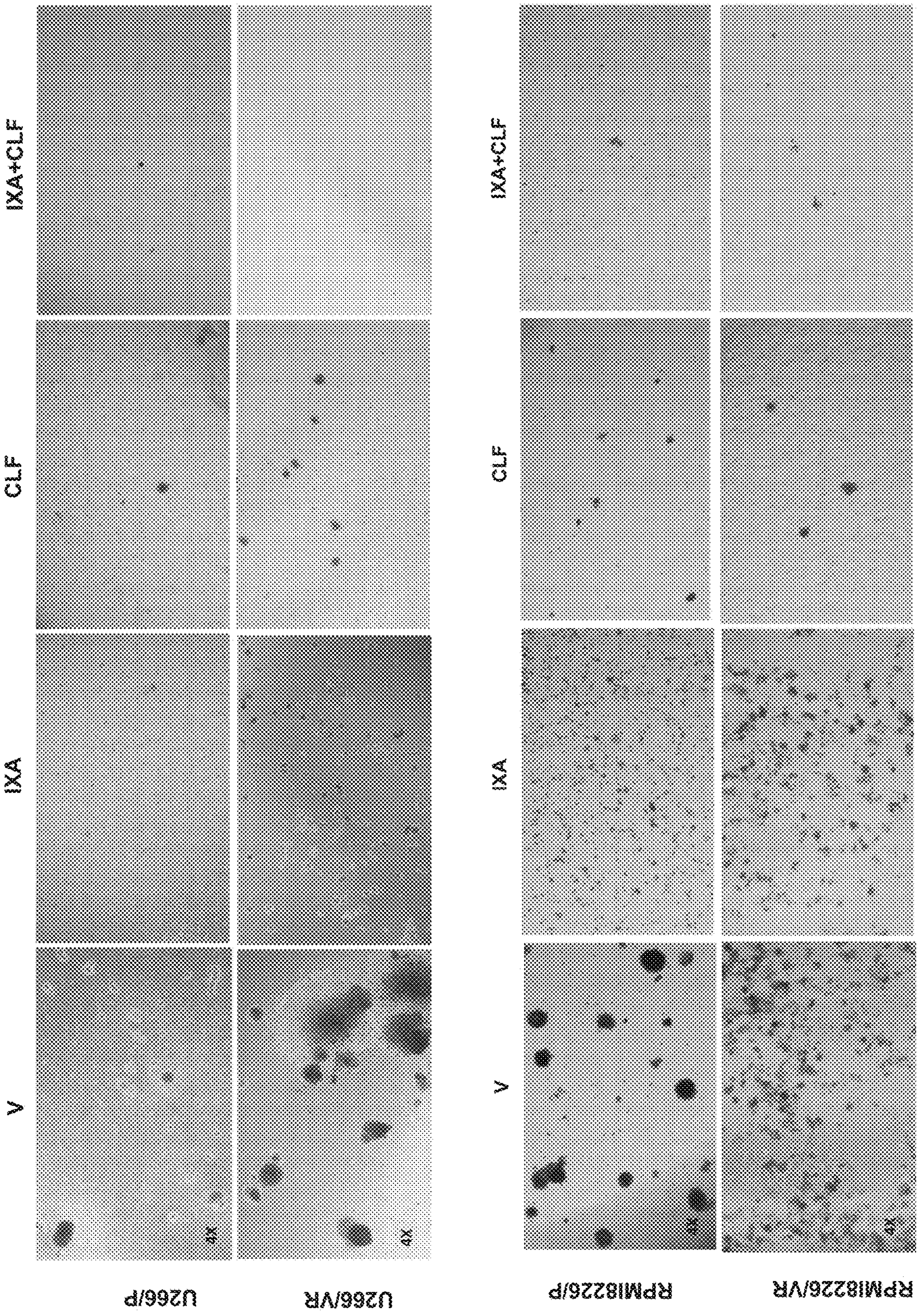
FIG. 12 depicts representative images from colony forming assays, demonstrating that CLF significantly reduces colony formation in PI-sensitive and resistant HMCLs (RPMI826 P/VR and U266 P/VR).

CLF Inhibited Myeloma Colony Formation, Aldefluor® Activity and Eroded Quiescent and Side Population Cells Experiments showed that CLF alone significantly reduced colony number as well as colony size when compared to control or ixazomib. Combination of CLF with ixazomib further reduced the colony numbers. Importantly, CLF significantly reduced colony formation in PI-resistant lines (RPMI826 P/VR and U266 P/VR) (FIG. 12).

Figure 5A:
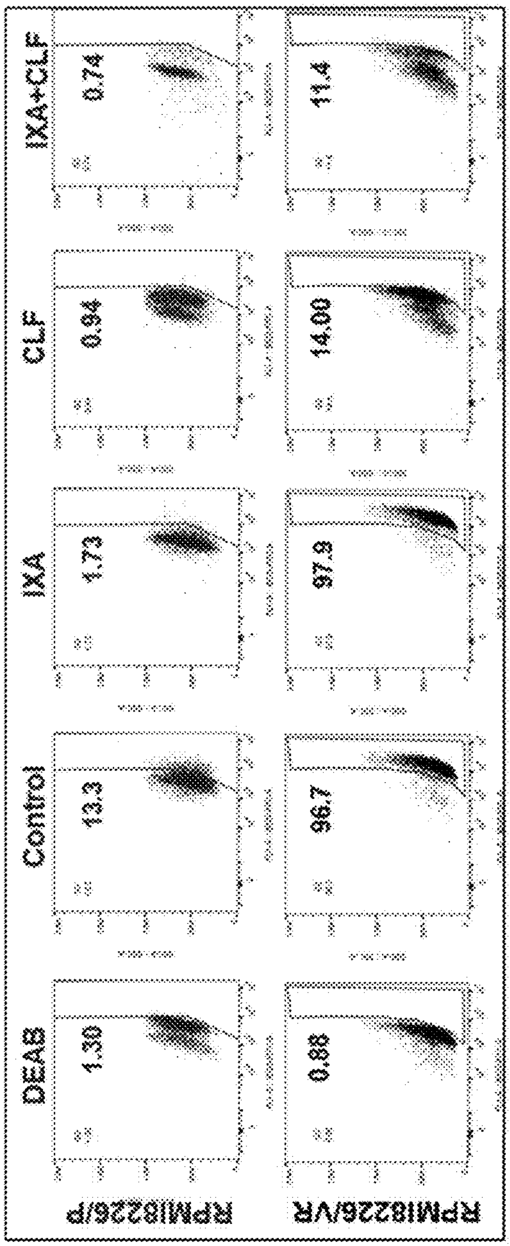
FIG. 5A through FIG. 5D, depicts representative results from experiments showing that CLF kills myeloma cells with cancer stem-like properties (CSCs). The results depicted utilized the RPMI8226 P/VR cell line pair.
Figure 13B:
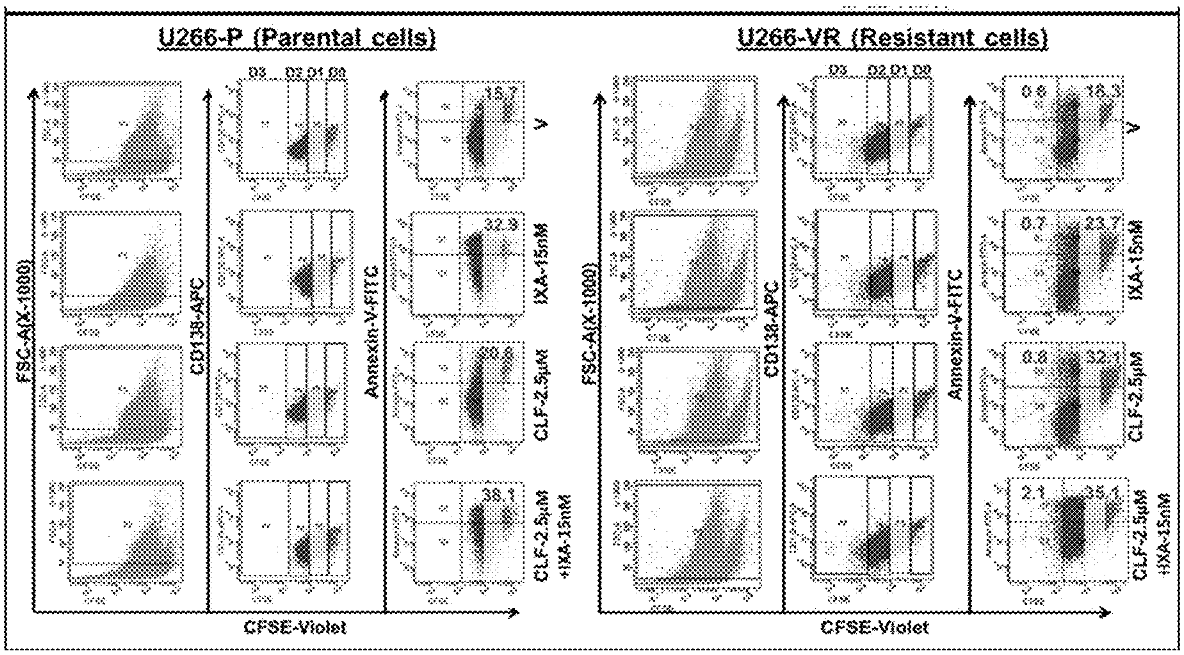
FIG. 13A through FIG. 13C depict representative results from experiments demonstrating that CLF kills MM cells with cancer stem-like properties (CSCs).
Figure 13A:
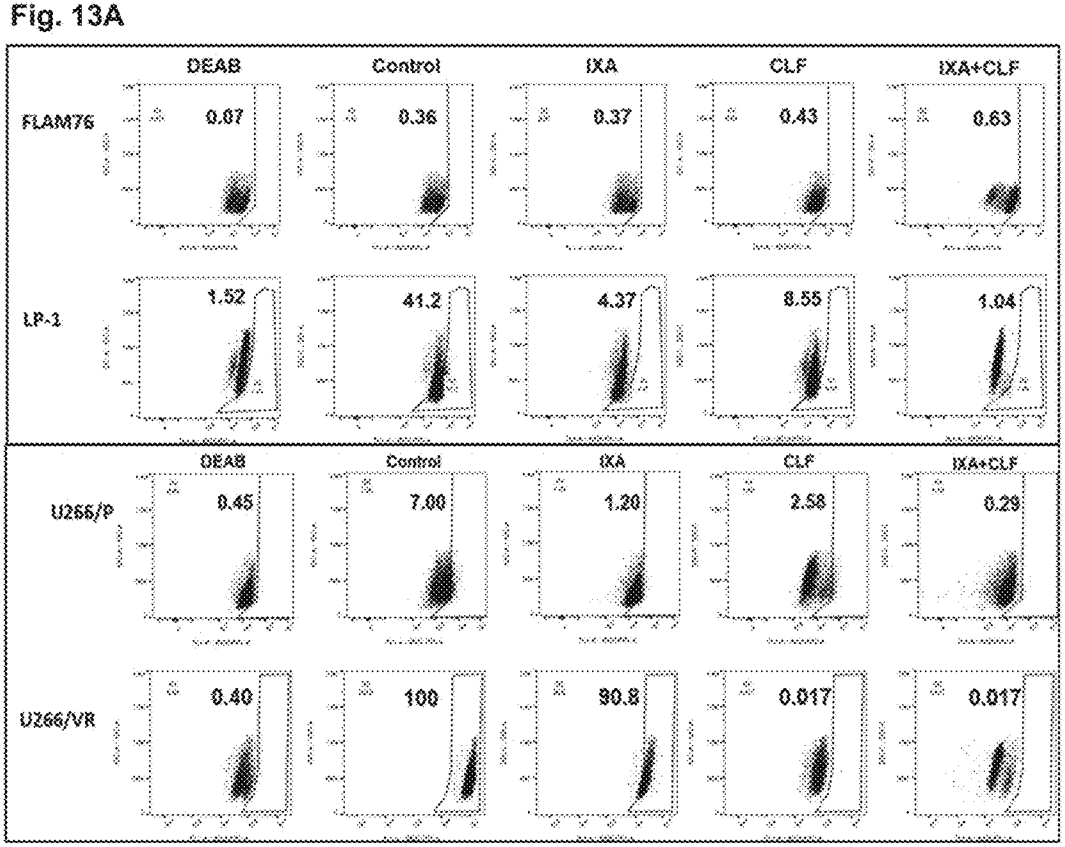

FIG. 5A and FIG. 13A show baseline ALDH (aldehyde dehydrogenase) activity in PI-resistant HMCLs compared to sensitive HMCLs. While no/very low ALDH activity was observed in the PI-sensitive line FLAM76, ALDH activity was found remarkably higher (>95%) in clonally derived PI-resistant HMCLs RPMI8226-VR, U266-VR compared to innate resistant LP-1 cell line. CLF caused a significant decrease in ALDH activity, and its effect was comparable with control (FIG. 5A).

Figure 5B:
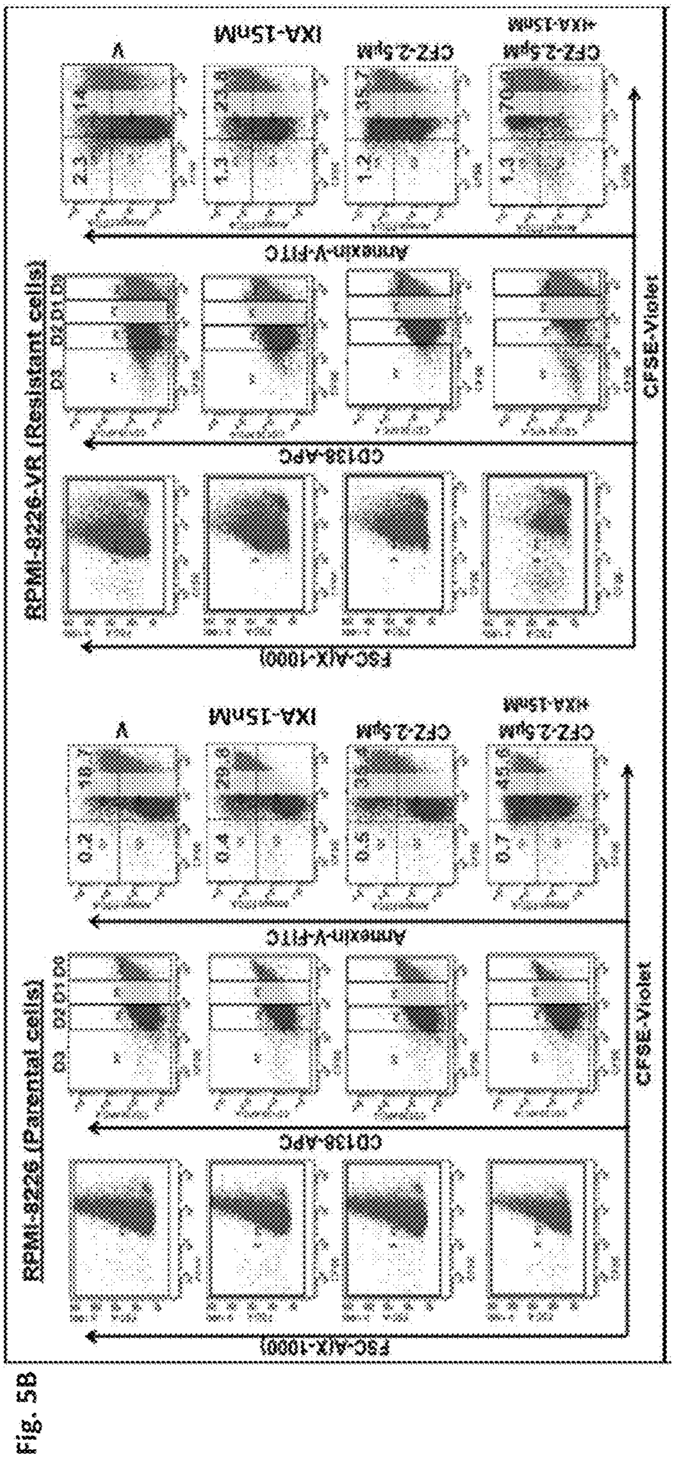

Carboxyfluorescein succinimidyl ester (CFSE) assays were performed to evaluate if CLF alone or in combination with PIs could erode quiescent CFSE+ cells in parental (P) and clonally derived PI-resistant (VR) cells, RPMI8226P, RPMI8226VR, U266P, and U266VR. While PIs failed to reduce CFSE-bright (non-dividing) cells, CLF alone or in combination with ixazomib significantly reduced their number and increased CFSE-dim (dividing cell) population (FIG. 5B and FIG. 13B). Remarkably, evaluation of apoptosis in these cells revealed that CLF alone caused apoptosis in both CFSEbright and CFSEdim cells while combining CLF+ixazomib caused a more robust effect amounting to near obliteration.

Figure 5C:
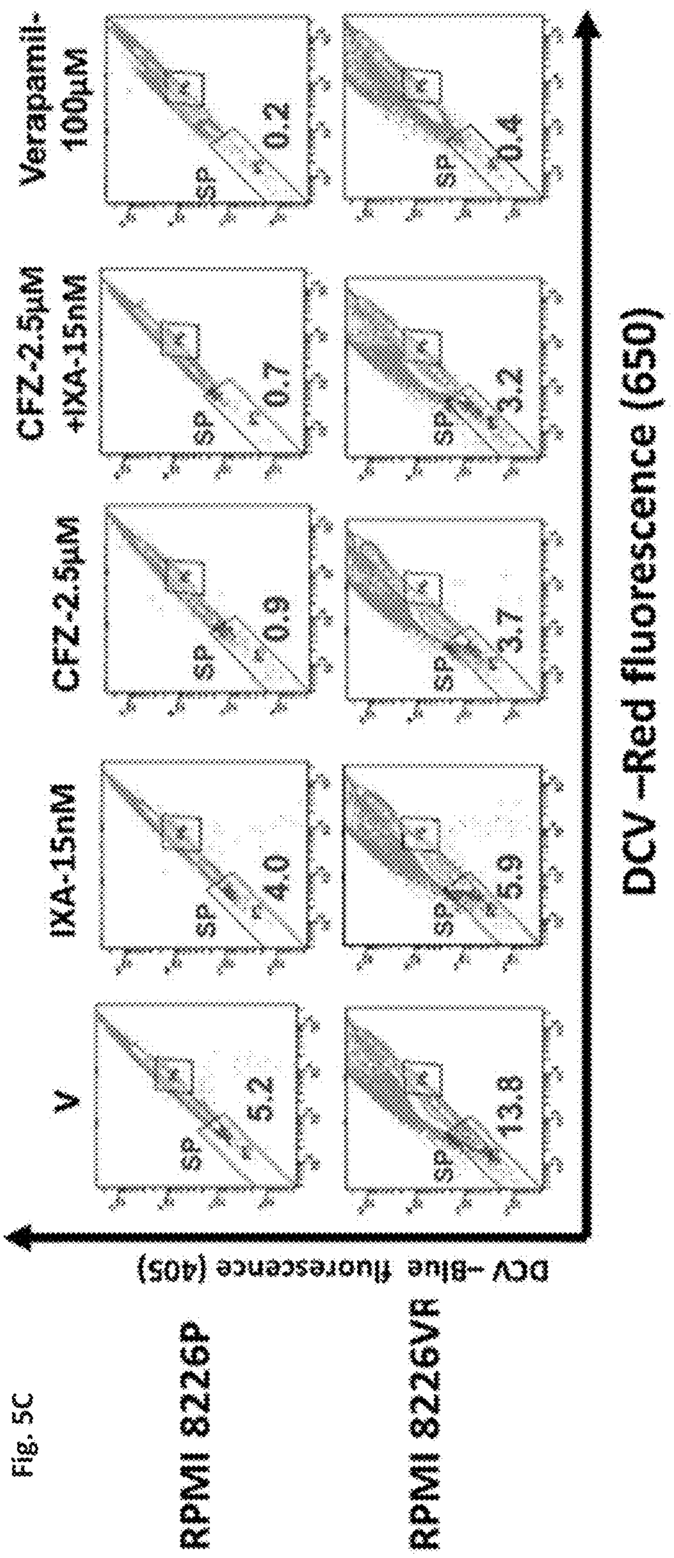
Figure 5D:
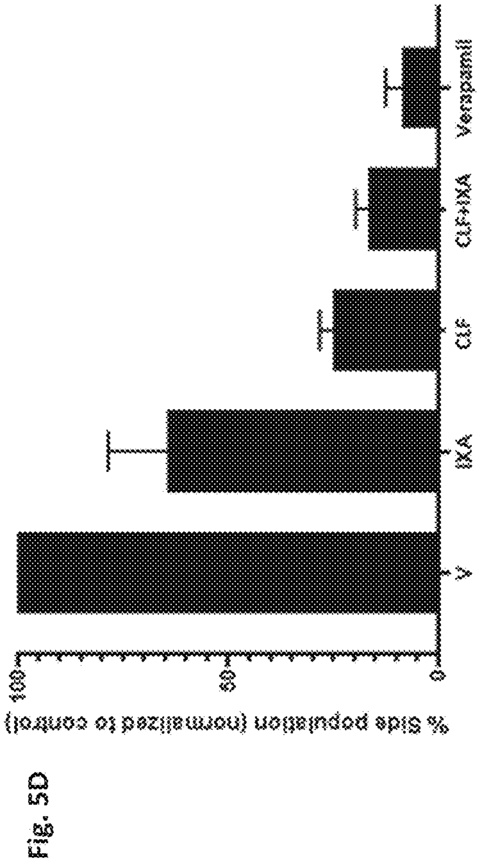
Figure 13C:
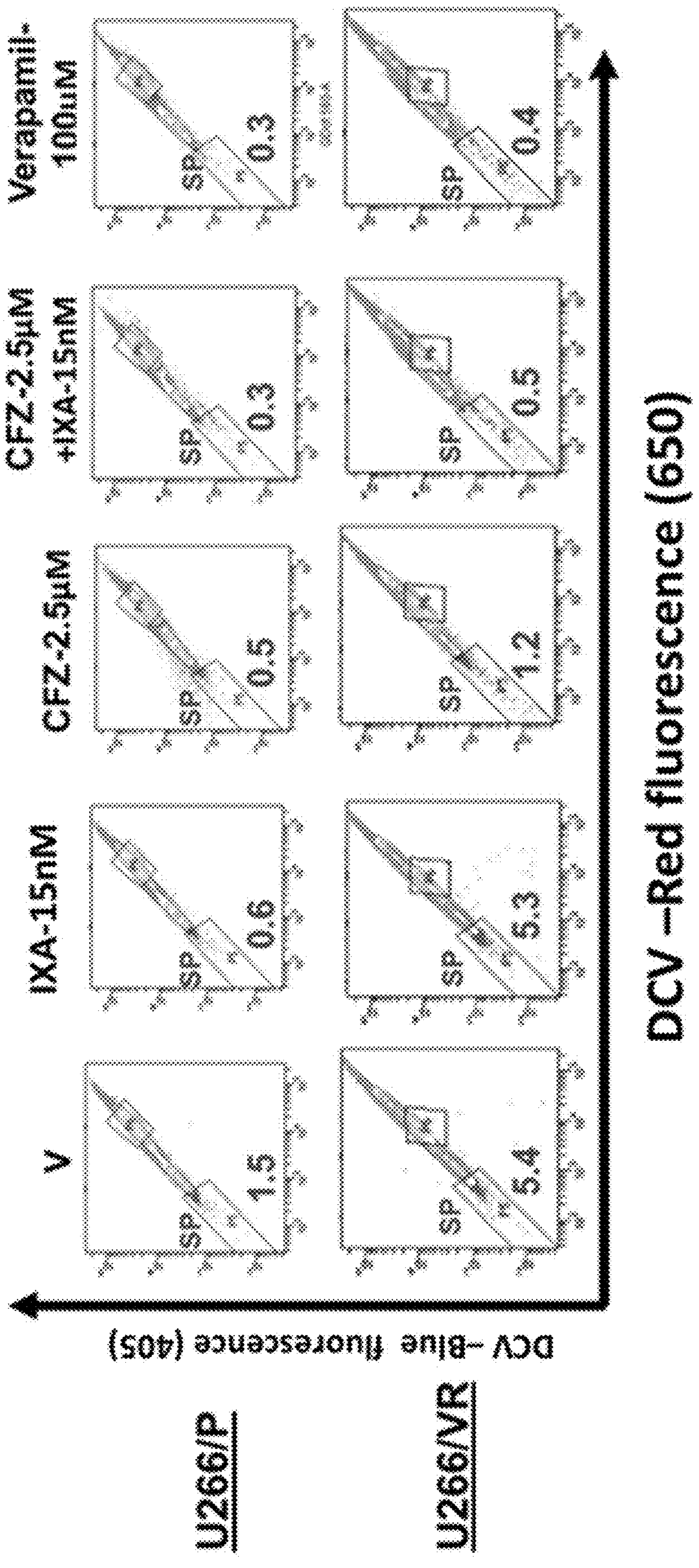

Side population (SP) cells were gated and selected from main populations (MP) using DyeCycle® violet, pre- and post-CLF treatment. Experiments found that baseline % SP is higher in resistant cells as compared to parental cells, as shown in (FIG. 5C and FIG. 13C). Notably, CLF alone or in combination (CLF+PI) reduced SP in PI-resistant HMCLs (FIG. 5C and FIG. 13C). A summary of the results is provided as bar plots in FIG. 5D.

Gene Expression Profiling Reveals Potential CLF Mechanism of Action and CLF-Induced Cell Death Genome-wide transcriptome (next-generation mRNA sequencing or RNAseq) analysis showed 864 genes differed significantly at baseline between the CLF-sensitive and the CLF-resistant groups ($p<0.05$; fold-difference≠1). Among these, 524 genes had least squares (LS) Mean of 1 or higher in both sensitive and resistant groups. IPA analysis revealed phagosome maturation ($p=2.45\times10^{-5}$), DNA methylation and transcriptional repression signaling ($p=6.80\times10^{-4}$), autophagy ($p=1.51\times10^{-3}$), BEX2 signaling pathway ($p=1.34\times10^{-3}$) as the top canonical pathways associated with CLF sensitivity.

Figure 6A:
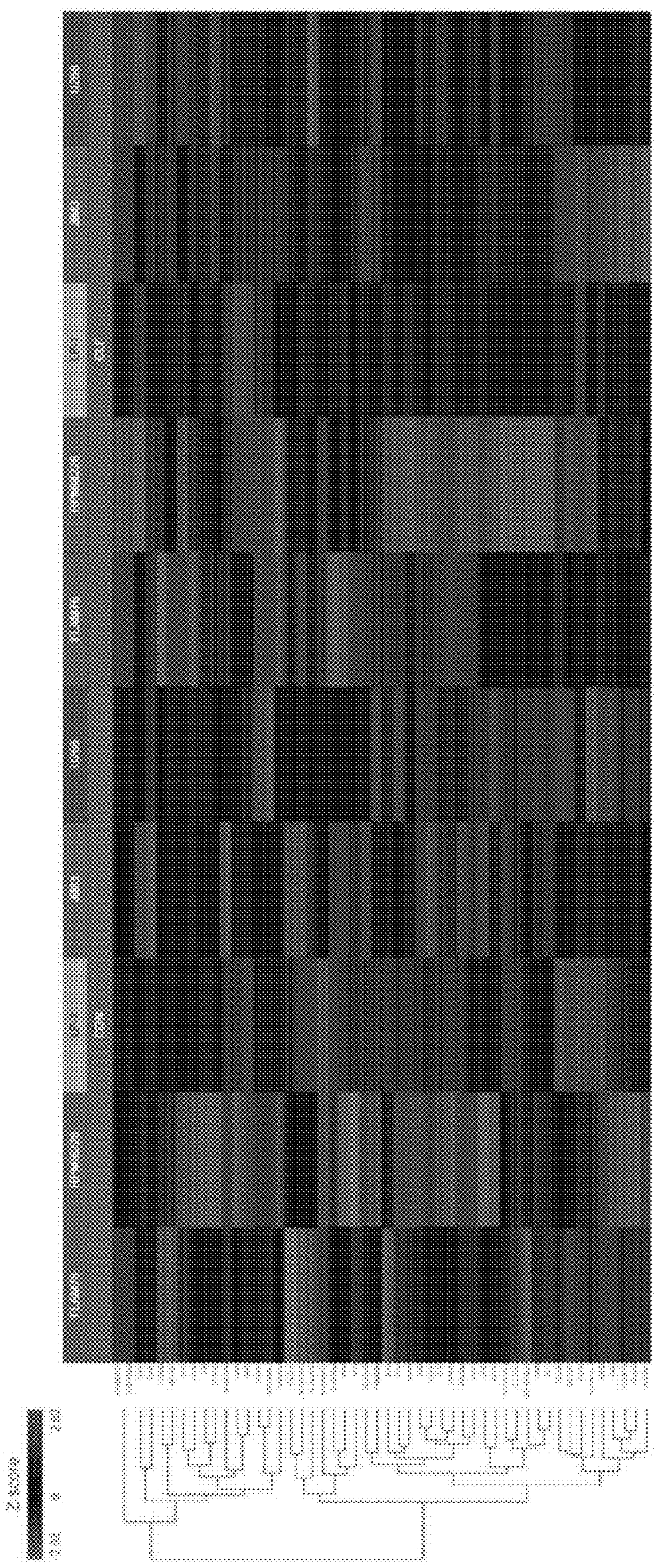
FIG. 6A through FIG. 6E depict representative results from experiments showing pre- vs. post-treatment differential gene expression analysis (RNA sequencing). Heatmaps represent top differentially expressed genes following Gene-specific analysis (GSA), a statistical modeling method to identify differentially expressed genes.
Figure 6B:
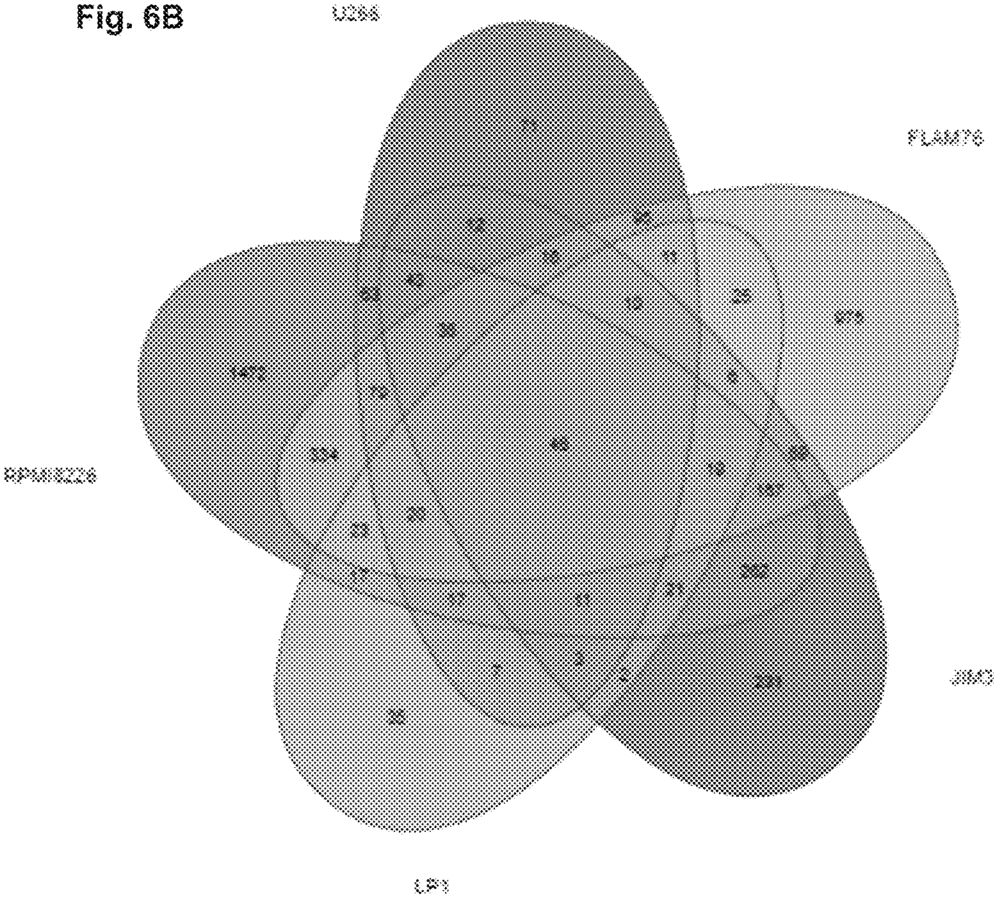
Figure 6C:
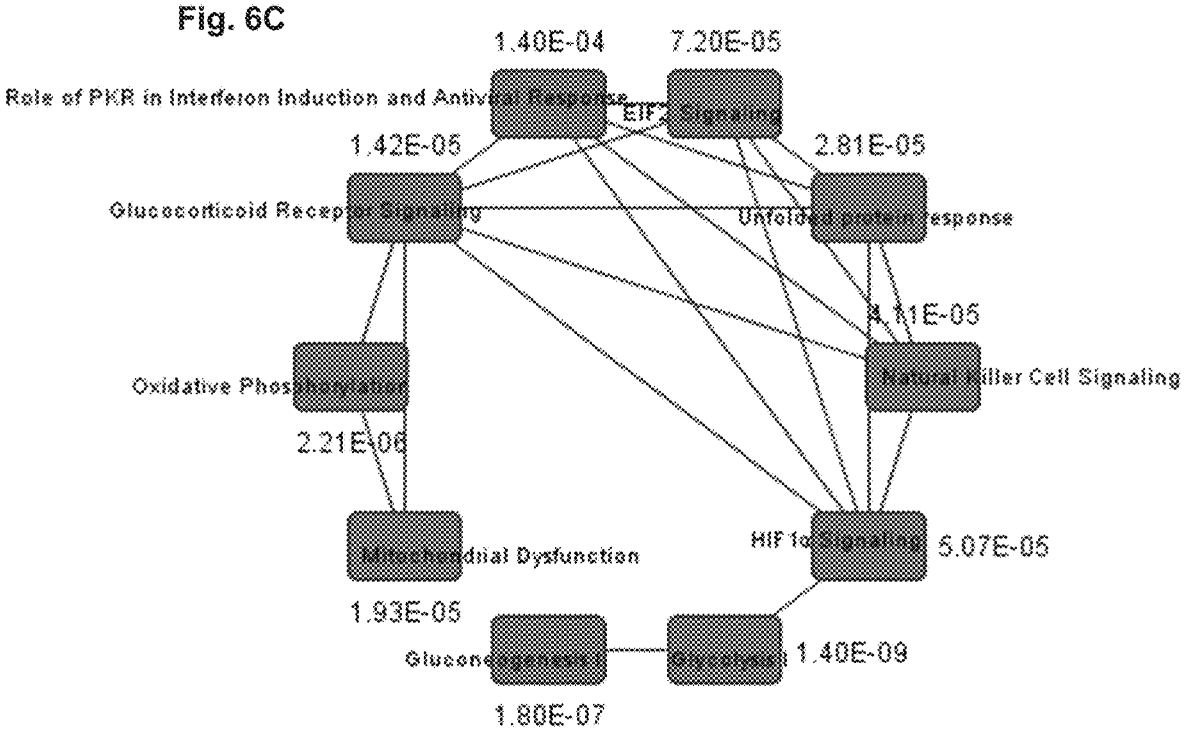
Figure 14:
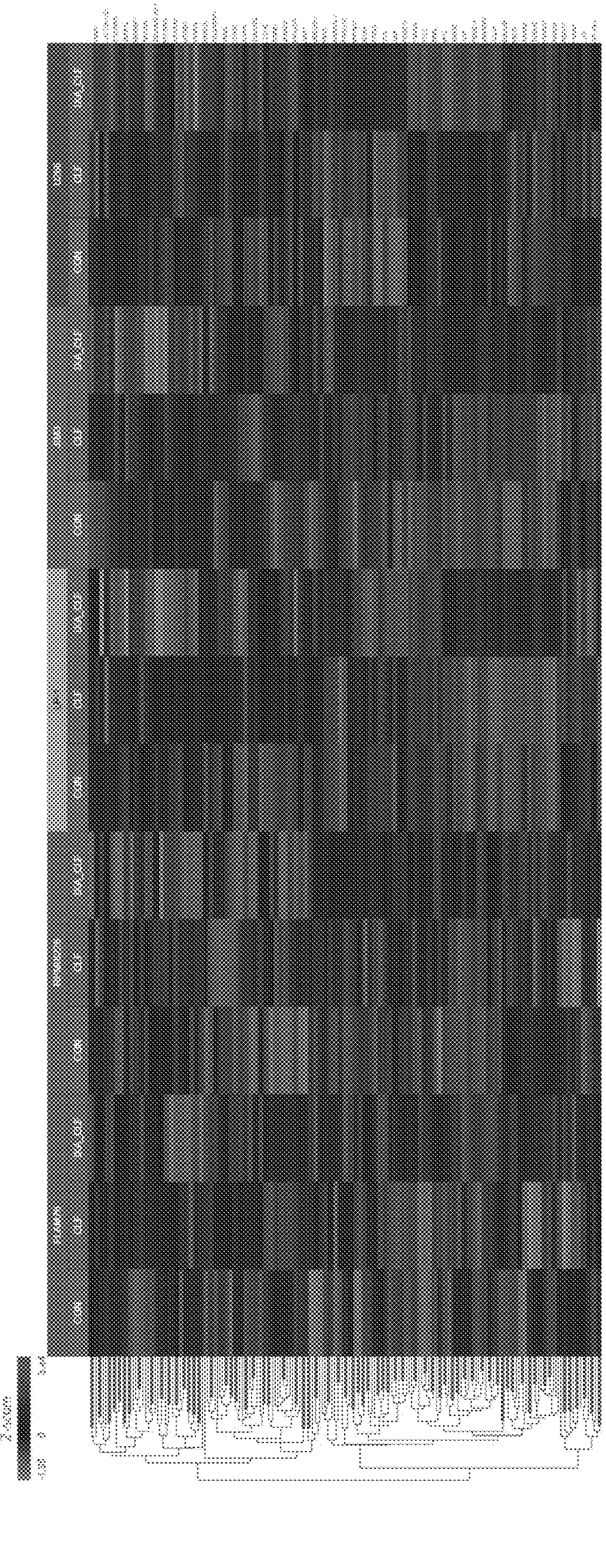
FIG. 14 depicts a representative heatmap of genes that were significant in either CLF vs CON and/or CLF+IXA vs CON with LS Mean≥1 and ANOVA p-value <0.05.
Figure 15:
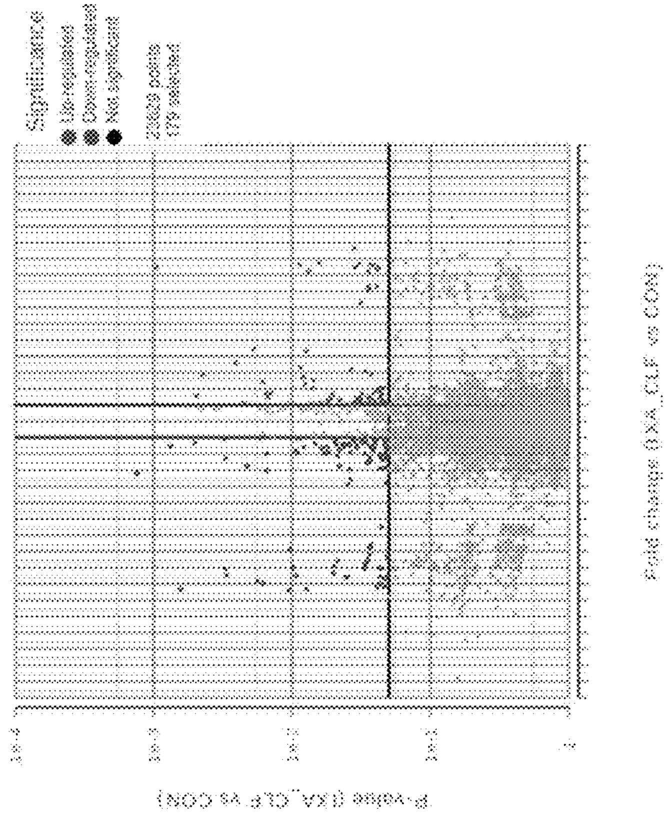
FIG. 15 depicts representative volcano plots of pre- vs post-treatment.
Figure 15:
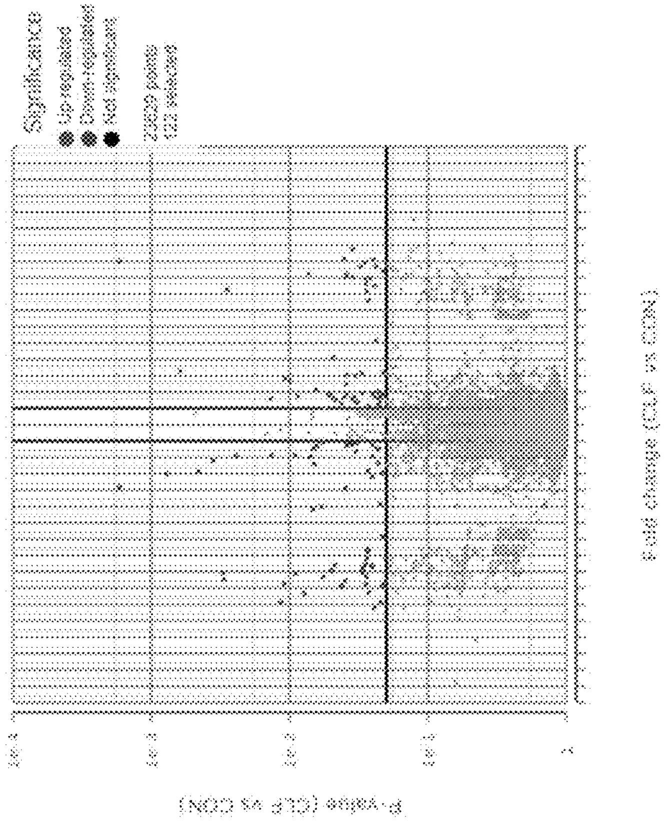

Next, analysis of kinetic changes in gene expression patterns between untreated (baseline) vs. treated (24 hrs post-treatment) cells were performed. FIG. 14 shows a heatmap of all the genes with LS mean≥1 that were significant (ANOVA $p<0.05$) in either CLF vs. CON and/or CLF+IXA vs. CON. Pair-wise GSA analysis for CLF vs. CON showed that 172 differentially expressed (DE) genes displayed p-value less than 0.05 (|fold-change|>1) in response to single-agent CLF treatment, 24 hours following drug exposure to 5 μM CLF. Among these, 45 genes had LS Mean≥1. FIG. 15 shows volcano plots for each pair-wise comparison using gene-specific analysis/GSA. FIG. 6A shows a heat map of the top DE (CON vs. CLF) genes. When single-agent CLF-induced kinetic changes for each HMCLs were considered separately—714, 426, 128, 33, and 10 genes were differentially regulated in RPMI8226, FLAM76, JIM3, U266, and LP1, respectively at |fold-change|>2 ($p<0.05$). This suggests that the number of highly expressed genes decreases with increase in drug resistance, which is consistent with earlier observations that GEP data may be highly influenced by the DE genes expressed in sensitive HMCLs (Mitra et al., 2020, Blood Cancer J., 10:78). The Venn diagram in FIG. 6B shows 46 significant ($p<0.05$) genes were common between all the CLF vs. CON signatures. IPA analysis (FIG. 6C) based on these shared gene signatures revealed mitochondrial dysfunction and oxidative phosphorylation as top canonical pathways and predicted downregulation of MYC as the top regulatory gene.

Figure 6D:
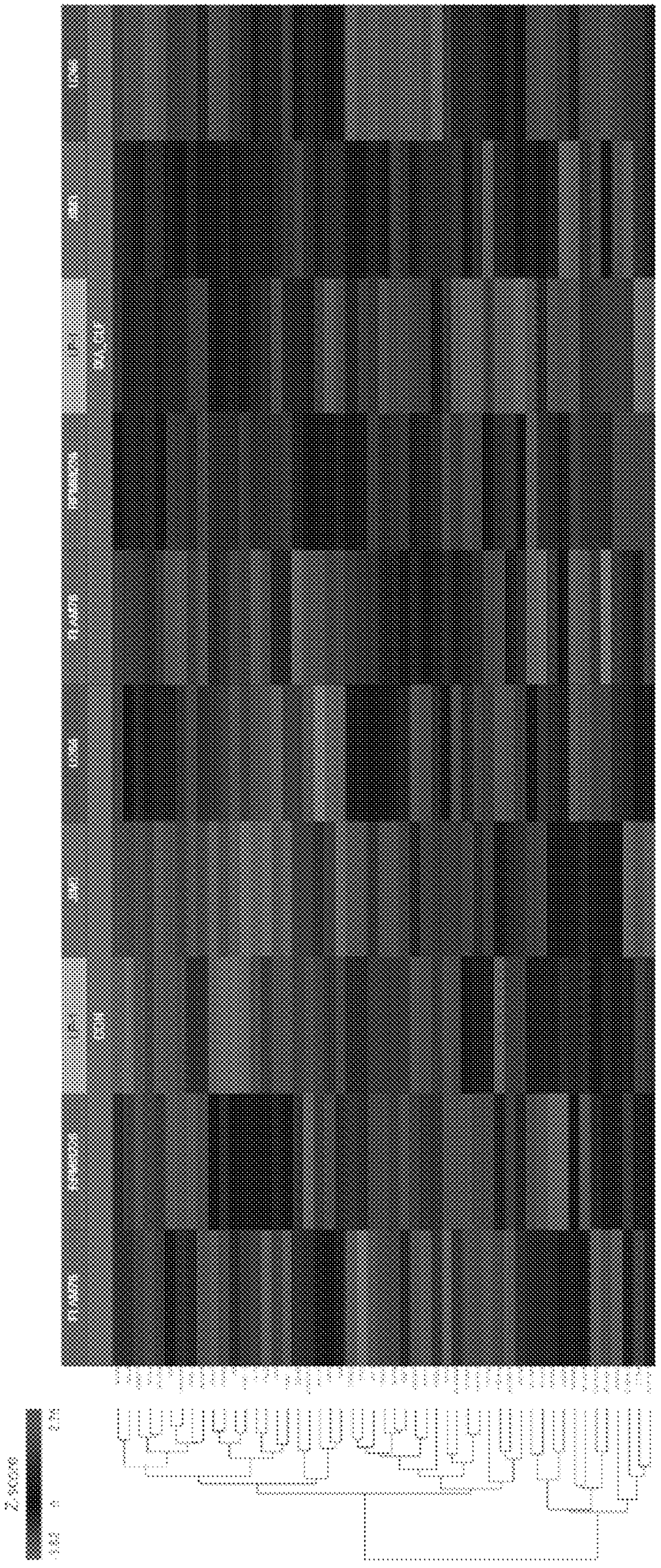
Figure 6E:
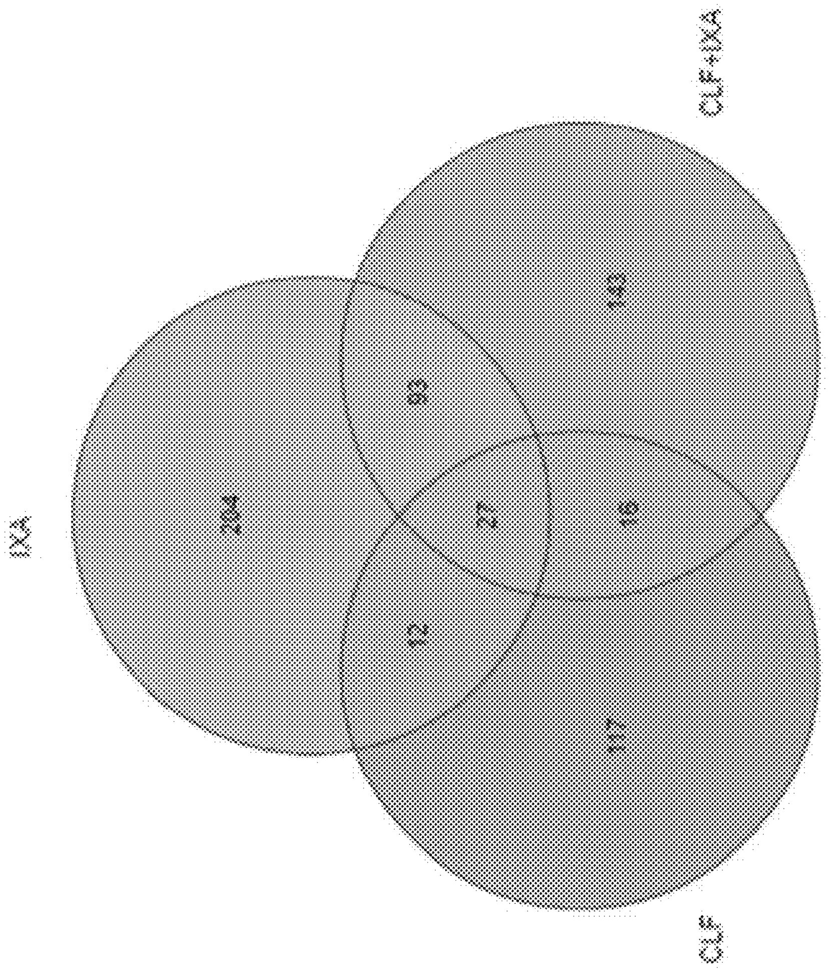

On the other hand, 279 genes changed significantly between untreated vs. CLF+Ixa combination-treated samples ($p<0.05$; fold-difference≠1). 179 genes had |fold-change|>2 ($p<0.05$). Among these, 114 genes had LS Mean of 1 or higher in both groups. FIG. 6D shows a heatmap of the top 50 genes associated with CLF+Ixa combination treatment. Seventy-one genes were common between the two comparisons (CLF vs. Control and CLF+Ixa vs. Control), as shown in the Venn diagram in FIG. 6E.

Figure 7A:
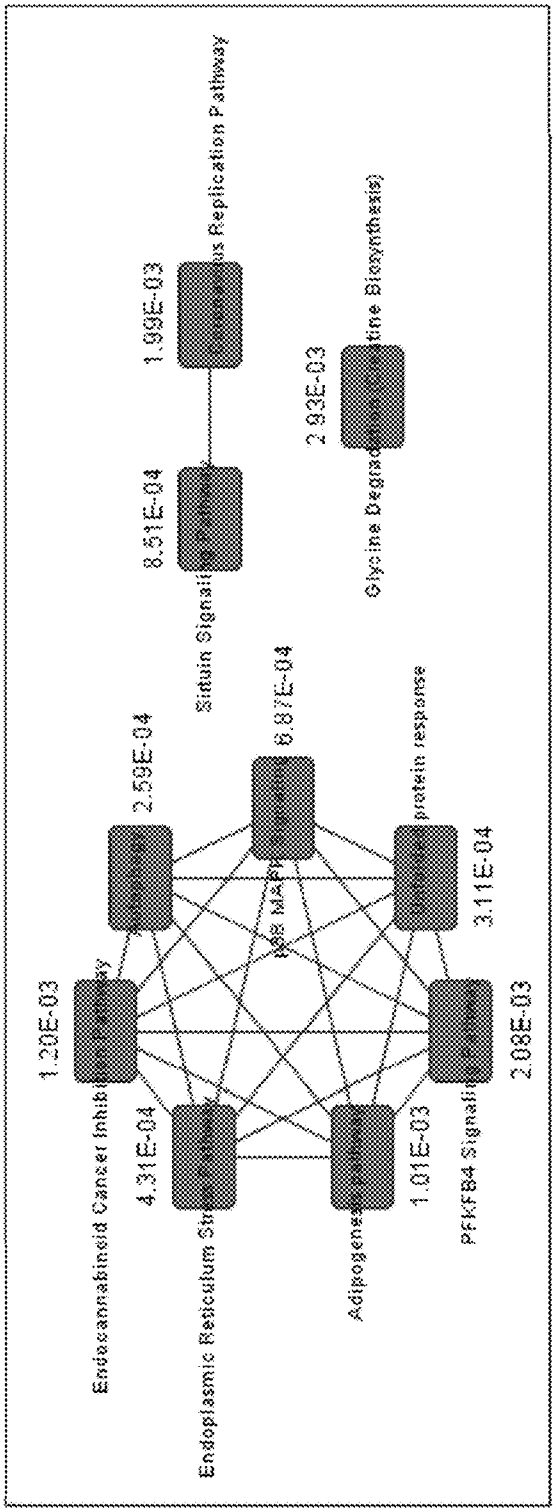
FIG. 7A through FIG. 7C depict representative results from experiments demonstrating the top pathways potentially associated with CLF mechanism of action and CLF-associated cell death. Ingenuity Pathway analysis (IPA) determines the top 10 canonical pathways predicted based on significantly differentially expressed biomarkers.
Figure 7B:
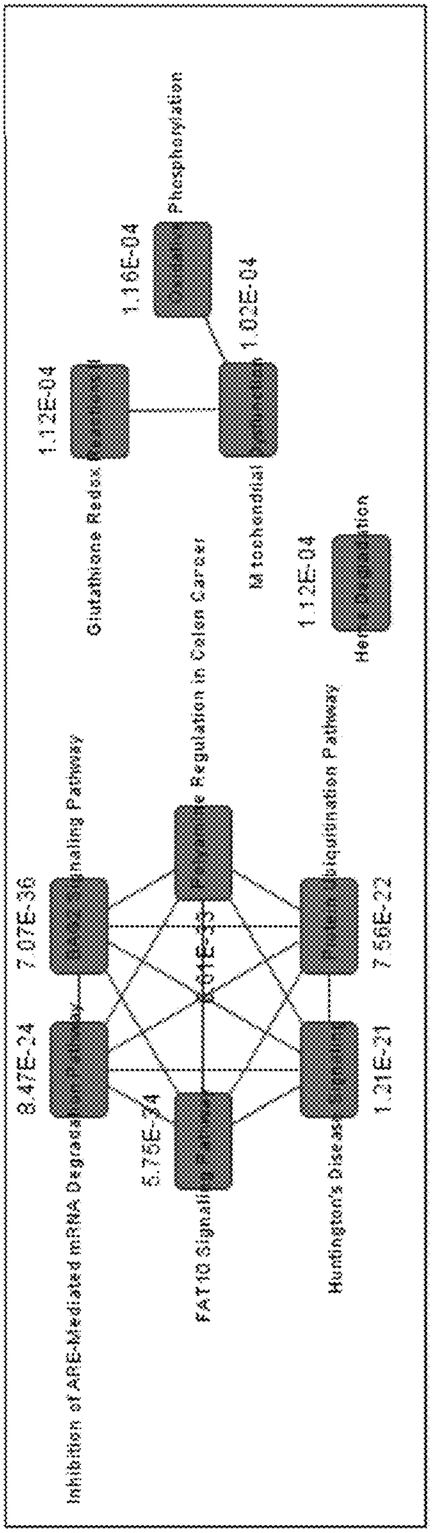
Figure 7C:
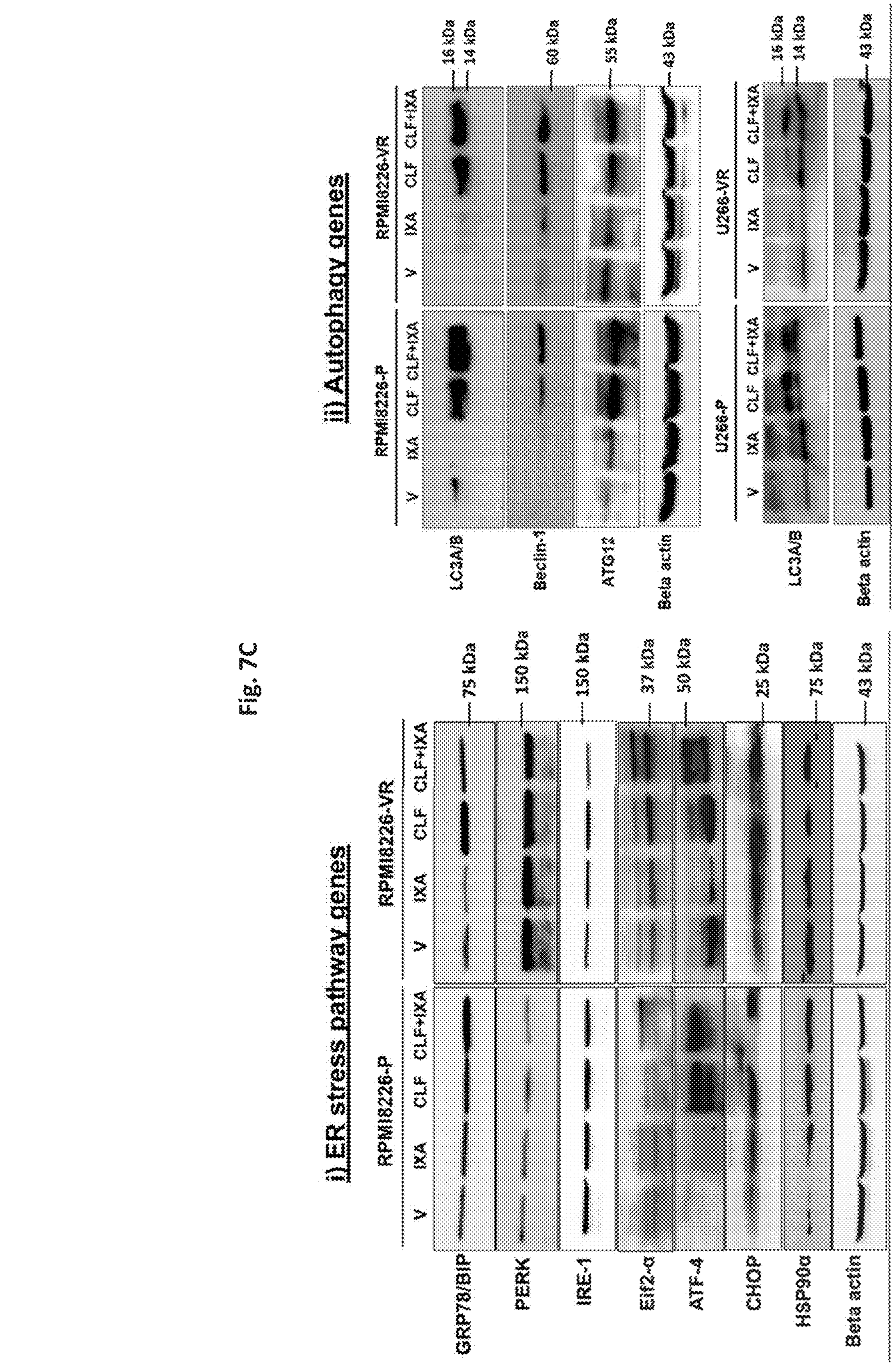
Figure 16:
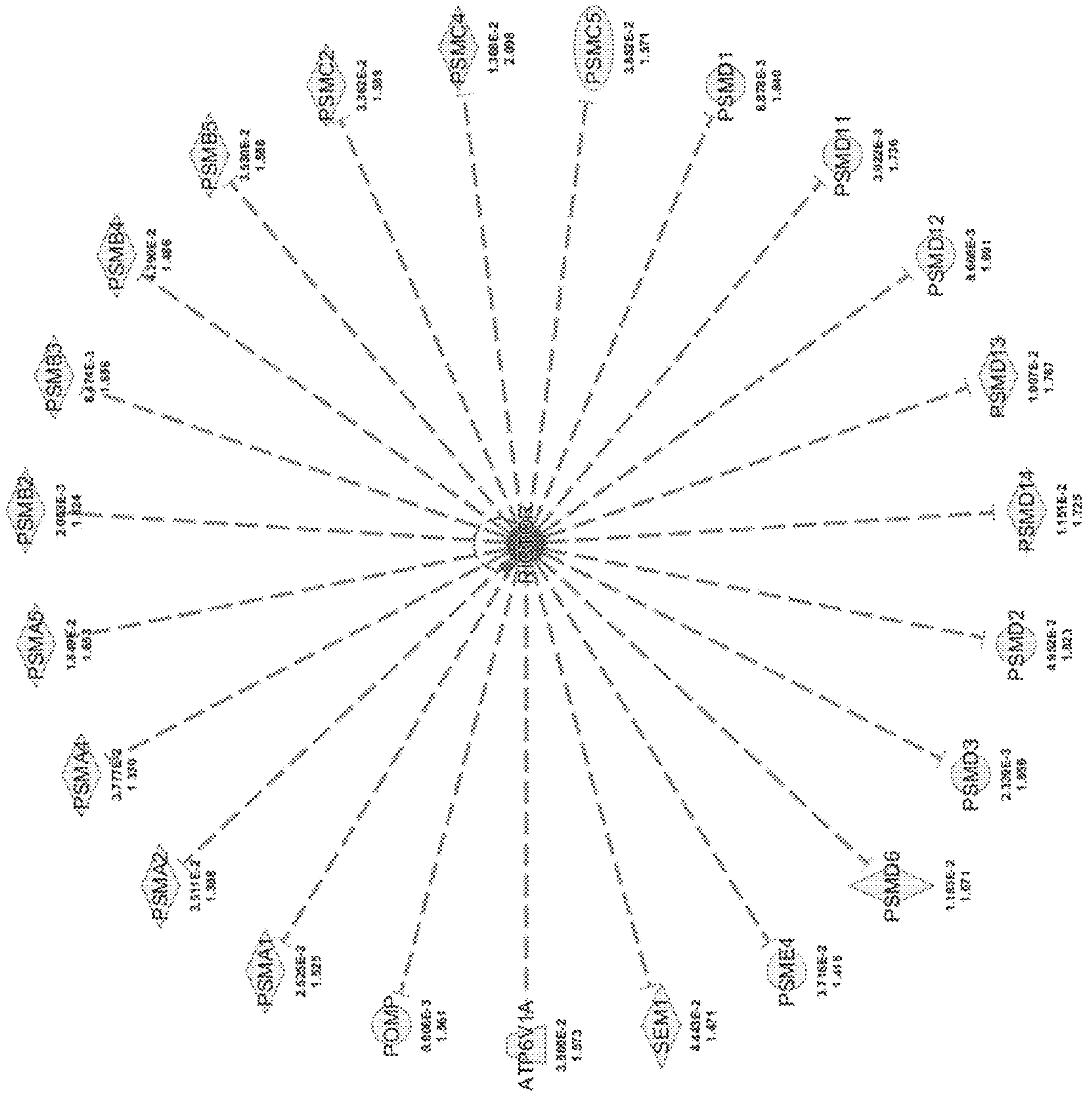
FIG. 16 depicts representative Ingenuity Pathway Analysis (IPA) results based on the top dysregulated genes following CLF+ixazomib combination treatment, showing downregulation of the mTOR signaling gene RICTOR (Rapamycin-Insensitive Companion of mammalian Target Of Rapamycin) as one of the top predictions.

IPA analysis based on top DE genes revealed autophagy ($p=2.59\times10^{-4}$), unfolded protein response ($p=3.11\times10^{-4}$), and ER stress pathway ($p=4.31\times10^{-4}$) as the top canonical pathways associated with CLF treatment gene signatures (FIG. 7A). BAG2 signaling ($p=7.07\times10^{-36}$), FAT10 signaling ($p=5.75\times10^{-34}$), polyamine regulation ($p=6.61\times10^{-33}$), inhibition of ARE-mediated mRNA degradation pathway ($p=8.47\times10^{-24}$) and protein ubiquitination ($p=7.56\times10^{-22}$) were among the top canonical pathways for CLF+PI combination treatment (FIG. 7B). Upstream regulator prediction revealed NR1H4, PPP1R15B, and UCP1 as top upstream regulars for CLF treatment and RICTOR (FIG. 16) and NFE2L2 for combination treatment. Results from the RNAseq and IPA analysis were confirmed using immunoblotting (FIG. 7C) as well as CyTOF analysis of ~40 different CLF treatment-induced markers in HMCLs, and PMCs, as shown earlier.

Figure 8:
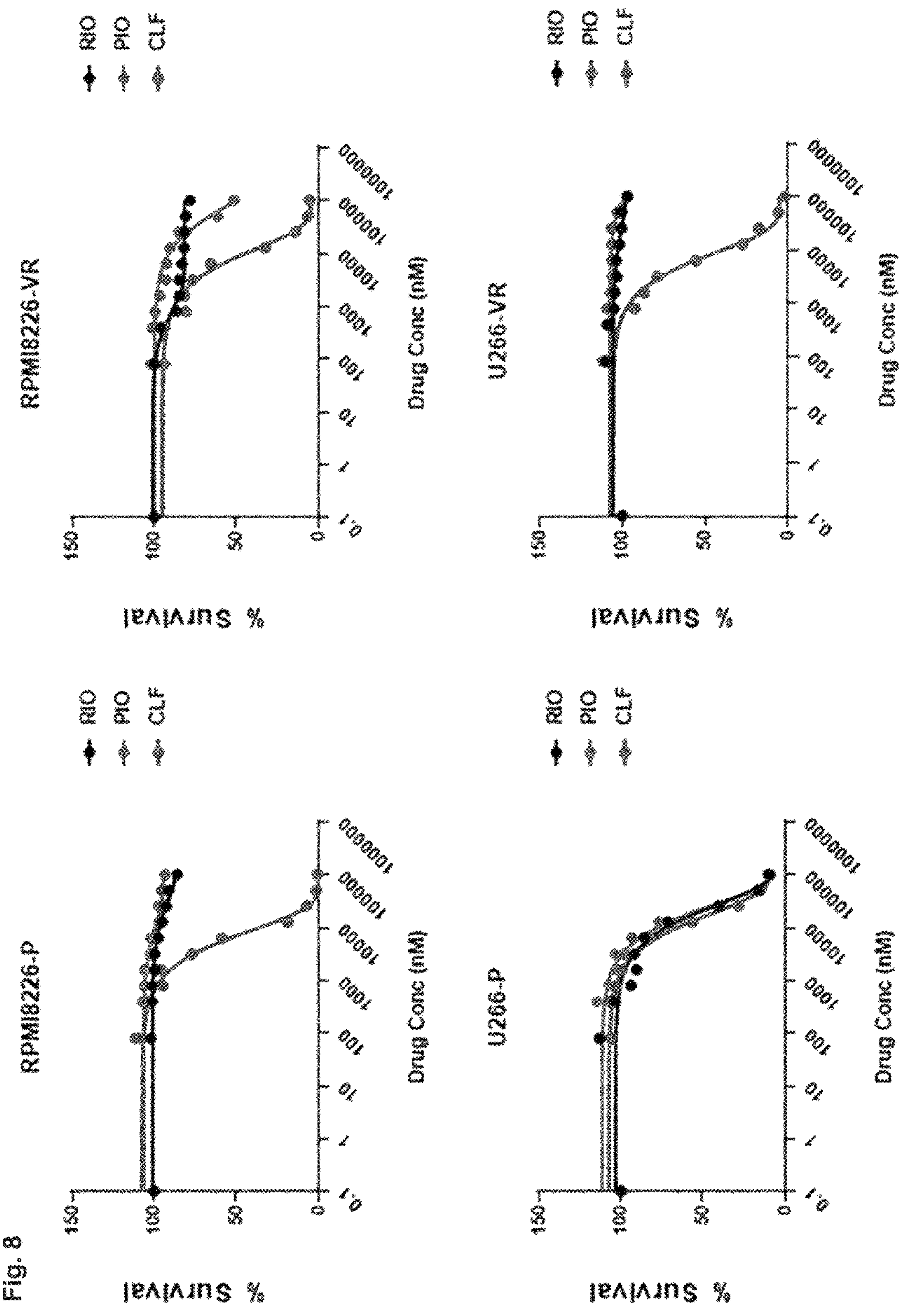
FIG. 8 depicts representative results from experiments demonstrating CLF shows superior single-agent cytotoxicity compared to other PPARγ agonists. RIO, rioglitazone; PIO, pioglitazone; CLF, clofazimine.

CLF Shows Superior Anti-Myeloma Cytotoxic Activity Compared to Other PPAR-Gamma Agonists Next, the anti-myeloma efficacy of CLF with that of other Peroxisome Proliferator Activated Receptor Gamma (PPARg) agonists—rosiglitazone and pioglitazone were compared. Single-agent CLF was found to be the most potent among all the PPARg agonists tested (FIG. 8).

CLF Response is Independent of Aryl Hydrocarbon Receptor (AHR) Expression

Figure 17A:
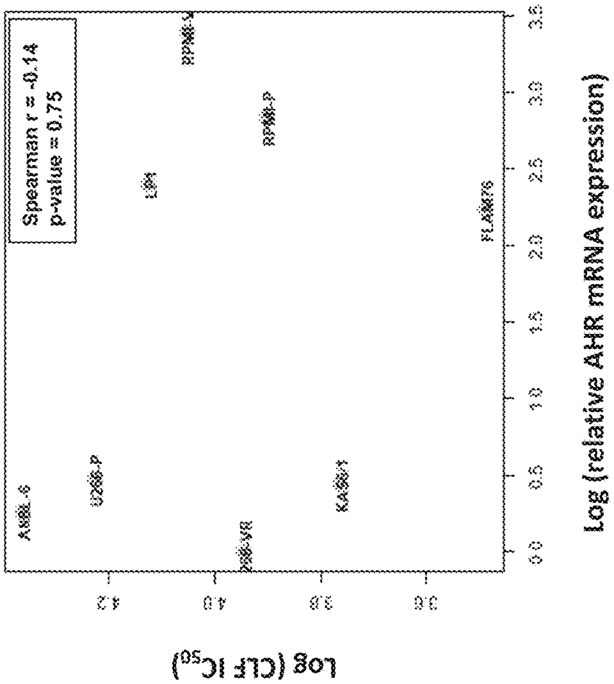
FIG. 17A through FIG. 17C depict representative results of experiments demonstrating that the CLF response is independent of AHR expression.
Figure 17B:
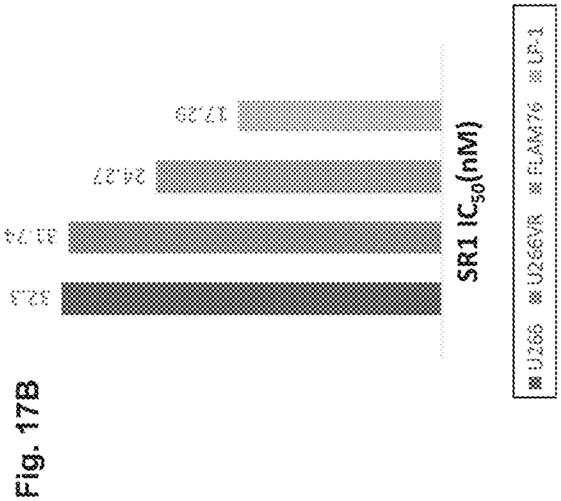
Figure 17C:
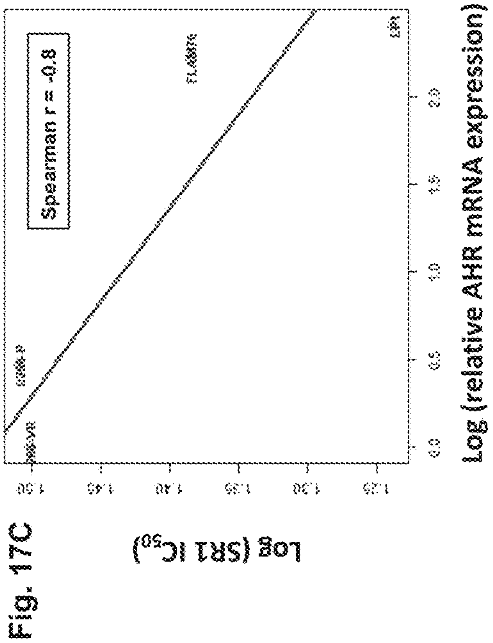
Figure 18A:
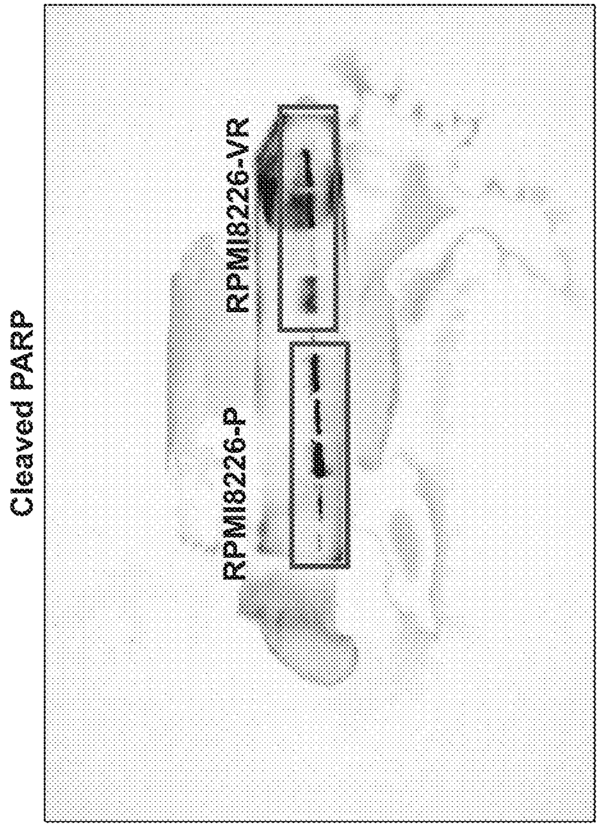
FIG. 18A and FIG. 18B, enlarged images of Western blots from FIG. 4C, demonstrating that CLF treatment induces PARP cleavage and caspase cleavage, resulting in apoptosis in sensitive and innate resistant MINI cell lines.
Figure 18B:
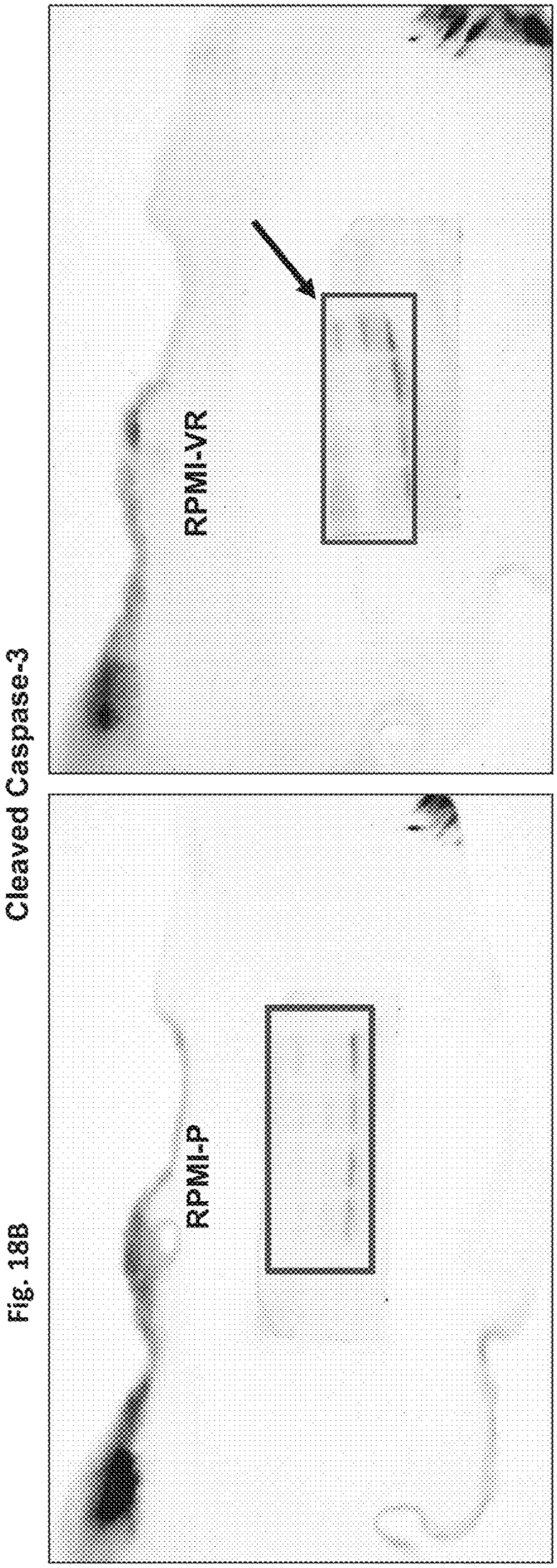

An earlier study had reported that the anti-myeloma effect of CLF was due to its inhibition of the AHR-polyamine metabolism axis (Bianchi-Smiraglia et al., 2018, J Clin Invest., 128:4682-96). AHR expression was evaluated using qRT-PCR (TaqMan® Real-Time PCR Assays) in 10 myeloma cell lines and compared AHR expression with CLF cytotoxicity. Relative AHR expression (ΔCt) in the myeloma lines was calculated following normalization with Beta-Actin (housekeeping gene). Since the U266 VR cell line showed the lowest relative AHR expression, the ΔCt value of this line as the baseline was used to compute relative fold gene expression of all the HMCLs using the 2-ΔΔCt method (Livak et al., 2001, Methods., 25:402-8). The scatter plot in FIG. 17A shows that AHR expression was not significantly correlated with CLF response in myeloma cell lines (Spearman r=−0.14; p-value=0.75). Furthermore, FIG. 17B shows the cytotoxicity data of the AHR antagonist StemRegenin 1 (SR1) in FLAM76, LP1, U266P, and U266VR cell lines. As represented by IC50 values, treatment with SR1 was found to be dependent upon baseline AHR expression (AHR-negative U266 P/VR and FLAM76 lines were highly resistant to SR1 compared to LP1; FIG. 17C), while CLF treatment response was not correlated with AHR expression (FIG. 17A).

CLF Increases Therapeutic Efficacy of PI and IMiDs in Myeloma

Drug resistance in multiple myeloma is largely attributed to tumor heterogeneity and inter-individual variations in response to treatment, limiting the therapeutic efficacy in myeloma patients (Rajkumar SV, 2016, Am J Hematol., 91:90-100; Vangsted et al., 2012, Eur J Haematol., 88:93-117; Rajkumar et al., 2014, Lancet Oncol., 15:e538-48). Experiments demonstrated that wide inter-individual variation exists in response to PI treatment in a panel of HMCLs and PMCs representing the broad spectrum of biological and genetic heterogeneity of myeloma (Mitra et al., 2017, Blood Cancer J., 7:e581.). Experiments demonstrated significant in vitro and ex vivo cytotoxicity of CLF against these PI- and IMiD-sensitive and resistant myeloma, both as single agent and in combination with PIs and IMiDs. Further, RNAseq-based next-generation tumor gene expression profiling, single-cell proteomics (CyTOF) analysis, and immunoblotting analysis were performed to identify genes and molecular networks involved in CLF mechanism of action and drug synergy in human myeloma.

Clofazimine is a riminophenazine drug that is approved by the FDA for the treatment of leprosy and has also been shown effective against multidrug-resistant tuberculosis (Gopal et al., 2013, Int J Tuberc Lung Dis., 17:1001-7). CLF exerts its anti-bacterial actions by producing reactive oxygen species (ROS) like superoxides and hydrogen peroxide ($H_2O_2$) (Cholo et al., 2012, J Antimicrob Chemother., 67:290-8). Antioxidants or oxygen scavengers like alpha-tocopherol have been shown to reverse this multidrug-resistance-reversal activity of CLF (Van Rensburg et al., 1998, Cancer Lett., 127:107-12).

Further, CLF displays anti-inflammatory properties resulting in the suppression of immune reactions in leprosy as well as in autoimmune diseases (Ren et al., 2008, PloS One., 3:e4009.). Notably, a very recent study has also shown CLF possesses pan-coronaviral inhibitory activity against the ongoing global COVID-19 (SARS-CoV-2) pandemic (Yuan et al., 2021, Nature., 589(7859):418-23).

CLF binds to PPARg, which results in modulation of its transcriptional as well as E3 ubiquitin ligase activity (Kumar et al., 2019, Haematologica., 105:971-86). This increased ubiquitin ligase activity of PPARg induces proteasomal degradation of p65, which in turn results in sequential transcriptional downregulation of MYB and PRDX1, resulting in the cellular effects of CLF including regulation of cellular ROS levels (Kumar et al., 2019, Haematologica., 105:971-86). This was consistent with IPA analysis results in myeloma showing BEX2 signaling as the top canonical pathway associated with CLF treatment. The BEX2/NFκB pathway has pro-oncogenic function that includes p65/RelA, NFkB, JUN (Naderi et al., 2019, Exp Cell Res., 376:221-6). Earlier studies have shown that BEX2 is the target gene of p65/RelA in cancers and, as a feedback mechanism, regulates the phosphorylation/activity of p65/RelA (Naderi et al., 2007, Cancer Res., 67:6725-36).

In addition, CLF induces ER stress and crosslinks with autophagy for myeloma cell death, in addition to alteration in mitochondrial membrane potential and oxidative phosphorylation. The endoplasmic reticulum (ER) is the primary site for the correct folding and sub-cellular trafficking of proteins, as well as for the initial phase of unfolded protein response (UPR) following ER stress or the accumulation of misfolded or unfolded proteins in the ER (Szegezdi et al., 2006, EMBO Rep., 7:880-5) (Vincenz et al., 2013, Mol Cancer Ther., 12:831-4). The ER stress pathway is involved in i) first, resolving the stress by several mechanisms, including augmenting the removal of unfolded proteins through ER-associated degradation (ERAD) and inducing autophagy (Vincenz et al., 2013, Mol Cancer Ther., 12:831-4) (Friedlander et al., 2000, Nat Cell Biol., 2:379-84) (Deeganet al., 2013, Cell Mol Life Sci., 70:2425-41). and ii) in case of failure to resolve the stress, activating cell death or ER stress-induced apoptosis predominantly through the mitochondrial pathway (Gupta et al., 2010, Int J Cell Biol., 2010:170215).

Experiments using mRNA sequencing, IPA pathway analysis, and Western blotting, experiments showed that CLF treatment induces the proteins involved ER stress pathway, including the ER stress sensors inositol-requiring enzyme 1 (IRE1), PKR-like ER kinase (PERK, EIFA2K3), and activating transcription factor 6 (ATF6), as well as the proteins involved in autophagy in myeloma, which in turn results in induction of apoptosis through the mitochondria-mediated pathway and BCL2-family proteins. This presents a possible mechanism of action of CLF efficacy in myeloma.

IPA analysis for CLF+PI combination treatment showed that BAG2 signaling, protein ubiquitination, and FAT10 signaling are among the top canonical pathways. FAT10 is a ubiquitin-like protein modifier that serves as a proteasomal degradation signal regulated by ubiquitination (Buchsbaum et al., 2012, Mol Biol Cell., 23:225-32). Thus, it is suggested that CLF acts as a PPAR-gamma agonist that synergizes with PIs and IMiDs in myeloma to enhance the downstream cascade of p65-NFkB-IRF4-Myc downregulation followed by ROS-dependent apoptotic cell death. Furthermore, phenotypic and functional characterization by single-cell proteomics (mass cytometry or CyTOF) analysis also showed elevated cleaved caspase-3 levels and downregulation of pS6, IRF4, pCREB, pRB, IKZF1 in HMCLs and patient-derived primary cells, irrespective of PI- or IMiD-resistance.

A number of studies have shown that the presence of rare subtypes of tumor cell subclones (less-mature cells, or putative cell progenitors or cancer 'stem cell-like' cells or CSCs) that are refractory to therapies contribute to drug resistance in various cancers (Matsui et al., 2004, Blood., 103:2332-2336; Blair et al., 1998, Blood, 92:4325-3555; Singh et al., 2003, Cancer Res., 63:5821-8; Prince et al., 2007, Proc Natl Acad Sci USA, 104:973-8). Although the exact role and phenotype of these subpopulations in myeloma are unknown, but variously, these cells are thought to include CD138− with memory B-cells (CD19+/CD27+), CD38high/CD138+ cells, and side population (SP) cells (Matsui et al., 2008, Cancer Res., 68:190-7; Loh et al., 2008, Leuk Lymphoma, 49:1813-6; Kim et al., 2012, Myeloma Cells. Leukemia, 26:2530-7; Reghunathan et al., 2013, Oncotarget, 4:1230-40). Further, myeloma cells with high ALDH activity have also been shown to possess tumorigenesis capacities in vitro and in vivo (Zhou et al., 2014, Leukemia, 28:1155-8; Jin et al., 2018, J Cell Biochem., 119:6882-93). Significantly, this study found that CLF is particularly effective against these putative myeloma stem-cell-like subclones with treatment-refractory phenotypes, including quiescent cells/dormant cells, ALDH+ cells, and SPs. This demonstrates a unique property of this drug that may be particularly useful in more effective tumor eradication.

Taken together, CLF has strong single-agent cytotoxicity as well as the potential to increase the therapeutic efficacy of standard-of-care drugs (PI and IMiDs) in myeloma, including treatment-resistant and putative stem-like subclones.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of treating a drug resistant myeloma in a subject comprising administering to the subject a therapeutically effective amount of a composition comprising clofazimine or a pharmaceutically acceptable salt or hydrate thereof, wherein the drug resistant myeloma is selected from the group consisting of a proteasome inhibitor (PI)-resistant myeloma cell, an immunomodulatory-drug-resistant myeloma, an immunomodulatory derivative (IMiD)-resistant myeloma, a cereblon (CRBN)-negative myeloma, an innate myeloma, a refractory myeloma, a stem-like myeloma, and any combination thereof.

2. The method of claim 1, wherein the method further comprises administering to the subject a therapeutically effective amount of one or more proteasome inhibitors.

3. The method of claim 2, wherein the one or more proteasome inhibitors are selected from the group consisting of bortezomib, carfilzomib, oprozomid, marizomib, delanzomib, and ixazomib.

4. The method of claim 2, wherein i) the one or more proteasome inhibitors and ii) clofazimine, or the pharmaceutically acceptable salt or hydrate thereof, are administered simultaneously to the subject.

5. The method of claim 2, wherein i) the one or more proteasome inhibitors and ii) clofazimine, or the pharmaceutically acceptable salt or hydrate thereof, are administered at different times to the subject.

6. The method of claim 1, wherein the method further comprises administering to the subject a therapeutically effective amount of one or more immunomodulatory drugs.

7. The method of claim 6, wherein the one or more immunomodulatory drugs are selected from the group consisting of lenalidomide, pomalidomide, thalidomide, and imiquimod.

8. The method of claim 6, wherein i) the one or more immunomodulatory drugs and ii) clofazimine, or the pharmaceutically acceptable salt or hydrate thereof, are administered simultaneously to the subject.

9. The method of claim 6, wherein i) the one or more immunomodulatory drugs and ii) clofazimine, or the pharmaceutically acceptable salt or hydrate thereof, are administered at different times to the subject.

10. The method of claim 1, wherein the drug resistant myeloma is resistant to one or more proteasome inhibitors and/or to one or more immunomodulatory drugs.

11. The method of claim 1, wherein the drug resistant myeloma is selected from the group consisting of a cereblon (CRBN)-negative myeloma, an innate myeloma, a refractory myeloma, a stem-like myeloma, and any combination thereof.

12. A method of treating a myeloma in a subject comprising administering to the subject a therapeutically effective amount of a composition comprising clofazimine or a pharmaceutically acceptable salt or hydrate thereof and one or more proteasome inhibitors.

13. The method of claim 12, wherein the one or more proteasome inhibitors are selected from the group consisting of bortezomib, carfilzomib, oprozomid, marizomib, delanzomib, and ixazomib.

14. The method of claim 12, wherein i) the one or more proteasome inhibitors and ii) clofazimine, or the pharmaceutically acceptable salt or hydrate thereof, are administered simultaneously to the subject.

15. The method of claim 12, wherein i) the one or more proteasome inhibitors and ii) clofazimine, or the pharmaceutically acceptable salt or hydrate thereof, are administered at different times to the subject.

16. The method of claim 12, wherein the method further comprises administering a therapeutically effective amount of one or more immunomodulatory drugs to the patient, wherein the one or more immunomodulatory drugs are selected from the group consisting of lenalidomide, pomalidomide, thalidomide, and imiquimod.

17. A method of treating a myeloma in a subject comprising administering to the subject a therapeutically effective amount of a composition comprising clofazimine or a pharmaceutically acceptable salt or hydrate thereof and one or more immunomodulatory drugs.

18. The method of claim 17, wherein the one or more immunomodulatory drugs are selected from the group consisting of lenalidomide, pomalidomide, thalidomide, and imiquimod.

19. The method of claim 17, wherein i) the one or more immunomodulatory drugs and ii) clofazimine, or the pharmaceutically acceptable salt or hydrate thereof, are administered simultaneously to the subject.

20. The method of claim 17, wherein i) the one or more immunomodulatory drugs and ii) clofazimine, or the pharmaceutically acceptable salt or hydrate thereof, are administered at different times to the subject.

21. The method of claim 17, wherein the method further comprises administering a therapeutically effective amount of one or more proteasome inhibitors to the patient, wherein the one or more proteasome inhibitors are selected from the group consisting of bortezomib, carfilzomib, oprozomid, marizomib, delanzomib, and ixazomib.

* * * * *